US010344296B2

(12) United States Patent
Schultheiss et al.

(10) Patent No.: US 10,344,296 B2
(45) Date of Patent: Jul. 9, 2019

(54) FUNGAL RESISTANT PLANTS EXPRESSING HYDROPHOBIN

(71) Applicant: BASF Plant Science Company GmbH, Ludwigshafen (DE)

(72) Inventors: Holger Schultheiss, Boehl-Iggelheim (DE); Ralf Flachmann, Limburgerhof (DE); Thomas Subkowski, Schriesheim (DE); Claus Bollschweiler, Heidelberg (DE)

(73) Assignee: BASF PLANT SCIENCE COMPANY GMBH, Ludwigshafen (DE)

( * ) Notice: Subject to any disclaimer, the term of this patent is extended or adjusted under 35 U.S.C. 154(b) by 764 days.

(21) Appl. No.: 14/390,574

(22) PCT Filed: Mar. 15, 2013

(86) PCT No.: PCT/EP2013/055318
§ 371 (c)(1),
(2) Date: Oct. 3, 2014

(87) PCT Pub. No.: WO2013/149801
PCT Pub. Date: Oct. 10, 2013

(65) Prior Publication Data

US 2015/0074842 A1 Mar. 12, 2015

Related U.S. Application Data

(60) Provisional application No. 61/620,454, filed on Apr. 5, 2012.

(30) Foreign Application Priority Data

Apr. 5, 2012 (EP) .................................... 12163267

(51) Int. Cl.
*C12N 15/82* (2006.01)
*C07K 14/37* (2006.01)
*C07K 14/38* (2006.01)
*C12N 15/62* (2006.01)

(52) U.S. Cl.
CPC .......... *C12N 15/8282* (2013.01); *C07K 14/37* (2013.01); *C07K 14/38* (2013.01); *C12N 15/625* (2013.01)

(58) Field of Classification Search
CPC ................................................. C12N 15/8282
See application file for complete search history.

(56) References Cited

U.S. PATENT DOCUMENTS

| | | | |
|---|---|---|---|
| 7,892,788 B2 | 2/2011 | Subkowski et al. | |
| 7,910,699 B2 | 3/2011 | Subkowski et al. | |
| 7,981,313 B2* | 7/2011 | Baus .................. | C09K 3/18 106/13 |
| 2009/0101167 A1 | 4/2009 | Boeckh et al. | |
| 2012/0006354 A1 | 1/2012 | Baus et al. | |
| 2013/0219559 A1* | 8/2013 | Koivu ................ | C12N 15/8257 800/287 |
| 2014/0137284 A1 | 5/2014 | Schultheiss et al. | |

FOREIGN PATENT DOCUMENTS

| | | |
|---|---|---|
| WO | WO 2002010414 | 2/2002 |
| WO | WO 2006/082251 | * 8/2006 |
| WO | WO 2006082251 | 8/2006 |
| WO | WO 2006131564 | 12/2006 |
| WO | WO 2007014897 | 2/2007 |
| WO | WO 2009158694 | 12/2009 |
| WO | WO 2011121009 | 10/2011 |
| WO | WO 2012004255 | 1/2012 |
| WO | WO 2012023099 | 2/2012 |
| WO | WO 2012023111 | 2/2012 |
| WO | WO 2012025582 | 3/2012 |
| WO | WO 2012049250 | 4/2012 |
| WO | WO 2012085808 | 6/2012 |
| WO | WO 2012127373 | 9/2012 |
| WO | WO 2012160528 | 11/2012 |
| WO | WO 2012172498 | 12/2012 |
| WO | WO 2013001435 | 1/2013 |
| WO | WO 2013041621 | 3/2013 |
| WO | WO 2013092275 | 6/2013 |
| WO | WO 2013093738 | 6/2013 |
| WO | WO 2013149804 | 10/2013 |
| WO | WO 2013152917 | 10/2013 |
| WO | WO 2014024079 | 2/2014 |

(Continued)

OTHER PUBLICATIONS

Joensuu et al 2010, Plant Physiology 152: 622-633.*
Wu et al 1995, The Plant Cell 7: 1357-1368.*
Wosten 2001, Annual Review of Microbiology 55: 625-646.*
Bayry et al 2012, PLoS Pathogens 8(5): 1-4.*
Bell-Pedersen et al., "The *Neurospora* Circadian Clock-Controlled Gene, ccg-2, is Allelic to eas and Encodes a Fungal Hydrophobin Required for Formation of the Conidial Rodlet Layer," Genes & Development, vol. 6, (1992), pp. 2382-2394.
Heath, "Cellular Interactions Between Biotrophic Fungal Pathogens and Host or Nonhost Plants," Can. J. Plant Pathol., vol. 24, (2002), pp. 259-264.

(Continued)

*Primary Examiner* — David H Kruse
(74) *Attorney, Agent, or Firm* — Marshall, Gerstein & Borun LLP

(57) ABSTRACT

The present invention relates to a method of increasing resistance against fungal pathogens of the family Phacopsoraceae plants and/or plant cells. This is achieved for instance by increasing the expression of a hydrophobin protein or fragment thereof in a plant, plant part and/or plant cell in comparison to wild type plants, wild type plant parts and/or wild type plant cells. In the transgenic plants hydrophobin can be expressed as a fusion protein to facilitate and/or enhance expression. Furthermore, the hydrophobin protein can be expressed including a secretion signal sequence which mediates secretion of the protein into the apoplast and/or into the cuticule.

21 Claims, 11 Drawing Sheets

Figure 1:
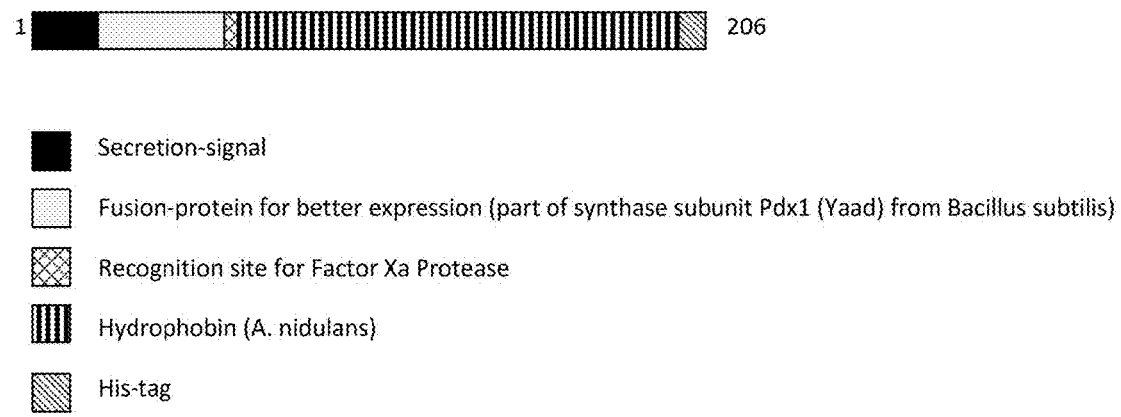

Specification includes a Sequence Listing.

(56) References Cited

FOREIGN PATENT DOCUMENTS

| WO | WO 2014024090 | 2/2014 |
|---|---|---|
| WO | WO 2014024102 | 2/2014 |
| WO | WO 2014041444 | 3/2014 |
| WO | WO 2014076614 | 5/2014 |
| WO | WO 2014117988 | 8/2014 |
| WO | WO 2014117990 | 8/2014 |
| WO | WO 2014118018 | 8/2014 |

OTHER PUBLICATIONS

International Preliminary Report on Patentability, issued in PCT/EP2013/055318, dated Oct. 16, 2014.

International Search Report, issued in PCT/EP2013/055318, dated May 14, 2013.

Kershaw and Talbot, "Hydrophobins and Repellents: Proteins with Fundamental Roles in Fungal Morphogenesis," Fungal Genetics and Biology, vol. 23, (1998), pp. 18-33.

Neu et al., "Cytological and Molecular Analysis of the *Hordeum vulgare-Puccinia triticina* Nonhost Interaction," MPMI, vol. 16, No. 7, (2003), pp. 626-633.

Rytter, "Additional Alternative Hosts of *Phakopsora pachyrhizi*, Causal Agent of Soybean Rust," Plant Disease, vol. 68, No. 9, (1984), pp. 818-819.

Smith, "Known Host Crops for *Phakopsora pachyrhizi* Causal Agent of Soybean Rust (SBR)," [on-line], retrieved from lsuagcenter.com/MCMS/RelatedFiles/%7B04022BD3-1FBB-402B-8FD1-8CEB97FB2F2C%7D/Known+Hosts+for+Asian+Soybean+Rust.pdf, [retrieved on Jun. 8, 2012].

Soybean Rust Workshop, eds. Sinclair and Hartman, (Aug. 9-11, 1995), pp. 1-11.

Tucker and Talbot, "Surface Attachment and Pre-Penetration Stage Development by Plant Pathogenic Fungi," Annu. Rev. Phytopathol., vol. 39, (2001), pp. 385-417.

Van Wetter et al., "SC3 and SC4 Hydrophobins have Distinct Roles in Formation of Aerial Structures in Dikaryons of *Schizophyllum commune*," Molecular Microbiology, vol. 36, No. 1, (2000), pp. 201-210.

Wessels, "Fungal Hydrophobins: Proteins that Function at an Interface," Trends in Plant Science, vol. 1, No. 1, (1996), pp. 9-15.

Whiteford and Spanu, "The Hydrophobin HCf-1 of *Cladosporium fulvum* is Required for Efficient Water-Mediated Dispersal of Conidia," Fungal Genetics and Biology, vol. 32, (2001), pp. 159-168.

Wösten and de Vocht, "Hydrophobins, the Fungal Coat Unravelled," Biochimica et Biophysica Acta, vol. 1469, (2000), pp. 79-86.

Wösten et al., "How a Fungus Escapes the Water to Grow into the Air," Current Biology, vol. 9, (1999), pp. 85-88.

\* cited by examiner

Figure 3:

```
  1 ATGAAGACTA ACCTGTTCCT CTTCCTGATC TTCTCACTTT TGCTTAGCCT
 51 TAGCTCAGCT GCTCAAACTG GAACTGAAAG GGTTAAGAGG GGTATGGCTG
101 AAATGCAAAA GGGTGGTGTG ATTATGGACG TGATCAACGC TGAGCAGGCT
151 AAGATTGCTG AAGAGGCTGG TGCTGTTATT GAGGGTAGAA TGCGTTTTAT
201 CGTTAGCCTT CTTGCTTTCA CTGCTGCTGC TACTGCTACA GCTTTGCCAG
251 CTAGTGCTGC TAAGAACGCT AAGCTTGCTA CTAGTGCTGC TTTCGCTAAG
301 CAAGCTGAGG GAACTACTTG TAACGTGGGA TCTATTGCCT GCTGTAACTC
351 ACCAGCTGAG ACTAACAACG ATAGCCTTCT TAGTGGACTT CTTGGAGCTG
401 GACTTCTTAA CGGACTTAGT GGTAACACTG GATCAGCTTG CGCTAAGGCT
451 AGCCTTATTG ATCAACTTGG ACTTCTTGCT CTCGTTGATC ACACTGAAGA
501 GGGACCAGTG TGTAAGAATA TTGTGGCTTG CTGCCCAGAG GGTACTACTA
551 ACTGTGTTGC TGTTGATAAC GCTGGTGCTG GAACTAAGGC TGAAGGTAGT
601 CATCATCATC ACCATCACTA A
```

Figure 4:

MKTNLFLFLIFSLLLSLSSAAQTGTERVKRGMAEMQKGGVIMDVINAEQAKIAEEAGAVIEG
RMRFIVSLLAFTAAATATALPASAAKNAKLATSAAFAKQAEGTTCNVGSIACCNSPAETNN
DSLLSGLLGAGLLNGLSGNTGSACAKASLIDQLGLLALVDHTEEGPVCKNIVACCPEGTTN
CVAVDNAGAGTKAEGSHHHHHH

Figure 5:

```
  1 ATGAAGACTA ACCTGTTCCT CTTCCTGATC TTCTCACTTT TGCTTAGCCT
 51 TAGCTCAGCT GCTCAAACTG GAACTGAAAG GGTTAAGAGG GGTATGGCTG
101 AAATGCAAAA GGGTGGTGTG ATTATGGACG TGATCAACGC TGAGCAGGCT
151 AAGATTGCTG AAGAGGCTGG TGCTGTTATT GAGGGTAGAA TGCGTTTTAT
201 CGTTAGCCTT CTTGCTTTCA CTGCTGCTGC TACTGCTACA GCTTTGCCAG
251 CTAGTGCTGC TAAGAACGCT AAGCTTGCTA CTAGTGCTGC TTTCGCTAAG
301 CAAGCTGAGG GAACTACTTG TAACGTGGGA TCTATTGCCT GCTGTAACTC
351 ACCAGCTGAG ACTAACAACG ATAGCCTTCT TAGTGGACTT CTTGGAGCTG
401 GACTTCTTAA CGGACTTAGT GGTAACACTG GATCAGCTTG CGCTAAGGCT
451 AGCCTTATTG ATCAACTTGG ACTTCTTGCT CTCGTTGATC ACACTGAAGA
501 GGGACCAGTG TGTAAGAATA TTGTGGCTTG CTGCCCAGAG GGTACTACTA
551 ACTGTGTTGC TGTTGATAAC GCTGGTGCTG GAACTAAGGC TGAATAA
```

MKTNLFLFLIFSLLLSLSSAAQTGTERVKRGMAEMQKGGVIMDVINAEQAKIAEEAGAVIEG
RMRFIVSLLAFTAAATATALPASAAKNAKLATSAAFAKQAEGTTCNVGSIACCNSPAETNN
DSLLSGLLGAGLLNGLSGNTGSACAKASLIDQLGLLALVDHTEEGPVCKNIVACCPEGTTN
CVAVDNAGAGTKAE

Figure 8:

```
                         1                                                          60
              yaad   (1) ------------------MAQTGTERVKRGMAEMQKGGVIMDVINAEQAKIAEEAGAVA
          yaaD_TT1   (1) ------------------MAQTGTERVKRGMAEMQKGGVIMDVINAEQAKIAEEAGAVA
          yaaD_HFPI  (1) ------------------MAQTGTERVKRGMAEMQKGGVIMDVINAEQAKIAEEAGAVA
          yaaD_HFBII (1) ------------------MAQTGTERVKRGMAEMQKGGVIMDVINAEQAKIAEEAGAVA
           HFBII_V1  (1) ------------------------------------------------------------
           HFBII_V2  (1) ------------------------------------------------------------
   Hydrophbin_SC3_V2 (1) ----------------------------MFASLPWVFLYAFVAFSAWVAALP-------
   Hydrophbin_SC3_V1 (1) ------------------------------------------------------------
        Hydrophobin_Gm (1) MKTNLFLFLIFSLLLSLSSAQTGTERVKRGMAEMQKGGVIMDVINAEQAKIAEEAGAV- 61                                                        120
              yaad  (42) VMALERVPADIRAAGGVARMADPTIVEEVMNAVSIPVMAKARIGHIVEARVLEAMGVDYI
          yaaD_TT1  (42) VMALERVPADIRAAGGVARMADPTIVEEVMNAVSIPVMAKARIGHIVEARVLEAMGVDYI
          yaaD_HFPI (42) VMALERVPADIRAAGGVARMADPTIVEEVMNAVSIPVMAKARIGHIVEARVLEAMGVDYI
          yaaD_HFBII(42) VMALERVPADIRAAGGVARMADPTIVEEVMNAVSIPVMAKARIGHIVEARVLEAMGVDYI
           HFBII_V1  (1) ------------------------------------------------------------
           HFBII_V2  (1) ------------------------------------------------------------
   Hydrophbin_SC3_V2(25) ------------------------------------------------------------
   Hydrophbin_SC3_V1 (1) ------------------------------------------------------------
        Hydrophobin_Gm(60) ------------------------------------------------------------

121                                                       180
              yaad (102) DESEVLTPADEEFHLNKNEYTVPFVCGCRDLGEATRRIAEGASMLRTKGEPGTGNIVEAV
          yaaD_TT1 (102) DESEVLTPADEEFHLNKNEYTVPFVCGCRDLGEATRRIAEGASMLRTKGEPGTGNIVEAV
          yaaD_HFPI(102) DESEVLTPADEEFHLNKNEYTVPFVCGCRDLGEATRRIAEGASMLRTKGEPGTGNIVEAV
          yaaD_HFBII(102)DESEVLTPADEEFHLNKNEYTVPFVCGCRDLGEATRRIAEGASMLRTKGEPGTGNIVEAV
           HFBII_V1  (1) ------------------------------------------------------------
           HFBII_V2  (1) ------------------------------------------------------------
   Hydrophbin_SC3_V2(25) ------------------------------------------------------------
   Hydrophbin_SC3_V1 (1) ------------------------------------------------------------
        Hydrophobin_Gm(60) ------------------------------------------------------------

181                                                       240
              yaad (162) RHMRKVNAQVRKVVAMSEDELMTEAKNLGAPYELLLQIKKDGKLPVVNFAAGGVATPADA
          yaaD_TT1 (162) RHMRKVNAQVRKVVAMSEDELMTEAKNLGAPYELLLQIKKDGKLPVVNFAAGGVATPADA
          yaaD_HFPI(162) RHMRKVNAQVRKVVAMSEDELMTEAKNLGAPYELLLQIKKDGKLPVVNFAAGGVATPADA
          yaaD_HFBII(162)RHMRKVNAQVRKVVAMSEDELMTEAKNLGAPYELLLQIKKDGKLPVVNFAAGGVATPADA
           HFBII_V1  (1) ------------------------------------------------------------
           HFBII_V2  (1) ------------------------------------------------------------
   Hydrophbin_SC3_V2(25) ------------------------------------------------------------
   Hydrophbin_SC3_V1 (1) ------------------------------------------------------------
        Hydrophobin_Gm(60) ------------------------------------------------------------

241                                                       300
              yaad (222) ALMMQLGADGVFVGSGIFKSDNPAKFAKAIVEATTHFTDYKLIAELSKELGTAMKGIEIS
          yaaD_TT1 (222) ALMMQLGADGVFVGSGIFKSDNPAKFAKAIVEATTHFTDYKLIAELSKELGTAMKGIEIS
          yaaD_HFPI(222) ALMMQLGADGVFVGSGIFKSDNPAKFAKAIVEATTHFTDYKLIAELSKELGTAMKGIEIS
          yaaD_HFBII(222)ALMMQLGADGVFVGSGIFKSDNPAKFAKAIVEATTHFTDYKLIAELSKELGTAMKGIEIS
           HFBII_V1  (1) ------------------------------------------------------------
           HFBII_V2  (1) ------------------------------------------------------------
   Hydrophbin_SC3_V2(25) ------------------------------------------------------------
   Hydrophbin_SC3_V1 (1) ------------------------------------------------------------
        Hydrophobin_Gm(60) ------------------------------------------------------------

301                                                       360
              yaad (282) NLLPEQRMQERGW-----------------------------------------------
          yaaD_TT1 (282) NLLPEQRMQERGWRSMALPNVGPSGKTAHKPHQEPFWPVQQDVTVEQAKAICGEGNQVAC
          yaaD_HFPI(282) NLLPEQRMQERGWRSM--------------------------------------------
          yaaD_HFBII(282)NLLPEQRMQERGWRSM--------------------------------------------
           HFBII_V1  (1) ------------------------------------------------------------
           HFBII_V2  (1) ------------------------------------------------------------
   Hydrophbin_SC3_V2(25) --------------------------------------------GGHPGTTTPPVTTTVTT
   Hydrophbin_SC3_V1 (1) --------------------------------------------GGHPGTTTPPVTTTVTT
        Hydrophobin_Gm(60) -----------------IEGR--------MRFIVSLLAFTAAATATALPAS--AAKNAKLAT
```

Figure 8 (continued):

```
                      361                                                              420
            yaad    (295) ------------------------------------------------------------
         yaaD_TT1   (342) CNEVSYAGDTTEIA GP AGTLKDLLGGK----NG AKGL-G  FDK------CSRLNV-D
        yaaD_HFPI   (298) ----KFFAIAALFAA AVAQPLEDRSNGN----GN VCPP-GLFSNP-----QCCATQVL-
        yaaD_HFBII  (298) ----QFFAV-ALFAT AL--------------AA VCPT-GLFSNP-----LCCATNVL-
         HFBII_V1   (1)   -------------------------------A  VCPT-GLFSNP-----LCCATNVL-
         HFBII_V2   (1)   ---MQFFAV-ALFAT AL--------------AA VCPT-GLFSNP-----LCCATNVL-
   Hydrophbin_SC3_V2 (44) PPSTTTIAAGGTCT GSL CCNQVQSASS----SP TALLG LGI------VLSDLNVLV
   Hydrophobin_SC3_V1 (20) PPSTTTIAAGGTCT GSL CCNQVQSASS----SP TALLG LGI------VLSDLNVLV
     Hydrophobin_Gm (95)  SAAFAKQ EGTTCNV GSIA CCNSPAETNNDSLLS G LGA-G LNGLSGNTGSAC KASL- 421                                          473
            yaad    (295) -----------------------------------------------------
         yaaD_TT1   (389) L  G SSLINQECKQHIA CC GNEA DSSNDL GLN PC ALG H--------
        yaaD_HFPI   (343) G IG DCKVPSQNVYD TDFR NVC AKTGAQP C-C APVA GQAL CQTAVGA-
        yaaD_HFBII  (331) D I VDCK PTIAVD  AI F AHC ASKGSKP C-C APVA DQAL CQK IGTF
         HFBII_V1   (20)  D I VDCK PTIAVD  AI F AHC ASKGSKP C-C APVA DQAL CQK IGTF
         HFBII_V2   (35)  D I VDCK PTIAVD  AI F AHC ASKGSKP C-C APVA DQAL CQK IGTF
   Hydrophbin_SC3_V2 (94) -G SCSPL VIGVGG  CSA TV ENTQFNGLIN CTPINI --------
   Hydrophobin_SC3_V1 (70) -G SCSPL VIGVGG  CSA TV ENTQFNGLIN CTPINI --------
     Hydrophobin_Gm (153) --DQLGLLALVDHTKE PVCKNIVACCPEGTTN  -  D AGAGTKAEG--
```

Figure 9:

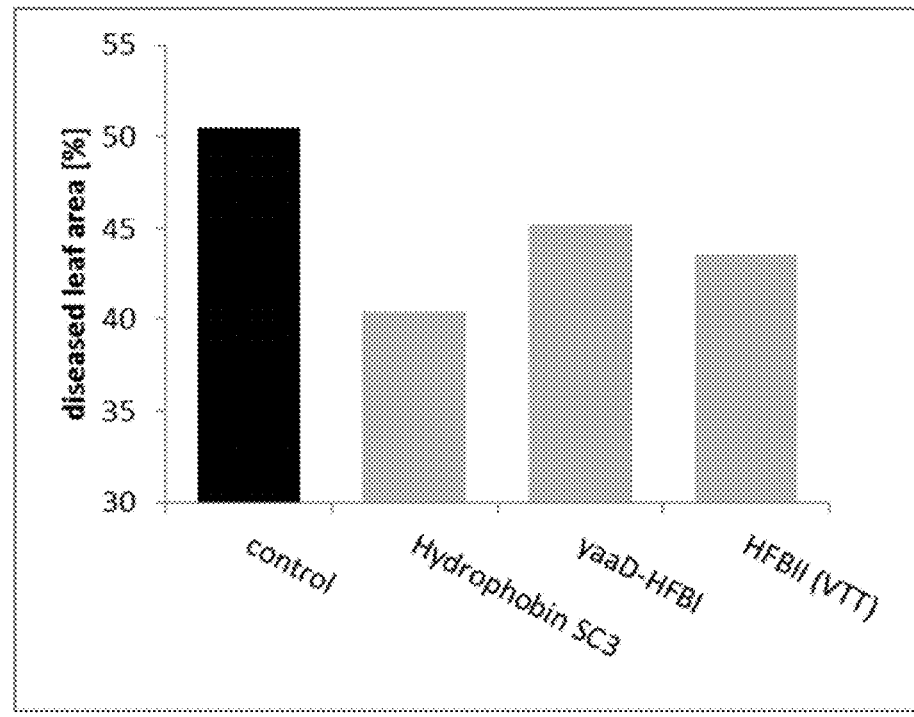

Figure 10:

| SEQ ID NO: | Description of the sequence listing |
|---|---|
| 1 | Nucleotide sequence; coding sequence hydrophobin from Aspergillus nidulans dewA; Aspergillus nidulans |
| 2 | Amino acid sequence; Hydrophobin protein dewA; Aspergillus nidulans |
| 3 | Nucleotide sequence; coding sequence for hydrophobin rodA |
| 4 | Amino acid sequence; Hydrophobin rodA protein |
| 5 | Nucleotide sequence; coding sequence for hydrophobin HypA |
| 6 | Amino acid sequence; Hydrophobin HypA protein |
| 7 | Nucleotide sequence; coding sequence for hydrophobin HypB |
| 8 | Amino acid sequence; Hydrophobin HypB protein |
| 9 | Nucleotide sequence; coding sequence for hydrophobin Sc3 |
| 10 | Amino acid sequence; Hydrophobin Sc3 protein |
| 11 | Nucleotide sequence; coding sequence for hydrophobin BASF1 |
| 12 | Amino acid sequence; Hydrophobin BASF1 protein |
| 13 | Nucleotide sequence; coding sequence for hydrophobin BASF2 |
| 14 | Amino acid sequence; Hydrophobin BASF2 protein |
| 15 | Nucleotide sequence; coding sequence synthase subunit Pdx1 (Yaad); Bacillus subtilis |
| 16 | Amino acid sequence; synthase subunit Pdx1 (Yaad); Bacillus subtilis |
| 17 | Nucleotide sequence; coding sequence for fusion partner yaad |
| 18 | Amino acid sequence; fusion partner yaad |
| 19 | Nucleotide sequence; coding sequence for fusion partner yaae |
| 20 | Amino acid sequence; fusion partner yaae |
| 21 | Nucleotide sequence; coding sequence for thioredoxin; Escherichia coli |
| 22 | Amino acid sequence; thioredoxin; Escherichia coli |

Figure 10 continued:

| 23 | Nucleotide sequence; coding sequence secretion signal |
|----|---|
| 24 | Amino acid sequence; secretion signal |
| 25 | Nucleotide sequence; coding sequence His Tag |
| 26 | Amino acid sequence; His Tag |
| 27 | Nucleotide sequence; Coding sequence for fusion protein secretion signal, synthase subunit Pdx1 (39aa) (yaad), Xa protease site, and hydrophobin (dewA) |
| 28 | Amino acid sequence; Fusion protein secretion signal, synthase subunit Pdx1 (39aa) (yaad), Xa protease site, and hydrophobin (dewA) |
| 29 | Nucleotide sequence; Coding sequence for fusion protein with secretion signal, synthase subunit Pdx1 (39aa), Xa protease site, hydrophobin, his-tag |
| 30 | Amino acid sequence; Fusion protein with secretion signal, synthase subunit Pdx1 (39aa), Xa protease site, hydrophobin, his-tag |
| 31 | Nucleotide sequence; Coding sequence for fusion protein yaad, Xa, dewA, his tag |
| 32 | Amino acid sequence; Fusion protein yaad, Xa, dewA, his tag |
| 33 | Nucleotide sequence; Coding sequence for fusion protein yaad, Xa, rodA, his tag |
| 34 | Amino acid sequence; Fusion protein yaad, Xa, rodA, his tag |
| 35 | Nucleotide sequence; Coding sequence for fusion protein yaad, Xa, BASF1, his tag |
| 36 | Amino acid sequence; Fusion protein yaad, Xa, BASF1, his tag |
| 37 | Glyma02g47670 promoter sequence; Glycine max |
| 38 | Potato cathepsin D inhibitor gene (CATHD) terminator; Solanum tuberosum |
| 39 | Nucleotide sequence; Hydrophobin_Gm-His |
| 40 | Amino acid sequence; Hydrophobin_Gm-His |

Figure 10 continued:

| 41 | Nucleotide sequence; Hydrophobin_Gm |
|---|---|
| 42 | Amino acid sequence; Hydrophobin_Gm-protein |
| 43 | Amino acid sequence; Hydrophobin SC3; version 1 |
| 44 | Amino acid sequence; Hydrophobin SC3; version 2 |
| 45 | Amino acid sequence; Hydrophobin HFBII; version 1 |
| 46 | Amino acid sequence; Hydrophobin HFBII; version 2 |
| 47 | Nucleotide sequence; Coding sequence for fusion protein yaaD_HFBII |
| 48 | Amino acid sequence; fusion protein yaaD_HFBII |
| 49 | Nucleotide sequence; Coding sequence of fusion protein yaad-HFPI |
| 50 | Amino acid sequence; fusion protein yaad-HFPI |
| 51 | Nucleotide sequence; coding sequence of fusion protein yaaD_TT1 |
| 52 | Amino acid sequence; fusion protein yaaD_TT1 |
| 53 | Amino acid sequence; Fusion partner human ubiquitin |
| 54 | Amino acid sequence; Fusion partner human thioredoxin |
| 55 | Nucleotide sequence hydrophobin variant 1 |
| 56 | Nucleotide sequence Hydrophobin variant 2 |
| 57 | Nucleotide sequence Hydrophobin variant 3 |
| 58 | Nucleotide sequence Hydrophobin, variant 4 |
| 59 | Nucleotide sequence Hydrophobin, variant 5 |
| 60 | Nucleotide sequence Hydrophobin, variant 6 |
| 61 | Nucleotide sequence Hydrophobin, variant 7 |
| 62 | Nucleotide sequence Hydrophobin, variant 8 |
| 63 | Nucleotide sequence Hydrophobin fusion protein, variant 1 |
| 64 | Nucleotide sequence Hydrophobin fusion protein, variant 2 |
| 65 | Nucleotide sequence Hydrophobin fusion protein, variant 3 |

Figure 10 continued:

| 66 | Nucleotide sequence Hydrophobin fusion protein, variant 4 |
|----|---|
| 67 | Nucleotide sequence Hydrophobin fusion protein, variant 5 |
| 68 | Nucleotide sequence Hydrophobin fusion protein, variant 6 |
| 69 | Nucleotide sequence Hydrophobin fusion protein, variant 7 |
| 70 | Nucleotide sequence Hydrophobin fusion protein, variant 8 |
| 71 | Nucleotide sequence Hydrophobin fusion protein, variant 9 |
| 72 | Amino acid sequence Hydrophobin fusion protein, variant 9 |
| 73 | Nucleotide sequence Hydrophobin fusion protein, variant 10 |
| 74 | Amino acid sequence Hydrophobin fusion protein, variant 10 |
| 75 | Nucleotide sequence Hydrophobin fusion protein, variant 11 |
| 76 | Amino acid sequence Hydrophobin fusion protein, variant 11 |
| 77 | Nucleotide sequence Hydrophobin fusion protein, variant 12 |
| 78 | Amino acid sequence Hydrophobin fusion protein, variant 12 |
| 79 | Nucleotide sequence Hydrophobin fusion protein, variant 13 |
| 80 | Amino acid sequence Hydrophobin fusion protein, variant 13 |
| 81 | Nucleotide sequence Hydrophobin fusion protein, variant 14 |
| 82 | Amino acid sequence Hydrophobin fusion protein, variant 14 |
| 83 | Nucleotide sequence Hydrophobin fusion protein, variant 15 |
| 84 | Amino acid sequence Hydrophobin fusion protein, variant 15 |
| 85 | Nucleotide sequence Hydrophobin fusion protein, variant 16 |
| 86 | Amino acid sequence Hydrophobin fusion protein, variant 16 |
| 87 | Amino acid sequence Hydrophobin TT1 |
| 88 | Amino acid sequence Hydrophobin HFPI |

Figure 10 continued:

| 89 | Nucleotide sequence Hydrophobin TT1 |
|----|-------------------------------------|
| 90 | Nucleotide sequence Hydrophobin HFPI |

FUNGAL RESISTANT PLANTS EXPRESSING HYDROPHOBIN

This application is a National Stage application of International Application No. PCT/EP2013/055318, filed Mar. 15, 2013, which claims the benefit of U.S. Provisional Application No. 61/620,454, filed Apr. 5, 2012, the entire contents of which are hereby incorporated herein by reference. This application also claims priority under 35 U.S.C. § 119 to European Patent Application No. 12163267.3, filed Apr. 5, 2012, the entire contents of which are incorporated herein by reference.

REFERENCE TO SEQUENCE LISTING SUBMITTED VIA EFS-WEB

This application was filed electronically via EFS-Web and includes an electronically submitted sequence listing in .txt format. The .txt file contains a sequence listing entitled "Sequence_List.txt" created on Jun. 11, 2014, and is 118,784 bytes in size. The sequence listing contained in this .txt file is part of the specification and is hereby incorporated by reference herein in its entirety.

SUMMARY OF THE INVENTION

The present invention relates to a method of increasing resistance against fungal pathogens, in particular, pathogens of the family Phacopsoraceae, for example soybean rust, in plants, plant parts, and/or plant cells. This is achieved by increasing the expression and/or activity of a hydrophobin protein in a plant, plant part and/or plant cell in comparison to wild type plants, wild type plant parts and/or wild type plant cells or by application of a formulation or solution containing a hydrophobin protein.

Furthermore, the invention relates to transgenic plants, plant parts, and/or plant cells having an increased resistance against fungal pathogens, in particular, pathogens of the family Phacopsoraceae, for example soybean rust, and to recombinant expression vectors comprising a sequence that is identical or homologous to a sequence encoding a hydrophobin protein.

Furthermore the invention relates to the formulation and application of hydrophobin proteins to plants, plant part and/or plant cells to modify the surface in a way that leads to decreased pathogen infection.

BACKGROUND OF THE INVENTION

The cultivation of agricultural crop plants serves mainly for the production of foodstuffs for humans and animals. Monocultures in particular, which are the rule nowadays, are highly susceptible to an epidemic-like spreading of diseases. The result is markedly reduced yields. To date, the pathogenic organisms have been controlled mainly by using pesticides. Nowadays, the possibility of directly modifying the genetic disposition of a plant or pathogen is also open to man.

Resistance generally describes the ability of a plant to prevent, or at least curtail the infestation and colonization by a harmful pathogen. Different mechanisms can be discerned in the naturally occurring resistance, with which the plants fend off colonization by phytopathogenic organisms. These specific interactions between the pathogen and the host determine the course of infection (Schopfer and Brennicke (1999) Pflanzenphysiologie, Springer Verlag, Berlin-Heidelberg, Germany).

With regard to the race specific resistance, also called host resistance, a differentiation is made between compatible and incompatible interactions. In the compatible interaction, an interaction occurs between a virulent pathogen and a susceptible plant. The pathogen survives, and may build up reproduction structures, while the host mostly dies off. An incompatible interaction occurs on the other hand when the pathogen infects the plant but is inhibited in its growth before or after weak development of symptoms. In the latter case, the plant is resistant to the respective pathogen (Schopfer and Brennicke, vide supra). However, this type of resistance is specific for a certain strain or pathogen.

In both compatible and incompatible interactions a defensive and specific reaction of the host to the pathogen occurs. In nature, however, this resistance is often overcome because of the rapid evolutionary development of new virulent races of the pathogens (Neu et al. (2003) American Cytopathol. Society, MPMI 16 No. 7: 626-633).

Most pathogens are plant-species specific. This means that a pathogen can induce a disease in a certain plant species, but not in other plant species (Heath (2002) Can. J. Plant Pathol. 24: 259-264). The resistance against a pathogen in certain plant species is called non-host resistance. The non-host resistance offers strong, broad, and permanent protection from phytopathogens. Genes providing non-host resistance provide the opportunity of a strong, broad and permanent protection against certain diseases in non-host plants. In particular, such a resistance works for different strains of the pathogen.

Fungi are distributed worldwide. Approximately 100 000 different fungal species are known to date. Thereof rusts are of great importance. They can have a complicated development cycle with up to five different spore stages (spermatium, aecidiospore, uredospore, teleutospore and basidiospore).

During the infection of plants by pathogenic fungi, different phases are usually observed. The first phases of the interaction between phytopathogenic fungi and their potential host plants are decisive for the colonization of the plant by the fungus. During the first stage of the infection, the spores become attached to the surface of the plants, germinate, and the fungus penetrates the plant. The chemical properties of the surface (e.g., cuticle) are an important determinant for the recognition of the plant as a potential host (for review see Tucker and Talbot (2001) Surface attachment and pre-penetration stage development by plant pathogenic fungi, Annual Review of Phytopathology Vol. 39: 385-417). Fungi may penetrate the plant via existing ports such as stomata, lenticels, hydatodes and wounds, or else they penetrate the plant epidermis directly as the result of the mechanical force and with the aid of cell-wall-digesting enzymes. Specific infection structures are developed for penetration of the plant. The soybean rust *Phakopsora pachyrhizi* directly penetrates the plant epidermis. After crossing the epidermal cell, the fungus reaches the intercellular space of the mesophyll, where the fungus starts to spread through the leaves. To acquire nutrients the fungus penetrates mesophyll cells and develops haustoria inside the mesophyll cell. During the penetration process the plasmamembrane of the penetrated mesophyll cell stays intact. Therefore the soybean rust fungus establishes a biotrophic interaction with soybean.

The biotrophic phytopathogenic fungi, such as many rusts, depend for their nutrition on the metabolism of living cells of the plants. This type of fungi belong to the group of biotrophic fungi, like other rust fungi, powdery mildew fungi or oomycete pathogens like the genus *Phytophthora* or

*Peronospora*. The necrotrophic phytopathogenic fungi depend for their nutrition on dead cells of the plants, e.g. species from the genus *Fusarium, Rhizoctonia* or *Mycosphaerella*. Soybean rust has occupied an intermediate position, since it penetrates the epidermis directly, whereupon the penetrated cell becomes necrotic. After the penetration, the fungus changes over to an obligatory-biotrophic lifestyle. The subgroup of the biotrophic fungal pathogens which follows essentially such an infection strategy is heminecrotrophic. In contrast to a heminecrotrophic pathogen, a hemibiotrophic pathogen lives for a short period of time in a biotrophic manner and subsequently starts killing the host cell and/or host organism, i.e., changes for the rest of its life-cycle to a necrotrophic life-style.

The early, pre-penetration stages, i.e., attachment of the spore, germination of the spore, hyphal growth and the development of the infection structure (appressorium) are crucial for the success of the infection. Unfortunately the underlying molecular mechanisms are still unknown. Nevertheless there are a few indications that the expression of hydrophobins by the fungus are required for the development of hyphae and the appressorium. For a comprehensive review about the pre-penetration stage in plant-pathogen interactions and the involvement of hydrophobins see Tucker and Talbot, "Surface attachment and pre-penetration stage development by plant pathogenic fungi (Annu. Rev. Phytopathol 2001, 39:385ff).

Hydrophobins are a class of small, cysteine-rich proteins with a length of about 100-150 amino acids which occur in nature only in filamentous fungi. They are amphiphilic and can form a layer on the surface of an object. Their natural functions include inter alia the coating of fungal spores, so that these do not stick together, the coating of aerial hyphae for reducing the surface tension of water and thus for facilitating the absorption of water, and possibly the signal transmittance between a fungus and its environment (Whiteford. J. F. Spanu, P. D. (2001), Fungal Genet. Biol. 32 (3): 159-168; Wösten et al. (1999) Current Biol. 19: 1985-88; Bell et al. (1992), Genes Dev. 6: 2382-2394).

Hydrophobins generally have eight cysteine units. They can be isolated from natural sources, but can also be obtained by means of genetic engineering methods, as described for example in WO 2006/082251 and WO 2006/131564.

The first isolation and purification of hydrophobin was carried out from *Schizophyllum commune* in 1999. In the meantime, hydrophobin genes have been identified in Ascomycetes, Deuteromycetes and Basidiomycetes. Some fungi comprise more than one hydrophobin gene, e.g. *Schizophyllum commune, Coprinus cinereus* and *Aspergillus nidulans*. On the basis of differences with regard to the hydropathy and the biophysical properties of the hydrophobins, these have been divided into two categories: class I and class II. Complementation experiments have shown that hydrophobins of the one class are able to replace hydrophobins of the other class to a certain degree as far as function is concerned. The different hydrophobins appear to be involved in different fungal development stages and to perform different functions therein (van Wetter et al. (2000) Mol. Microbiol. 36:201-210; Kershaw et al. (1998) Fungal Genet. Biol. 23:18-33).

Soybean rust has become increasingly important in recent times. The disease may be caused by the biotrophic rusts *Phakopsora pachyrhizi* (Sydow) and *Phakopsora meibomiae* (Arthur). They belong to the class Basidiomycota, order Uredinales, family Phakopsoraceae. Both rusts infect a wide spectrum of leguminosic host plants. *P. pachyrhizi*, also referred to as Asian rust, is the more aggressive pathogen on soy (*Glycine max*), and is therefore, at least currently, of great importance for agriculture. *P. pachyrhizi* can be found in nearly all tropical and subtropical soy growing regions of the world. *P. pachyrhizi* is capable of infecting 31 species from 17 families of the Leguminosae under natural conditions and is capable of growing on further 60 species under controlled conditions (Sinclair et al. (eds.), Proceedings of the rust workshop (1995), National SoyaResearch Laboratory, Publication No. 1 (1996); Rytter J. L. et al., Plant Dis. 87, 818 (1984)). *P. meibomiae* has been found in the Caribbean Basin and in Puerto Rico, and has not caused substantial damage as yet.

*P. pachyrhizi* can currently be controlled in the field only by means of fungicides. Soy plants with resistance to the entire spectrum of the isolates are not available. When searching for resistant plants, six dominant genes Rpp1-5 and Rpp?(Hyuuga), which mediate resistance of soy to *P. pachyrhizi*, were discovered. The resistance was lost rapidly, as *P. pachyrhizi* develops new virulent races.

In recent years, fungal diseases, e.g. soybean rust, has gained in importance as pest in agricultural production. There was therefore a demand in the prior art for developing methods to control fungi and to provide fungal resistant plants.

Much research has been performed on the field of powdery and downy mildew infecting the epidermal layer of plants. However, the problem to cope with soybean rust which infects the mesophyll remains unsolved.

BRIEF SUMMARY OF THE INVENTION

The object of the present invention is inter alia to provide a method of increasing resistance against fungal pathogens, preferably rust pathogens (i.e., fungal pathogens of the order Pucciniales), preferably against fungal pathogens of the family Phacopsoraceae, more preferably against fungal pathogens of the genus *Phacopsora*, most preferably against *Phakopsora pachyrhizi* (Sydow) and *Phakopsora meibomiae* (Arthur), also known as soybean rust.

Surprisingly, we found that fungal pathogens, in particular rust pathogens (i.e., fungal pathogens of the order Pucciniales), preferably fungal pathogens of the family Phacopsoraceae, for example soybean rust, can be controlled by overexpression of a hydrophobin protein. Thus, without being limited by theory, we found that fungal resistance can be achieved by expression of hydrophobin and therefore changing the physicochemical properties of the cuticle, the cell wall or the plasma membrane of the plant cell expressing the hydrophobin in a way that the fungus does not recognize its host or is inhibited by the presence of the hydrophobin. The same effect can be obtained by application of a pure or formulated hydrophobin protein solution to the plant.

The present invention therefore provides a method of increasing resistance against fungal pathogens, preferably against rust pathogens (i.e., fungal pathogens of the order Pucciniales), preferably against fungal pathogens of the family Phacopsoraceae, more preferably against fungal pathogens of the genus *Phacopsora*, most preferably against *Phakopsora pachyrhizi* (Sydow) and *Phakopsora meibomiae* (Arthur), also known as soybean rust, in transgenic plants, transgenic plant parts, or transgenic plant cells by overexpressing one or more hydrophobin nucleic acids.

In one particular embodiment, the hydrophobin is expressed as a fusion protein comprising one or more of the elements selected from the group consisting of signal sequence, fusion partner polypeptide, linker sequence, and purification sequence.

In a preferred embodiment, the hydrophobin protein is fused to a secretion signal sequence, leading to the secretion of the protein, e.g., into the apoplast and/or into the cuticle. The fusion of the hydrophobin protein to a secretion signal sequence was chosen based on the theory that a change in the hydrophobicity of the leaf surface (or of the apoplast) might inhibit the growth of the fungal hyphae or appressorium. On the other hand it is also possible that the changing of physicochemical properties of the plasma membrane of the cells expressing hydrophobin would lead to an increased resistance. Furthermore, it is possible that changing of physicochemical properties of the cytoplasm effects the degree of resistance. In the latter case, a secretion of the protein would not be required.

A further object is to provide transgenic plants resistant against fungal pathogens, preferably rust pathogens (i.e., fungal pathogens of the order Pucciniales), preferably against fungal pathogens of the family Phacopsoraceae, more preferably against fungal pathogens of the genus *Phacopsora*, most preferably against *Phakopsora pachyrhizi* (Sydow) and *Phakopsora meibomiae* (Arthur), also known as soybean rust, a method for producing such plants as well as a vector construct useful for the above methods.

Therefore, the present invention also refers to a recombinant vector construct and a transgenic plant, transgenic plant part, or transgenic plant cell comprising an exogenous hydrophobin nucleic acid. Furthermore, a method for the production of a transgenic plant, transgenic plant part or transgenic plant cell using the nucleic acid of the present invention is claimed herein. In addition, the use of a nucleic acid or the recombinant vector of the present invention for the transformation of a plant, plant part, or plant cell is claimed herein.

The objects of the present invention, as outlined above, are achieved by the subject-matter of the main claims. Preferred embodiments of the invention are defined by the subject matter of the dependent claims.

BRIEF DESCRIPTION OF THE SEVERAL VIEWS OF THE DRAWINGS

FIG. 1 shows the schematic illustration of a hydrophobin fusion protein comprising a purification sequence (e.g., a Histidine (His)-tag), a fusion partner polypeptide (e.g., part of the synthase subunit Pdx1), a linker sequence (e.g., a factor Xa protease recognition site) and a secretion signal sequence.

FIG. 2 shows the scoring system used to determine the level of diseased leaf area of wildtype and transgenic soy plants against the rust fungus *P. pachyrhizi.*

FIG. 3 shows the coding sequence of a hydrophobin fusion protein comprising a secretion signal sequence, a part of synthase subunit Pdx1 (Yaad) from *Bacillus subtilis*, factor Xa protease recognition site, hydrophobin from *Aspergillus nidulans*, and a His-tag (SEQ ID NO: 29).

FIG. 4 shows the amino acid sequence of a hydrophobin fusion protein comprising a secretion signal sequence, a part of synthase subunit Pdx1 (Yaad) from *Bacillus subtilis*, factor Xa protease recognition site, hydrophobin from *Aspergillus nidulans*, and a His-tag (SEQ ID NO: 30).

FIG. 5 shows the coding sequence of a hydrophobin fusion protein comprising a secretion signal sequence, a part of synthase subunit Pdx1 (Yaad) from *Bacillus subtilis*, factor Xa protease recognition site, and hydrophobin from *Aspergillus nidulans* without His-tag (SEQ ID NO: 27).

FIG. 6 shows the amino acid sequence of a hydrophobin fusion protein comprising a secretion signal sequence, a part of synthase subunit Pdx1 (Yaad) from *Bacillus subtilis*, factor Xa protease recognition site, and hydrophobin from *Aspergillus nidulans* without His-tag (SEQ ID NO: 28).

FIG. 7 shows the result of overexpression of hydrophobin in soybean plants, which have been infected with Asian soybean rust. The result of the scoring of 25 transgenic soy plants expressing the hydrophobin overexpression vector construct is shown. $T_0$ soybean plants expressing hydrophobin protein were inoculated with spores of *Phakopsora pachyrhizi*. The evaluation of the diseased leaf area on all leaves was performed 14 days after inoculation. The average of the percentage of the leaf area showing fungal colonies or strong yellowing/browning on all leaves was considered as diseased leaf area. At all 25 soybean $T_0$ plants expressing hydrophobin (expression checked by RT-PCR) were evaluated in parallel to non-transgenic control plants. The average of the diseased leaf area is shown in FIG. 7. Overexpression of hydrophobin significantly (*: $p<0.05$) reduces the diseased leaf area in comparison to non-transgenic control plants by 26%.

FIG. 8 shows an alignment of various Hydrophobin proteins (including their fusion partners) (Hydrophobin_Gm: SEQ ID NO: 42, HFBII version 1: SEQ ID NO: 45, HFBII version 2 (comprises additional amino acid residues for directed protein to inclusion bodies when expressed in *E. coli*): SEQ ID NO: 46, Hydrophbin_SC3 version 1: SEQ-ID NO: 43, Hydrophbin_SC3 version 2 (comprises additional amino acid residues for directed protein to inclusion bodies when expressed in *E. coli*): SEQ-ID NO: 44, yaaD_TT1: SEQ ID NO: 52, yaaD_HFPI: SEQ ID NO: 50, yaaD_HFBII: SEQ ID NO: 48, yaad: SEQ ID NO: 18).

FIG. 9 shows the result of the soybean rust disease scoring of soybean plants sprayed with the different hydrophobin varieties (10 plants each, Hydrophbin_SC3: SEQ ID NO: 43, yaaD_HFPI: SEQ ID NO: 50, HFBII: SEQ ID NO: 45) and the non-treated plants as control. Plants were inoculated with spores of *Phakopsora pachyrhizi* 24 hours after treatment with the respective Hydrophobin protein solution. The evaluation of the diseased leaf area on all leaves was performed 14 days after inoculation. The average of the percentage of the leaf area showing fungal colonies or strong yellowing/browning on all leaves was considered as diseased leaf area. At all 10 soybean plants each were sprayed with the respective hydrophobin and evaluated in parallel to non-treated control plants. The average of the diseased leaf area is shown in FIG. 9.

FIG. 10 contains a brief description of the sequences of the sequence listing.

DETAILED DESCRIPTION OF THE INVENTION

The present invention may be understood more readily by reference to the following detailed description of the preferred embodiments of the invention and the examples included herein.

Definitions

Unless otherwise noted, the terms used herein are to be understood according to conventional usage by those of ordinary skill in the relevant art. In addition to the definitions of terms provided herein, definitions of common terms in molecular biology may also be found in Rieger et al., 1991 Glossary of genetics: classical and molecular, 5th Ed., Berlin: Springer-Verlag; and in Current Protocols in Molecular Biology, F. M. Ausubel et al., Eds., Current Protocols, a joint venture between Greene Publishing Associates, Inc. and John Wiley & Sons, Inc., (1998 Supplement).

It is to be understood that as used in the specification and in the claims, "a" or "an" can mean one or more, depending upon the context in which it is used. Thus, for example, reference to "a cell" can mean that at least one cell can be utilized. It is to be understood that the terminology used herein is for the purpose of describing specific embodiments only and is not intended to be limiting.

Throughout this application, various publications are referenced. The disclosures of all of these publications and those references cited within those publications in their entireties are hereby incorporated by reference into this application in order to more fully describe the state of the art to which this invention pertains. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al., 1989 Molecular Cloning, Second Edition, Cold Spring Harbor Laboratory, Plainview, N.Y.; Maniatis et al., 1982 Molecular Cloning, Cold Spring Harbor Laboratory, Plainview, N.Y.; Wu (Ed.) 1993 Meth. Enzymol. 218, Part I; Wu (Ed.) 1979 Meth Enzymol. 68; Wu et al., (Eds.) 1983 Meth. Enzymol. 100 and 101; Grossman and Moldave (Eds.) 1980 Meth. Enzymol. 65; Miller (Ed.) 1972 Experiments in Molecular Genetics, Cold Spring Harbor Laboratory, Cold Spring Harbor, N.Y.; Old and Primrose, 1981 Principles of Gene Manipulation, University of California Press, Berkeley; Schleif and Wensink, 1982 Practical Methods in Molecular Biology; Glover (Ed.) 1985 DNA Cloning Vol. I and II, IRL Press, Oxford, UK; Hames and Higgins (Eds.) 1985 Nucleic Acid Hybridization, IRL Press, Oxford, UK; and Setlow and Hollaender 1979 Genetic Engineering: Principles and Methods, Vols. 1-4, Plenum Press, New York. Abbreviations and nomenclature, where employed, are deemed standard in the field and commonly used in professional journals such as those cited herein.

"Homologues" of a protein encompass peptides, oligopeptides, polypeptides, proteins and/or enzymes having amino acid substitutions, deletions and/or insertions relative to the unmodified protein in question and having similar functional activity as the unmodified protein from which they are derived.

"Homologues" of a nucleic acid encompass nucleotides and/or polynucleotides having nucleic acid substitutions, deletions and/or insertions relative to the unmodified nucleic acid in question, wherein the protein coded by such nucleic acids has similar or higher functional activity as the unmodified protein coded by the unmodified nucleic acid from which they are derived. In particular, homologues of a nucleic acid may encompass substitutions on the basis of the degenerative amino acid code.

A "deletion" refers to removal of one or more amino acids from a protein or to the removal of one or more nucleic acids from DNA, ssRNA and/or dsRNA.

An "insertion" refers to one or more amino acid residues or nucleic acid residues being introduced into a predetermined site in a protein or the nucleic acid.

A "substitution" refers to replacement of amino acids of the protein with other amino acids having similar properties (such as similar hydrophobicity, hydrophilicity, antigenicity, propensity to form or break α-helical structures or beta-sheet structures).

On the nucleic acid level a substitution refers to a replacement of nucleic acid with other nucleic acids, wherein the protein coded by the modified nucleic acid has a similar function. In particular homologues of a nucleic acid encompass substitutions on the basis of the degenerative amino acid code.

Amino acid substitutions are typically of single residues, but may be clustered depending upon functional constraints placed upon the protein and may range from 1 to 10 amino acids; insertions or deletion will usually be of the order of about 1 to 10 amino acid residues. The amino acid substitutions are preferably conservative amino acid substitutions. Conservative substitution tables are well known in the art (see for example Creighton (1984) Proteins. W.H. Freeman and Company (Eds) and Table 1 below, or Taylor W. R. (1986) The classification of amino acid conservation J Theor Biol., 119:205-18).

TABLE 1

Examples of conserved amino acid substitutions

| Residue | Conservative Substitutions |
|---------|---------------------------|
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

Amino acid substitutions, deletions and/or insertions may readily be made using peptide synthetic techniques well known in the art, such as solid phase peptide synthesis and the like, or by recombinant DNA manipulation.

Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gene in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

Orthologues and paralogues encompass evolutionary concepts used to describe the ancestral relationships of genes. Paralogues are genes within the same species that have originated through duplication of an ancestral gene; orthologues are genes from different organisms that have originated through speciation, and are also derived from a common ancestral gene.

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein.

Specialist databases exist for the identification of domains, for example, SMART (Schultz et al. (1998) Proc. Natl. Acad. Sci. USA 95, 5857-5864; Letunic et al. (2002) Nucleic Acids Res 30, 242-244), InterPro (Mulder et al., (2003) Nucl. Acids. Res. 31, 315-318), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp53-61, AAAI Press, Menlo Park; Hulo et al., Nucl. Acids. Res. 32:D134-D137, (2004)), or Pfam (Bateman et al., Nucleic Acids Research 30(1): 276-280 (2002)). A set of tools for in sllico analysis of protein sequences is available on the ExPASy proteomics server (Swiss Institute of Bioinformatics (Gasteiger et al., ExPASy: the proteomics server for in-depth protein knowledge and analysis, Nucleic Acids Res. 31:3784-3788(2003)). Domains or motifs may also be identified using routine techniques, such as by sequence alignment.

Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The BLAST algorithm (Altschul et al. (1990) J Mol Biol 215: 403-10) calculates percent sequence identity or similarity or homology and performs a statistical analysis of the identity or similarity or homology between the two sequences. The software for performing BLAST analysis is publicly available through the National Centre for Biotechnology Information (NCBI). Homologues may readily be identified using, for example, the ClustalW multiple sequence alignment algorithm (version 1.83), with the default pairwise alignment parameters, and a scoring method in percentage. Global percentages of similarity/homology/identity may also be determined using one of the methods available in the MatGAT software package (Campanella et al., BMC Bioinformatics. 2003 Jul. 10; 4:29. MatGAT: an application that generates similarity/homology/identity matrices using protein or DNA sequences.). Minor manual editing may be performed to optimise alignment between conserved motifs, as would be apparent to a person skilled in the art. Furthermore, instead of using full-length sequences for the identification of homologues, specific domains may also be used. The sequence identity values may be determined over the entire nucleic acid or amino acid sequence or over selected domains or conserved motif(s), using the programs mentioned above using the default parameters. For local alignments, the Smith-Waterman algorithm is particularly useful (Smith T F, Waterman M S (1981) J. Mol. Biol 147(1); 195-7).

A "signal sequence" is a short (3-60 amino acids long) peptide that directs the transport of a protein, preferably to other organelles within the cell or to certain subcellular locations or for the secretion of a protein. Signal sequences may also be called transit peptide, transit sequence, signal peptide, targeting signal, or localization signal.

A "secretion signal sequence" is particular type of signal sequence, which directs the transport of a protein to the outside of the protoplast or symplast.

The "protoplast" or "symplast" of a plant or a plant cell as understood herein is the inner space surrounded by the cellular membrane. Thus, "protoplast" or "symplast" does not include the cellular membrane.

The "apoplast" of a plant is the space outside the cellular membrane.

The "cuticule" of a plant cell or plant organ, like leave or stem, is a protective, hydrophobic, waxy covering produced by the epidermal cells.

As used herein the terms "fungal-resistance", "resistant to a fungus" and/or "fungal-resistant" mean reducing, preventing, or delaying an infection by fungi. The term "resistance" refers to fungal resistance. Resistance does not imply that the plant necessarily has 100% resistance to infection. In preferred embodiments, enhancing or increasing fungal resistance means that resistance in a resistant plant is greater than 10%, greater than 20%, greater than 30%, greater than 40%, greater than 50%, greater than 60%, greater than 70%, greater than 80%, greater than 90%, or greater than 95% in comparison to a wild type plant.

As used herein the terms "soybean rust-resistance", "resistant to a soybean rust", "soybean rust-resistant", "rust-resistance", "resistant to a rust", or "rust-resistant" mean reducing or preventing or delaying an infection of a plant, plant part, or plant cell by Phacopsoraceae, in particular *Phakopsora pachyrhizi* (Sydow) and *Phakopsora meibomiae* (Arthur)—also known as soybean rust or Asian Soybean Rust (ASR), as compared to a wild type plant, wild type plant part, or wild type plant cell. Resistance does not imply that the plant necessarily has 100% resistance to infection. In preferred embodiments, enhancing or increasing rust resistance means that rust resistance in a resistant plant is greater than 10%, greater than 20%, greater than 30%, greater than 40%, greater than 50%, greater than 60%, greater than 70%, greater than 80%, greater than 90%, or greater than 95% in comparison to a wild type plant that is not resistant to soybean rust. Preferably the wild type plant is a plant of a similar, more preferably identical, genotype as the plant having increased resistance to the soybean rust, but does not comprise an exogenous hydrophobin nucleic acid, functional fragments thereof and/or an exogenous nucleic acid capable of hybridizing with an hydrophobin nucleic acid.

The level of fungal resistance of a plant can be determined in various ways, e.g. by scoring/measuring the infected leaf area in relation to the overall leaf area. Another possibility to determine the level of resistance is to count the number of soybean rust colonies on the plant or to measure the amount of spores produced by these colonies. Another way to resolve the degree of fungal infestation is to specifically measure the amount of rust DNA by quantitative (q) PCR. Specific probes and primer sequences for most fungal pathogens are available in the literature (Frederick R D, Snyder C L, Peterson G L, et al. 2002 Polymerase chain reaction assays for the detection and discrimination of the rust pathogens *Phakopsora pachyrhizi* and *P. meibomiae*, Phytopathology 92(2) 217-227).

The term "hybridization" as used herein includes "any process by which a strand of nucleic acid molecule joins with a complementary strand through base pairing" (J. Coombs (1994) Dictionary of Biotechnology, Stockton Press, New York). Hybridization and the strength of hybridization (i.e., the strength of the association between the nucleic acid molecules) is impacted by such factors as the degree of complementarity between the nucleic acid molecules, stringency of the conditions involved, the Tm of the formed hybrid, and the G:C ratio within the nucleic acid molecules.

As used herein, the term "Tm" is used in reference to the "melting temperature." The melting temperature is the temperature at which a population of double-stranded nucleic acid molecules becomes half dissociated into single strands. The equation for calculating the Tm of nucleic acid molecules is well known in the art. As indicated by standard references, a simple estimate of the Tm value may be calculated by the equation: $Tm=81.5+0.41(\% G+C)$, when a nucleic acid molecule is in aqueous solution at 1 M NaCl (see e.g., Anderson and Young, Quantitative Filter Hybridization, in Nucleic Acid Hybridization (1985). Other references include more sophisticated computations, which take structural as well as sequence characteristics into account for the calculation of Tm. Stringent conditions, are known to those skilled in the art and can be found in Current Protocols in Molecular Biology, John Wiley & Sons, N.Y. (1989), 6.3.1-6.3.6.

In particular, the term "stringency conditions" refers to conditions, wherein 100 contiguous nucleotides or more, 150 contiguous nucleotides or more, 200 contiguous nucleotides or more or 250 contiguous nucleotides or more which are a fragment or identical to the complementary nucleic acid molecule (DNA, RNA, ssDNA or ssRNA) hybridizes under conditions equivalent to hybridization in 7% sodium dodecyl sulfate (SDS), 0.5 M NaPO4, 1 mM EDTA at 50° C. with washing in 2×SSC, 0.1% SDS at 50° C. or 65° C., preferably at 65° C., with a specific nucleic acid molecule (DNA; RNA, ssDNA or ss RNA). Preferably, the hybridizing conditions are equivalent to hybridization in 7% sodium dodecyl sulfate (SDS), 0.5 M NaPO4, 1 mM EDTA at 50° C. with washing in 1×SSC, 0.1% SDS at 50° C. or 65° C., preferably 65° C., more preferably the hybridizing conditions are equivalent to hybridization in 7% sodium dodecyl sulfate (SDS), 0.5 M NaPO4, 1 mM EDTA at 50° C. with washing in 0.1×SSC, 0.1% SDS at 50° C. or 65° C., preferably 65° C. Preferably, the complementary nucleotides hybridize with a fragment or the whole hydrophobin nucleic acids. Preferably, the complementary polynucleotide hybridizes with parts of the hydrophobin nucleic acids capable to provide soybean rust resistance by overexpression or downregulation, respectively. For example, typical high stringency hybridisation conditions for DNA hybrids longer than 50 nucleotides encompass hybridisation at 65° C. in 1×SSC or at 42° C. in 1×SSC and 50% formamide, followed by washing at 65° C. in 0.3×SSC. Examples of medium stringency hybridisation conditions for DNA hybrids longer than 50 nucleotides encompass hybridisation at 50° C. in 4×SSC or at 40° C. in 6×SSC and 50% formamide, followed by washing at 50° C. in 2×SSC.

"Identity" or "homology" or "similarity" between two nucleic acids sequences or amino acid sequences refers in each case over the entire length of the hydrophobin nucleic acid sequences or hydrophobin amino acid sequences. The terms "identity", "homology" and "similarity" are used herein interchangeably.

For example the identity may be calculated by means of the Vector NTI Suite 7.1 program of the company Informax (USA) employing the Clustal Method (Higgins D G, Sharp P M. Fast and sensitive multiple sequence alignments on a microcomputer. Comput Appl. Biosci. 1989 April; 5(2):151-1) with the following settings:

Multiple Alignment Parameter:
Gap opening penalty 10
Gap extension penalty 10
Gap separation penalty range 8
Gap separation penalty off
% identity for alignment delay 40
Residue specific gaps off
Hydrophilic residue gap off
Transition weighing 0
Pairwise Alignment Parameter:
FAST algorithm on
K-tuple size 1
Gap penalty 3
Window size 5
Number of best diagonals 5

Alternatively the identity may be determined according to Chenna, Ramu, Sugawara, Hideaki, Koike, Tadashi, Lopez, Rodrigo, Gibson, Toby J, Higgins, Desmond G, Thompson, Julie D. Multiple sequence alignment with the Clustal series of programs. (2003) Nucleic Acids Res 31 (13):3497-500, the web page: ebi.ac.uk/Tools/clustalw/index.html# and the following settings DNA Gap Open Penalty 15.0
DNA Gap Extension Penalty 6.66
DNA Matrix Identity
Protein Gap Open Penalty 10.0
Protein Gap Extension Penalty 0.2
Protein matrix Gonnet
Protein/DNA ENDGAP −1
Protein/DNA GAPDIST 4

All the nucleic acid sequences mentioned herein (single-stranded and double-stranded DNA and RNA sequences, for example cDNA and mRNA) can be produced in a known way by chemical synthesis from the nucleotide building blocks, e.g. by fragment condensation of individual overlapping, complementary nucleic acid building blocks of the double helix. Chemical synthesis of oligonucleotides can, for example, be performed in a known way, by the phosphoramidite method (Voet, Voet, 2nd edition, Wiley Press, New York, pages 896-897). The accumulation of synthetic oligonucleotides and filling of gaps by means of the Klenow fragment of DNA polymerase and ligation reactions as well as general cloning techniques are described in Sambrook et al. (1989), see below.

Sequence identity between the nucleic acid or protein useful according to the present invention and the hydrophobin nucleic acids or hydrophobin proteins may be optimized by sequence comparison and alignment algorithms known in the art (see Gribskov and Devereux, Sequence Analysis Primer, Stockton Press, 1991, and references cited therein) and calculating the percent difference between the nucleotide or protein sequences by, for example, the Smith-Waterman algorithm as implemented in the BESTFIT software program using default parameters (e.g., University of Wisconsin Genetic Computing Group).

The term "plant" is intended to encompass plants at any stage of maturity or development, as well as any tissues or organs (plant parts) taken or derived from any such plant unless otherwise clearly indicated by context. Plant parts include, but are not limited to, plant cells, stems, roots, flowers, ovules, stamens, seeds, leaves, embryos, meristematic regions, callus tissue, anther cultures, gametophytes, sporophytes, pollen, microspores, protoplasts, hairy root cultures, and/or the like. The present invention also includes seeds produced by the plants of the present invention. Preferably, the seeds comprise the exogenous hydrophobin nucleic acids. In one embodiment, the seeds can develop into plants with increased resistance to fungal infection as compared to a wild-type variety of the plant seed. As used herein, a "plant cell" includes, but is not limited to, a protoplast, gamete producing cell, and a cell that regenerates into a whole plant. Tissue culture of various tissues of plants and regeneration of plants therefrom is well known in the art and is widely published.

Reference herein to an "endogenous" nucleic acid and/or protein refers to the nucleic acid and/or protein in question as found in a plant in its natural form (i.e., without there being any human intervention).

The term "exogenous" nucleic acid refers to a nucleic acid that has been introduced in a plant by means of genetechnology. An "exogenous" nucleic acid can either not occur in a plant in its natural form, be different from the nucleic acid in question as found in a plant in its natural form, or can be identical to a nucleic acid found in a plant in its natural form, but integrated not within their natural genetic environment. The corresponding meaning of "exogenous" is applied in the context of protein expression. For example, a transgenic plant containing a transgene, i.e., an exogenous nucleic acid, may, when compared to the expression of the endogenous gene, encounter a substantial increase of the expression of the respective gene or protein in total. A transgenic plant according to the present invention includes an exogenous hydrophobin nucleic acid integrated at any genetic loci and optionally the plant may also include the endogenous gene within the natural genetic background.

For the purposes of the invention, "recombinant" means with regard to, for example, a nucleic acid sequence, a nucleic acid molecule, an expression cassette or a vector construct comprising any one or more hydrophobin nucleic acids, all those constructions brought about by man by gentechnological methods in which either
(a) the sequences of the hydrophobin nucleic acids or a part thereof, or
(b) genetic control sequence(s) which is operably linked with the hydrophobin nucleic acid sequence according to the invention, for example a promoter, or
(c) a) and b)
are not located in their natural genetic environment or have been modified by man by gentechnological methods. The modification may take the form of, for example, a substitution, addition, deletion, inversion or insertion of one or more nucleotide residues. The natural genetic environment is understood as meaning the natural genomic or chromosomal locus in the original plant or the presence in a genomic library or the combination with the natural promoter.

A recombinant nucleic acid may also refer to a nucleic acid in an isolated form. A recombinant nucleic acid, expression cassette or vector construct preferably comprises a natural gene and a natural promoter, a natural gene and a non-natural promoter, a non-natural gene and a natural promoter, or a non-natural gene and a non-natural promoter.

In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp.

A naturally occurring expression cassette—for example the naturally occurring combination of the natural promoter of the nucleic acid sequences with the corresponding nucleic acid sequence encoding a protein useful in the methods of the present invention, as described above—becomes a recombinant expression cassette when this expression cassette is modified by man by non-natural, synthetic ("artificial") methods such as, for example, mutagenic treatment. Suitable methods are described, for example, in U.S. Pat. No. 5,565,350, WO 00/15815 or US200405323. Furthermore, a naturally occurring expression cassette—for example the naturally occurring combination of the natural promoter of the nucleic acid sequences with the corresponding nucleic acid sequence encoding a protein useful in the methods of the present invention, as described above—becomes a recombinant expression cassette when this expression cassette is not integrated in the natural genetic environment but in a different genetic environment.

It shall further be noted that in the context of the present invention, the term "isolated nucleic acid" or "isolated protein" may in some instances be considered as a synonym for a "recombinant nucleic acid" or a "recombinant protein", respectively and refers to a nucleic acid or protein that is not located in its natural genetic environment and/or that has been modified by genetechnical methods. The isolated gene may be isolated from an organism or may be manmade, for example by chemical synthesis.

As used herein, the term "transgenic" refers to an organism, e.g., a plant, plant cell, callus, plant tissue, or plant part that exogenously contains the nucleic acid, recombinant construct, vector or expression cassette described herein or a part thereof which is preferably introduced by non-essentially biological processes, preferably by Agrobacteria transformation. The recombinant construct or a part thereof is stably integrated into a chromosome, so that it is passed on to successive generations by clonal propagation, vegetative propagation or sexual propagation. Preferred successive generations are transgenic too. Essentially biological processes may be crossing of plants and/or natural recombination.

A transgenic plant, plants cell or tissue for the purposes of the invention is thus understood as meaning that an exogenous hydrophobin nucleic acid, recombinant construct, vector or expression cassette including one or more hydrophobin nucleic acids is integrated into the genome by means of genetechnology.

Preferably, constructs or vectors or expression cassettes are not present in the genome of the original plant or are present in the genome of the transgenic plant not at their natural locus of the genome of the original plant.

A "wild type" plant, "wild type" plant part, or "wild type" plant cell means that said plant, plant part, or plant cell does not express exogenous hydrophobin nucleic acid or exogenous hydrophobin protein.

Natural locus means the location on a specific chromosome, preferably the location between certain genes, more preferably the same sequence background as in the original plant which is transformed.

Preferably, the transgenic plant, plant cell or tissue thereof expresses the hydrophobin nucleic acids, hydrophobin constructs or hydrophobin expression cassettes described herein.

The term "expression" or "gene expression" means the transcription of a specific gene or specific genes or specific genetic vector construct. The term "expression" or "gene expression" in particular means the transcription of a gene or genes or genetic vector construct into structural RNA (rRNA, tRNA), or mRNA with or without subsequent translation of the latter into a protein. The process includes transcription of DNA and processing of the resulting RNA product. The term "expression" or "gene expression" can also include the translation of the mRNA and therewith the synthesis of the encoded protein, i.e., protein expression.

The term "increased expression" or "enhanced expression" or "overexpression" or "increase of content" as used herein means any form of expression that is additional to the original wild-type expression level. For the purposes of this invention, the original wild-type expression level might also be zero (absence of expression). Absence of expression in the wild-type or control plant might be due to the absence of the respective coding sequence.

Methods for increasing expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of a nucleic acid encoding the protein of interest. For example, endogenous promoters may be altered in vivo by mutation, deletion, and/or substitution (see, Kmiec, U.S. Pat. No. 5,565,350; Zarling et al., WO9322443), or isolated promoters may be introduced into a plant cell in the proper orientation and distance from a gene of the present invention so as to control the expression of the gene.

If protein expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added to the 5' untranslated region (UTR) and/or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg (1988) Mol. Cell biol. 8: 4395-4405; Callis et al. (1987) Genes Dev 1:1183-1200). Such intron enhancement of gene expression is typically greatest when placed near the 5' end of the transcription unit. Use of the maize introns Adh1-S intron 1, 2, and 6, the Bronze-1 intron are known in the art. For general information see: The Maize Handbook, Chapter 116, Freeling and Walbot, Eds., Springer, N.Y. (1994).

The term "functional fragment" refers to any nucleic acid or protein which comprises merely a part of the fulllength nucleic acid or fulllength protein, respectively, but still provides the same function, e.g., fungal resistance, when expressed or repressed in a plant, respectively. Preferably, the fragment comprises at least 50%, at least 60%, at least 70%, at least 80%, at least 90% at least 95%, at least 98%, at least 99% of the original sequence. Preferably, the functional fragment comprises contiguous nucleic acids or amino acids as in the original nucleic acid or original protein, respectively. In one embodiment the fragment of any of the hydrophobin nucleic acids has an identity as defined above over a length of at least 20%, at least 30%, at least 50%, at least 75%, at least 90% of the nucleotides of the respective hydrophobin nucleic acid.

In cases where overexpression of nucleic acid is desired, the term "similar functional activity" or "similar function" means that any homologue and/or fragment provide fungal resistance when expressed in a plant. Preferably similar functional activity means at least 50%, at least 60%, at least 70%, at least 80%, at least 90%, at least 95%, at least 98%, at least 99% or 100% or higher fungal resistance compared with functional activity provided by the exogenous expression of the hydrophobin nucleotide sequence as defined by SEQ ID NO: 1 or the hydrophobin protein sequence as defined by SEQ ID NO: 2.

The term "increased activity" or "enhanced activity" as used herein means any protein having increased activity and which provides an increased fungal resistance compared with the wildtype plant merely expressing the respective endogenous hydrophobin nucleic acid. As far as overexpression is concerned, for the purposes of this invention, the original wild-type expression level might also be zero (absence of expression).

With respect to a vector construct and/or the recombinant nucleic acid molecules, the term "operatively linked" is intended to mean that the nucleic acid to be expressed is linked to the regulatory sequence, including promoters, terminators, enhancers and/or other expression control elements (e.g., polyadenylation signals), in a manner which allows for expression of the nucleic acid (e.g., in a host plant cell when the vector is introduced into the host plant cell). Such regulatory sequences are described, for example, in Goeddel, Gene Expression Technology: Methods in Enzymology 185, Academic Press, San Diego, Calif. (1990) and Gruber and Crosby, in: Methods in Plant Molecular Biology and Biotechnology, Eds. Glick and Thompson, Chapter 7, 89-108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the vector can depend on such factors as the choice of the host cell to be transformed, the level of expression of nucleic acid desired, and the like.

The term "introduction" or "transformation" as referred to herein encompass the transfer of an exogenous polynucleotide into a host cell, irrespective of the method used for transfer. Plant tissue capable of subsequent clonal propagation, whether by organogenesis or embryogenesis, may be transformed with a vector construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The host genome includes the nucleic acid contained in the nucleus as well as the nucleic acid contained in the plastids, e.g., chloroplasts, and/or mitochondria. The resulting transformed plant cell may then be used to regenerate a transformed plant in a manner known to persons skilled in the art.

The term "terminator" encompasses a control sequence which is a DNA sequence at the end of a transcriptional unit which signals 3' processing and polyadenylation of a primary transcript and termination of transcription. The terminator can be derived from the natural gene, from a variety of other plant genes, or from T-DNA. The terminator to be added may be derived from, for example, the nopaline synthase or octopine synthase genes, or alternatively from another plant gene, or less preferably from any other eukaryotic gene.

DETAILED DESCRIPTION

The present invention shows that increasing expression in a plant of a hydrophobin nucleic acid encoding a hydrophobin polypeptide gives plants having enhanced fungal resistance relative to control plants.

Hydrophobin Nucleic Acids

Thus, a hydrophobin nucleic acid encoding a hydrophobin protein is an embodiment of the present invention.

In one embodiment of the present invention, the hydrophobin nucleic acid encodes a class I or a class II hydrophobin, preferably, a hydrophobin selected from the group consisting of a hydrophobin from *Aspergillus nidulans* (e.g., dewA; nucleic acid sequence as shown in SEQ ID NO: 1), rodA (nucleic acid sequence as shown in SEQ ID NO: 3), hypA (nucleic acid sequence as shown in SEQ ID NO: 5), hypB (nucleic acid sequence as shown in SEQ ID NO: 7), sc3 (nucleic acid sequence as shown in SEQ ID NO: 9), basf1 (nucleic acid sequence as shown in SEQ ID NO: 11), basf2 (nucleic acid sequence as shown in SEQ ID NO: 13), hydrophobin SC3 (nucleic acid sequence encoding an amino acid sequence as shown in SEQ ID NO: 43 or 44), hydrophobin HFBII (nucleic acid sequence encoding an amino acid sequence as shown in SEQ ID NO: 45 or 46), hydrophobin Gm (nucleic acid sequence as shown in SEQ ID NO: 41), hydrophobin TT1 (nucleic acid sequence as shown in SEQ ID NO: 89), and hydrophobin HFPI (nucleic acid sequence as shown in SEQ ID NO: 90) or a functional fragment, derivative, orthologue, or paralogue thereof.

Preferably the hydrophobin nucleic acid is an isolated nucleic acid molecule comprising a nucleic acid selected from the group consisting of:

(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 1, 3, 5, 7, 9, 11, 13, 39, 41, 55-62, 89, or 90, or a functional fragment, derivative, orthologue, or paralogue thereof;

(ii) the complementary sequence of anyone of the nucleic acids of (i);

(iii) a nucleic acid encoding a hydrophobin protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 2, 4, 6, 8, 10, 12, 14, 40, 42, 43, 44, 45, 46, 87, or 88, or a functional fragment, derivative, orthologue, or paralogue thereof; preferably the hydrophobin polypeptide confers enhanced fungal resistance relative to control plants;

(iv) a nucleic acid molecule which hybridizes with a nucleic acid molecule of (i) to (iii) under high stringency hybridization conditions, and which preferably encodes a hydrophobin protein that has essentially the same biological activity as an hydrophobin protein encoded by SEQ ID NO: 2, 4, 6, 8, 10, 12, 14, 40, 42, 43, 44, 45, 46, 87, or 88; preferably the encoded hydrophobin protein confers enhanced fungal resistance relative to control plants; and (v) a nucleic acid encoding the same hydrophobin protein as the nucleic acids of (i) to (iv) above, but differing from the nucleic acids of (i) to (iv) above due to the degeneracy of the genetic code.

More preferably, the isolated hydrophobin nucleic acid comprising a nucleic acid selected from the group consisting of:

(i) a nucleic acid having in increasing order of preference at least 90%, at least 91%, at least 92%, at least 93%, at least 94%, at least 95%, at least 96%, at least 97%, at least 98%, at least 99% or at least 100% sequence identity to the nucleic acid sequence represented by SEQ ID NO: 1, 3, 5, 7, 9, 11, 13, 39, 41, 55-62, 89, or 90;

(ii) the complementary sequence of anyone of the nucleic acids of (i);

(iii) a nucleic acid encoding a hydrophobin protein having in increasing order of preference at least 90%, at least 91%, at least 92%, at least 93%, at least 94%, at least 95%, at least 96%, at least 97%, at least 98%, at least 99% or at least 100% sequence identity to the amino acid sequence represented by SEQ ID NO: 2, 4, 6, 8, 10, 12, 14, 40, 42, 43, 44, 45, 46, 87, or 88, preferably the hydrophobin polypeptide confers enhanced fungal resistance relative to control plants;

(iv) a nucleic acid molecule which hybridizes with a nucleic acid molecule of (i) to (iii) under high stringency hybridization conditions, and which preferably encodes a hydrophobin protein that has essentially the same biological activity as an hydrophobin protein encoded by SEQ ID NO: 2, 4, 6, 8, 10, 12, 14, 40, 42, 43, 44, 45, 46, 87, or 88; preferably the encoded hydrophobin protein confers enhanced fungal resistance relative to control plants; and (v) a nucleic acid encoding the same hydrophobin protein as the nucleic acids of (i) to (iv) above, but differing from the nucleic acids of (i) to (iv) above due to the degeneracy of the genetic code.

More preferably, the hydrophobin nucleic acid is an isolated nucleic acid molecule comprising a nucleic acid selected from the group consisting of:

(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 1, or a functional fragment, derivative, orthologue, or paralogue thereof;

(ii) the complementary sequence of anyone of the nucleic acids of (i);

(iii) a nucleic acid encoding a hydrophobin protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 2, or a functional fragment, derivative, orthologue, or paralogue thereof; preferably the hydrophobin polypeptide confers enhanced fungal resistance relative to control plants;

(iv) a nucleic acid molecule which hybridizes with a nucleic acid molecule of (i) to (iii) under high stringency hybridization conditions, and which preferably encodes a hydrophobin protein that has essentially the same biological activity as an hydrophobin protein encoded by SEQ ID NO: 2; preferably the encoded hydrophobin protein confers enhanced fungal resistance relative to control plants; and (v) a nucleic acid encoding the same hydrophobin protein as the nucleic acids of (i) to (iv) above, but differing from the nucleic acids of (i) to (iv) above due to the degeneracy of the genetic code.

More preferably, the isolated hydrophobin nucleic acid comprising a nucleic acid selected from the group consisting of:

(i) a nucleic acid having in increasing order of preference at least 90%, at least 91%, at least 92%, at least 93%, at least 94%, at least 95%, at least 96%, at least 97%, at least 98%, at least 99% or at least 100% sequence identity to the nucleic acid sequence represented by SEQ ID NO: 1;

(ii) the complementary sequence of anyone of the nucleic acids of (i);

(iii) a nucleic acid encoding a hydrophobin protein having in increasing order of preference at least 90%, at least 91%, at least 92%, at least 93%, at least 94%, at least 95%, at least 96%, at least 97%, at least 98%, at least 99% or at least 100% sequence identity to the amino acid sequence represented by SEQ ID NO: 2, preferably the hydrophobin polypeptide confers enhanced fungal resistance relative to control plants;

(iv) a nucleic acid molecule which hybridizes with a nucleic acid molecule of (i) to (iii) under high stringency hybridization conditions, and which preferably encodes a hydrophobin protein that has essentially the same biological activity as an hydrophobin protein encoded by SEQ ID NO: 2; preferably the encoded hydrophobin protein confers enhanced fungal resistance relative to control plants; and (v) a nucleic acid encoding the same hydrophobin protein as the nucleic acids of (i) to (iv) above, but differing from the nucleic acids of (i) to (iv) above due to the degeneracy of the genetic code.

Percentages of identity of a nucleic acid are indicated with reference to the entire nucleotide region given in a sequence specifically disclosed herein.

Preferably, the hydrophobin nucleic acid comprises at least about 250, at least about 275, at least about 300, at least about 350, at least about 375, at least about 380, at least about 390, at least about 400, at least about 410, at least about 420, at least about 430, at least about 440, at least about 450 nucleotides, at least about 460, at least about 470 nucleotides, preferably continuous nucleotides, preferably counted from the 5' or 3' end of the nucleic acid, or up to the full length of the nucleic acid sequence set out in SEQ ID NO: 1, 3, 5, 7, 9, 11, 13, 39, 41, 55-62, 89, or 90, preferably of the nucleic acid sequence set out in SEQ ID NO: 1. Preferably, a hydrophobin nucleic acid fragment has substantially the same biological activity as the nucleic acid sequence given in SEQ ID NO: 1, 3, 5, 7, 9, 11, 13, 39, 41, 55-62, 89, or 90, preferably, as SEQ ID NO: 1.

Preferably, the isolated hydrophobin nucleic acid comprises or consists of a sequence as represented in SEQ ID SEQ ID NO: 1, 3, 5, 7, 9, 11, 13, 39, 41, 55-62, 89, or 90, a complement thereof, a nucleic acid encoding a hydrophobin protein with SEQ ID NO: 2, 4, 6, 8, 10, 12, 14, 40, 42, 43, 44, 45, 46, 87, or 88, or a nucleic acid molecule which hybridizes with anyone of these nucleic acid molecules or a complementary sequence (complement) thereof under high stringency hybridization conditions.

Most preferably, the isolated hydrophobin nucleic acid comprises or consists of a sequence as represented in SEQ ID NO: 1, a complement thereof, a nucleic acid encoding a hydrophobin protein with SEQ ID NO: 2, or a nucleic acid molecule which hybridizes with anyone of these nucleic acid molecules or a complementary sequence (complement) thereof under high stringency hybridization conditions.

Hydrophobin Proteins

Another embodiment of the present invention is a hydrophobin protein.

In one embodiment of the present invention, the hydrophobin protein is a class I or class II hydrophobin, preferably, a hydrophobin protein selected from the group consisting of a hydrophobin from *Aspergillus nidulans* (e.g., dewA; amino acid sequence as shown in SEQ ID NO: 2), rodA (amino acid sequence as shown in SEQ ID NO: 4), hypA (amino acid sequence as shown in SEQ ID NO: 6), hypB (amino acid sequence as shown in SEQ ID NO: 8), sc3 (amino acid sequence as shown in SEQ ID NO: 10), basf1 (amino acid sequence as shown in SEQ ID NO: 12), basf2 (amino acid sequence as shown in SEQ ID NO: 14), hydrophobin SC3 (amino acid sequence as shown in SEQ ID NO: 43 or 44), hydrophobin HFBII (amino acid sequence as shown in SEQ ID NO: 45 or 46), hydrophobin Gm (amino acid sequence as shown in SEQ ID NO: 42), hydrophobin TT1 (amino acid sequence as shown in SEQ ID NO: 87), and hydrophobin HFPI (amino acid sequence as shown in SEQ ID NO: 88) or a functional fragment, derivative, orthologue, or paralogue thereof.

Preferably, the hydrophobin protein is a protein comprising an amino acid sequence selected from the group consisting of:

(i) an amino acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 2, 4, 6, 8, 10, 12, 14, 40, 42, 43, 44, 45, 46, 87, or 88, or a functional fragment, derivative, orthologue, or paralogue thereof; preferably the hydrophobin protein confers enhanced fungal resistance relative to control plants; or (ii) amino acid sequence encoded by a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 1, 3, 5, 7, 9, 11, 13, 39, 41, 55-62, 89, or 90, or a functional fragment, derivative, orthologue, or paralogue thereof; preferably the hydrophobin protein confers enhanced fungal resistance relative to control plants.

Preferably, the hydrophobin protein of the present invention is characterized by its property to enlarge at room temperature the contact angle of a drop of water on a glass surface coated with the hydrophobin protein to at least 20°, preferably at least 25°, more preferably at least 30°, compared to the contact angle of the drop of water on the glass surface not coated with the hydrophobin protein.

Preferably, the hydrophobin protein is a protein comprising an amino acid sequence selected from the group consisting of:
(i) an amino acid sequence having in increasing order of preference at least 90%, at least 91%, at least 92%, at least 93%, at least 94%, at least 95%, at least 96%, at least 97%, at least 98%, at least 99% or at least 100% sequence identity to the amino acid sequence represented by SEQ ID NO: 2, 4, 6, 8, 10, 12, 14, 40, 42, 43, 44, 45, 46, 87, or 88, or a functional fragment, derivative, orthologue, or paralogue thereof; preferably the hydrophobin protein confers enhanced fungal resistance relative to control plants; or
(ii) amino acid sequence encoded by a nucleic acid having in increasing order of preference at least 90%, at least 91%, at least 92%, at least 93%, at least 94%, at least 95%, at least 96%, at least 97%, at least 98%, at least 99% or at least 100% sequence identity to the nucleic acid sequence represented by SEQ ID NO: 1, 3, 5, 7, 9, 11, 13, 39, 41, 55-62, 89, or 90, or a functional fragment, derivative, orthologue, or paralogue thereof; preferably the hydrophobin protein confers enhanced fungal resistance relative to control plants.

Preferably, the hydrophobin protein is a protein comprising an amino acid sequence selected from the group consisting of:
(i) an amino acid sequence having in increasing order of preference at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to the amino acid sequence represented by SEQ ID NO: 2, or a functional fragment, derivative, orthologue, or paralogue thereof; preferably the hydrophobin protein confers enhanced fungal resistance relative to control plants; or
(ii) amino acid sequence encoded by a nucleic acid having in increasing order of preference at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to the nucleic acid sequence represented by SEQ ID NO: 1, or a functional fragment, derivative, orthologue, or paralogue thereof; preferably the hydrophobin protein confers enhanced fungal resistance relative to control plants.

Preferably, the hydrophobin protein is a protein comprising an amino acid sequence selected from the group consisting of:
(i) an amino acid sequence having in increasing order of preference at least 90%, at least 91%, at least 92%, at least 93%, at least 94%, at least 95%, at least 96%, at least 97%, at least 98%, at least 99% or at least 100% sequence identity to the amino acid sequence represented by SEQ ID NO: 2, or a functional fragment, derivative, orthologue, or paralogue thereof; preferably the hydrophobin protein confers enhanced fungal resistance relative to control plants; or
(ii) amino acid sequence encoded by a nucleic acid having in increasing order of preference at least 90%, at least 91%, at least 92%, at least 93%, at least 94%, at least 95%, at least 96%, at least 97%, at least 98%, at least 99% or at least 100% sequence identity to the nucleic acid sequence represented by SEQ ID NO: 1, or a functional fragment, derivative, orthologue, or paralogue thereof; preferably the hydrophobin protein confers enhanced fungal resistance relative to control plants.

Percentages of identity of an amino acid sequence or protein are indicated with reference to the entire amino acid sequence specifically disclosed herein.

Preferably, the hydrophobin protein comprises at least about 50, at least about 60, at least about 70, at least about 80, at least about 90, at least about 100, at least about 110, at least about 120, at least about 125, at least about 130, at least about 135, at least about 140, at least about 145, at least about 150, at least about 155 amino acid residues, preferably continuous amino acid residues, preferably counted from the N-terminus or the C-terminus of the amino acid sequence, or up to the full length of the amino acid sequence set out in SEQ ID NO: 2, 4, 6, 8, 10, 12, 14, 40, 42, 43, 44, 45, 46, 87, or 88, preferably of the amino acid sequence set out in SEQ ID NO: 2. Preferably, a hydrophobin protein fragment has substantially the same biological activity as the amino acid sequence given in SEQ ID NO: 2, 4, 6, 8, 10, 12, 14, 40, 42, 43, 44, 45, 46, 87, or 88, preferably, as SEQ ID NO: 2.

Preferably, the isolated hydrophobin protein comprises or consists of an amino acid sequence as represented in SEQ ID NO: 2, 4, 6, 8, 10, 12, 14, 40, 42, 43, 44, 45, 46, 87, or 88, or is encoded by a nucleic acid with a sequence as shown in SEQ ID NO: 1, 3, 5, 7, 9, 11, 13, 39, 41, 55-62, 89, or 90.

Preferably, the isolated hydrophobin protein comprises or consists of an amino acid sequence as represented in SEQ ID NO: 2, or is encoded by a nucleic acid with a sequence as shown in SEQ ID NO: 1.

Nucleic Acids Coding for a Hydrophobin Fusion Protein and Hydrophobin Fusion Proteins Another embodiment of the present invention is a nucleic acid coding for a hydrophobin fusion protein, i.e., a hydrophobin fusion protein nucleic acid. A further embodiment of the present invention is also a hydrophobin fusion protein.

A hydrophobin fusion protein can comprise one or more of the following elements: a) signal sequence, b) fusion partner polypeptide, c) hydrophobin protein, d) linker sequences, and e) purification sequence. Preferably, the fusion protein comprises one or more (1, 2, 3, 4, or 5) of the selected element, e.g., two fusion partner polypeptides.

Thus, the hydrophobin protein can be comprised in a hydrophobin fusion protein together with one or more of the following elements:

a) signal sequence, b) fusion partner polypeptide, c) linker sequences, and d) purification sequence.

In one embodiment, the hydrophobin fusion protein comprises a fusion partner and a hydrophobin protein. Optionally, the hydrophobin fusion protein further comprises a signal sequence, preferably a secretion signal sequence, and optionally a linker sequence and optionally a purification sequence.

In one embodiment, the hydrophobin fusion protein comprises a secretion signal sequence and a hydrophobin protein. Optionally, the hydrophobin fusion protein further comprises a fusion partner and optionally a linker sequence and optionally a purification sequence.

Preferably, the hydrophobin fusion protein comprises a secretion signal sequence, a fusion partner, and a hydrophobin protein. Optionally, the hydrophobin fusion protein further comprises a linker sequence and optionally a purification sequence.

Preferably, the hydrophobin fusion protein comprises a secretion signal sequence, a fusion partner, a linker sequence and a hydrophobin protein. Optionally, the hydrophobin fusion protein further comprises a purification sequence.

Signal Sequence

Preferably, the fusion protein comprises a signal sequence. A signal sequence is a short (3-60 amino acids long) peptide that directs the transport of a protein, preferably to other organelles within the cell or to certain subcellular locations or for the secretion of a protein.

The signal sequence encoded by the signal sequence nucleic acid is preferably about 5, 10, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or more amino acids long. Preferably the signal sequence is cleaved from the rest of the fusion protein, preferably by a signal peptidase, after the protein is transported. In another embodiment, the signal sequence is not cleaved from the rest of the fusion protein after the protein is transported.

Preferably, the signal sequence directs the transport of the protein to other organelles within the cell. Preferably, the signal sequence targets the hydrophobin peptide to the nucleus, mitochondria, mitochondrial matrix, endoplasmic reticulum, plastid, chloroplast, apicoplast, chromoplast, cyanelle, thylakoid, amyloplast, peroxisome, glyoxysome, and/or hydrogenosome. Preferably, the signal sequence directs the transport of the protein to the inclusion bodies of a prokaryotic cell like *E. coli*.

Most preferably, the signal sequence is a secretion signal sequence. Preferably, the secretion signal sequence directs the transport of a hydrophobin protein or hydrophobin fusion protein to the outside of the protoplast or symplast. More preferably, the secretion signal sequence directs the transport of a hydrophobin protein into the apoplast, preferably into or onto the cell wall. In one embodiment the secretion signal sequence directs the transport of a hydrophobin protein into or onto the cellular membrane. In another embodiment the secretion signal sequence directs the transport of a hydrophobin protein to the cell surface, preferably the outer surface of the cellular membrane. Most preferably, the secretion signal sequence directs the transport of a hydrophobin protein to the leave or stem surface, preferably into or onto the cuticle.

Preferably, the secretion signal sequence comprises an amino acid sequence selected from the group consisting of:
(i) an amino acid sequence having in increasing order of preference at least 60%, at least 70%, at least 80%, at least 85%, at least 90%, at least 91%, at least 92%, at least 93%, at least 94%, at least 95%, at least 96%, at least 97%, at least 98%, at least 99% or at least 100% sequence identity to the amino acid sequence represented by SEQ ID NO: 24, or a functional fragment, derivative, orthologue, or paralogue thereof; preferably the secretion signal sequence directs transport of the hydrophobin protein outside of the protoplast or symplast; or
(ii) amino acid sequence encoded by a nucleic acid having in increasing order of preference at least 60%, at least 70%, at least 80%, at least 85%, at least 90%, at least 91%, at least 92%, at least 93%, at least 94%, at least 95%, at least 96%, at least 97%, at least 98%, at least 99% or at least 100% sequence identity to the nucleic acid sequence represented by SEQ ID NO: 23, or a functional fragment, derivative, orthologue, or paralogue thereof; preferably the secretion signal sequence directs transport of the hydrophobin protein outside of the protoplast or symplast.

Preferably, the hydrophobin protein comprises at least about 10, at least about 11, at least about 12, at least about 13, at least about 14, at least about 15, at least about 16, at least about 17, at least about 18, at least about 19 amino acid residues, preferably continuous amino acid residues, preferably counted from the N-terminus or the C-terminus of the amino acid sequence, or up to the full length of the amino acid sequence set out in SEQ ID NO: 24. Preferably, a secretion signal sequence fragment has substantially the same biological activity as the amino acid sequence given in SEQ ID NO: 24.

Preferably, the secretion signal sequence comprises or consists of an amino acid sequence as represented in SEQ ID NO: 24.

Preferably, a nucleic acid encoding a secretion signal sequence is a nucleic acid selected from the group consisting of:
(i) a nucleic acid having in increasing order of preference at least 60%, at least 70%, at least 80%, at least 90%, at least 91%, at least 92%, at least 93%, at least 94%, at least 95%, at least 96%, at least 97%, at least 98%, at least 99% or at least 100% sequence identity to the nucleic acid sequence represented by SEQ ID NO: 23,
(ii) the complementary sequence of anyone of the nucleic acids of (i);
(iii) a nucleic acid encoding a hydrophobin fusion protein having in increasing order of preference at least 60%, at least 70%, at least 80%, at least 90%, at least 91%, at least 92%, at least 93%, at least 94%, at least 95%, at least 96%, at least 97%, at least 98%, at least 99% or at least 100% sequence identity to the amino acid sequence represented by SEQ ID NO: 24, preferably the secretion signal sequence directs transport of the hydrophobin protein outside of the protoplast or symplast;
(iv) a nucleic acid molecule which hybridizes with a nucleic acid molecule of (i) to (iii) under high stringency hybridization conditions; and
(v) a nucleic acid encoding the same secretion signal sequence as the nucleic acids of (i) to (iv) above, but differing from the nucleic acids of (i) to (iv) above due to the degeneracy of the genetic code.

Preferably, the nucleic acid encoding a secretion signal sequence comprises at least about 20, at least about 30, at least about 40, at least about 50, at least about 55, nucleotides, preferably continuous nucleotides, preferably counted from the 5' or 3' end of the nucleic acid or up to the full length of the nucleic acid sequence set out in SEQ ID NO: 23. Preferably, fragment of a nucleic acid encoding a secretion signal sequence has substantially the same biological activity as the nucleic acid sequence given in SEQ ID NO: 23.

Preferably, the nucleic acid encoding a secretion signal sequence comprises or consists of a sequence as represented in SEQ ID NO: 23.

Preferably, the signal sequence comprises an amino acid sequence as displayed by the additional amino acid residues of version 2 of HFBII or SC3 as shown in FIG. 8 (compared to version 1 of the respective amino acid sequence).

Alternative suitable signal sequences are known to the person skilled in the art and can be found, for instance, in Khar Heng Choo, Tin Wee Tan and Shoba Ranganathan (2005) SPdb—a signal peptide database.BMC Bioinformatics 2005, 6:249 doi:10.1186/1471-2105-6-249 and proline.bic.nus.edu.sq/spdb/.

Fusion Partner Polypeptides

Preferably, the hydrophobin protein of the hydrophobin fusion protein is linked to a polypeptide sequence with at least 10, at least 20, at least 50, at least 60, at least 70, at least 80, at least 90, at least 100, at least 150, at least 200, at least 250, at least 300 amino acid residues not naturally linked to the hydrophobin protein (herein called "fusion partner polypeptide").

Preferably, the fusion partner polypeptide is linked to the C-terminus and/or the N-terminus of the hydrophobin protein, preferably, to the N-terminus. Linkage of the fusion partner to the hydrophobin can be directly via a peptide bond or via a linker sequence, preferably a linker peptide. Preferably, the fusion protein comprises one or more, preferably 1, 2, 3, 4, or 5, fusion partner polypeptides.

Preferred fusion partner polypeptides comprised in the hydrophobin fusion protein are selected from the group of the synthase subunit Pdx1 (yaad) of Plp synthase from *Bacillus subitilis* (coding nucleic acid sequence: SEQ ID NO: 17 and amino acid sequence: 18), yaae (coding nucleic acid sequence: SEQ ID NO: 19 and amino acid sequence: 20), thioredoxin, preferably thioredoxin from *Escherichia coli* (coding nucleic acid sequence: SEQ ID NO: 21 and amino acid sequence: 22) or *Homo sapiens* (cf. SEQ ID NO: 54), and ubiquitin (e.g from *Homo sapiens* as set out in SEQ ID NO: 53), or a fragment, derivative, orthologue, or paralogue thereof.

Preferably, the hydrophobin fusion protein nucleic acid encodes a hydrophobin protein, preferably a class I hydrophobin, more preferably, a hydrophobin selected from the group consisting of dewA (SEQ ID NO: 2), rodA (SEQ ID NO: 4), hypA (SEQ ID NO: 6), hypB (SEQ ID NO: 8), sc3 (SEQ ID NO: 10), basf1 (SEQ ID NO: 12), basf2 (SEQ ID NO: 14), hydrophobin SC3 (SEQ ID NO: 43 or 44), hydrophobin HFBII (SEQ ID NO: 45 or 46), hydrophobin Gm (SEQ ID NO: 42), hydrophobin TT1 (SEQ ID NO: 87), and hydrophobin HFPI (SEQ ID NO: 88) or a functional fragment, derivative, orthologue, or paralogue thereof, fused to a fusion partner polypeptide selected from the group consisting of yaad (SEQ ID NO: 18), yaae (SEQ ID NO: 20), thioredoxin, preferably thioredoxin from *Escherichia coli* (SEQ ID NO: 22) or *Homo sapiens* (SEQ ID NO: 54), and ubiquitin (SEQ ID NO: 53) or a fragment, derivative, orthologue, or paralogue thereof. Preferred is a hydrophobin fusion protein comprising a hydrophobin from *Aspergillus nidulans* (e.g., dewA, SEQ ID NO: 2) and a fusion partner polypeptide selected from the group consisting of yaad (SEQ ID NO: 18), yaae (SEQ ID NO: 20), thioredoxin, preferably thioredoxin from *Escherichia coli* (SEQ ID NO: 22) or *Homo sapiens* (SEQ ID NO: 54), and ubiquitin (SEQ ID NO: 53), or a fragment, derivative, orthologue, or paralogue thereof, preferably a hydrophobin fusion protein comprising dewA (SEQ ID NO: 2) and yaad (SEQ ID NO: 18), or a fragment, derivative, orthologue, or paralogue thereof. Preferred fragments of yaad are the first N-terminal 10-15, 15-20, 20-25, 25-30, 30-35, 35-40, or 40-45 amino acids of SEQ ID NO: 18. Most preferred is a fragment of yaad as represented by SEQ ID NO: 16.

Preferably, the fusion partner polypeptide is encoded by a nucleic acid selected from the group consisting of:
(i) a nucleic acid having in increasing order of preference at least 60%, at least 70%, at least 80%, at least 90%, at least 91%, at least 92%, at least 93%, at least 94%, at least 95%, at least 96%, at least 97%, at least 98%, at least 99% or at least 100% sequence identity to the nucleic acid sequence represented by SEQ ID NO: 15, 17, 19 or 21;
(ii) the complementary sequence of anyone of the nucleic acids of (i);
(iii) a nucleic acid encoding a fusion partner polypeptide having in increasing order of preference at least 60%, at least 70%, at least 80%, at least 90%, at least 91%, at least 92%, at least 93%, at least 94%, at least 95%, at least 96%, at least 97%, at least 98%, at least 99% or at least 100% sequence identity to the amino acid sequence represented by SEQ ID NO: 16, 18, 20, 22, 53, or 54;
(iv) a nucleic acid molecule which hybridizes with a nucleic acid molecule of (i) to (iii) under high stringency hybridization conditions; and
(v) a nucleic acid encoding the same fusion partner polypeptide as the nucleic acids of (i) to (iv) above, but differing from the nucleic acids of (i) to (iv) above due to the degeneracy of the genetic code.

Preferably, the fusion partner polypeptide is encoded by a nucleic acid selected from the group consisting of:
(i) a nucleic acid having in increasing order of preference at least 60%, at least 70%, at least 80%, at least 90%, at least 91%, at least 92%, at least 93%, at least 94%, at least 95%, at least 96%, at least 97%, at least 98%, at least 99% or at least 100% sequence identity to the nucleic acid sequence represented by SEQ ID NO: 17;
(ii) the complementary sequence of anyone of the nucleic acids of (i);
(iii) a nucleic acid encoding a fusion partner polypeptide having in increasing order of preference at least 60%, at least 70%, at least 80%, at least 90%, at least 91%, at least 92%, at least 93%, at least 94%, at least 95%, at least 96%, at least 97%, at least 98%, at least 99% or at least 100% sequence identity to the amino acid sequence represented by SEQ ID NO: 18; and
(iv) a nucleic acid molecule which hybridizes with a nucleic acid molecule of (i) to (iii) under high stringency hybridization conditions.

Preferably, the fusion partner polypeptide is encoded by a nucleic acid selected from the group consisting of:
(i) a nucleic acid having in increasing order of preference at least 60%, at least 70%, at least 80%, at least 90%, at least 91%, at least 92%, at least 93%, at least 94%, at least 95%, at least 96%, at least 97%, at least 98%, at least 99% or at least 100% sequence identity to the nucleic acid sequence represented by SEQ ID NO: 15;
(ii) the complementary sequence of anyone of the nucleic acids of (i);
(iii) a nucleic acid encoding a fusion partner polypeptide having in increasing order of preference at least 60%, at least 70%, at least 80%, at least 90%, at least 91%, at least 92%, at least 93%, at least 94%, at least 95%, at least 96%, at least 97%, at least 98%, at least 99% or at least 100% sequence identity to the amino acid sequence represented by SEQ ID NO: 16; and
(iv) a nucleic acid molecule which hybridizes with a nucleic acid molecule of (i) to (iii) under high stringency hybridization conditions; and
(v) a nucleic acid encoding the same fusion partner polypeptide as the nucleic acids of (i) to (iv) above, but differing from the nucleic acids of (i) to (iv) above due to the degeneracy of the genetic code.

Preferably, the fusion partner polypeptide is encoded by a nucleic acid selected from the group consisting of:
(i) a nucleic acid having in increasing order of preference at least 90%, at least 91%, at least 92%, at least 93%, at least 94%, at least 95%, at least 96%, at least 97%, at least 98%, at least 99% or at least 100% sequence identity to the nucleic acid sequence represented by SEQ ID NO: 15, 17, 19 or 21;
(ii) the complementary sequence of anyone of the nucleic acids of (i);
(iii) a nucleic acid encoding a fusion partner polypeptide having in increasing order of preference at least 90%, at least 91%, at least 92%, at least 93%, at least 94%, at least 95%, at least 96%, at least 97%, at least 98%, at least 99% or at least 100% sequence identity to the amino acid sequence represented by SEQ ID NO: 16, 18, 20, 22, 53, or 54;
(iv) a nucleic acid molecule which hybridizes with a nucleic acid molecule of (i) to (iii) under high stringency hybridization conditions; and
(v) a nucleic acid encoding the same fusion partner polypeptide as the nucleic acids of (i) to (iv) above, but differing from the nucleic acids of (i) to (iv) above due to the degeneracy of the genetic code.

Preferably, the fusion partner polypeptide is encoded by a nucleic acid selected from the group consisting of:
(i) a nucleic acid having in increasing order of preference at least 90%, at least 91%, at least 92%, at least 93%, at least 94%, at least 95%, at least 96%, at least 97%, at least 98%, at least 99% or at least 100% sequence identity to the nucleic acid sequence represented by SEQ ID NO: 15;
(ii) the complementary sequence of anyone of the nucleic acids of (i);
(iii) a nucleic acid encoding a fusion partner polypeptide having in increasing order of preference at least 90%, at least 91%, at least 92%, at least 93%, at least 94%, at least 95%, at least 96%, at least 97%, at least 98%, at least 99% or at least 100% sequence identity to the amino acid sequence represented by SEQ ID NO: 16;
(iv) a nucleic acid molecule which hybridizes with a nucleic acid molecule of (i) to (iii) under high stringency hybridization conditions; and
(v) a nucleic acid encoding the same fusion partner polypeptide as the nucleic acids of (i) to (iv) above, but differing from the nucleic acids of (i) to (iv) above due to the degeneracy of the genetic code.

Preferred fragments of the fusion partner polypeptide, preferably of yaad, yaae, thioredoxin or thioredoxin, are at least 10, at least 20, at least 30, at least 40, at least 50, at least 60, or at least 70 of the first N-terminal amino acids or of the last C-terminal amino acids. Preferred are the first 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, or 320 N-terminal amino acids or the last 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, or 320 C-terminal amino acids of yaad, yaae, thioredoxin, or ubiquitin. Preferred fragments of yaad, yaae, thioredoxin or ubiquitin are the first N-terminal or the last C-terminal 10-15, 15-20, 20-25, 25-30, 30-35, 35-40, 40-45, 45-50, 50-55, 55-60, 60-65, 65-70, 70-75, 75-80, 80-85, 85-90, 90-95, or 95-100 amino acids of yaad, yaae, thioredoxin, or ubiquitin.

Preferred fragments of the fusion partner polypeptide are at least 10, at least 15, at least 20, at least 25, at least 30, at least 35, or at least 40 of the first N-terminal amino acids or the first 10, 11, 12, 13, 14, 15, 16, 17. 18, 19, 20, 21, 22, 23, 24, 25, 26, 27, 28, 19, 30, 31, 32, 33, 34, 35, 36, 37, 38, 39, or 40 N-terminal amino acids of yaad, yaae, or thioredoxin. Preferred fragments of yaad, yaae, thioredoxin, or ubiquitin are the first N-terminal 10-15, 15-20, 20-25, 25-30, 30-35, 35-40, or 40-45 amino acids of yaad, yaae, thioredoxin or ubiquitin.

Preferred fragments of the fusion partner polypeptide are at least 10, at least 15, at least 20, at least 25, at least 30, at least 35, or at least 40 of the first N-terminal amino acids or the first 10, 11, 12, 13, 14, 15, 16, 17. 18, 19, 20, 21, 22, 23, 24, 25, 26, 27, 28, 19, 30, 31, 32, 33, 34, 35, 36, 37, 38, 39, or 40 N-terminal amino acids of yaad. Preferred fragments of yaad are the first N-terminal 10-15, 15-20, 20-25, 25-30, 30-35, 35-40, or 40-45 amino acids of yaad.

A preferred fusion partner polypeptide is yaad (SEQ ID NO: 18). Preferred fragments of SEQ ID NO: 18 are at least 10, at least 15, at least 20, at least 25, at least 30, at least 35, or at least 40 of the first N-terminal amino acids or the first 10, 11, 12, 13, 14, 15, 16, 17. 18, 19, 20, 21, 22, 23, 24, 25, 26, 27, 28, 19, 30, 31, 32, 33, 34, 35, 36, 37, 38, 39, or 40 N-terminal amino acids of the SEQ ID NO: 18. Preferred fragments of yaad are the first N-terminal 10-15, 15-20, 20-25, 25-30, 30-35, 35-40, or 40-45 amino acids of SEQ ID NO: 18. Most preferred are the first 39 amino acids of the synthase subunit Pdx1 (yaad) from *Bacillus subitilis* as represented by SEQ ID NO: 16.

Another embodiment of the present invention is the corresponding coding sequence of one of the above mentioned preferred fragments of the fusion partner polypeptides.

Linker Sequence

The different elements of the hydrophobin fusion protein can be directly linked via a peptide bond or can be connected via a linker sequence. Thus, the hydrophobin fusion protein preferably comprises one or more linker sequences. The linker sequence is preferably a peptide of one or more, preferably, 1, 2, 3, 4, 5, 6, 7, 8, 9, 10, 11, 12, 13, 14, 15, 16, 17, 18, 19, or 20 amino acids. The linker sequence links two polypeptide elements of the hydrophobin fusion protein via a peptide bond at its C-terminus and its N-terminus. Preferably, the linker sequence is linked via peptide bonds between the hydrophobin protein and the signal sequence and/or between the fusion partner and the hydrophobin protein. Preferably, the linker sequence is a protease cleavage site. Preferably, the linker sequence is the recognition site for factor Xa protease. Preferably, the recognition site for factor Xa protease has the amino acid sequence isoleucine, glutamic acid, glycine, arginine (given in one letter code: IEGR).

Preferably, the fusion partner is linked to the C-terminus or the N-terminus of the hydrophobin protein, preferably, the N-terminus, via a linker sequence, preferably with the linker sequence being the recognition site for factor Xa protease, preferably, having the amino acid sequence IEGR.

Purification Sequence

Preferably, the fusion protein comprises a purification sequence. The purification sequence is preferably a peptide of one or more, preferably, 1, 2, 3, 4, 5, 6, 7, 8, 9, 10, 11, 12, 13, 14, 15, 16, 17, 18, 19, or 20 amino acids, and facilitates the purification of the hydrophobin fusion protein from its cellular context. Various purification sequences are known in the art and can be for instance a histidine (His) tag, a glutathione-S-transferase (GST) tag, a streptavidin (strep) tag, a thioredoxin tag, a maltose binding protein (MBP) tag, HA tag or a FLAG tag. Preferably, the purification sequence is a His-tag, preferably the His-tag has the sequence GSH-HHHHH (cf. SEQ ID NO: 26 and the coding sequence SEQ ID NO: 27).

Hydrophobin Fusion Protein Nucleic Acids

A preferred embodiment of the present invention is a hydrophobin fusion protein nucleic acid, which encodes a hydrophobin fusion protein.

Preferably the hydrophobin fusion protein nucleic acid encoding a hydrophobin fusion protein is an isolated nucleic acid molecule comprising a nucleic acid selected from the group consisting of:

(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 47, 49, 51, 27, 29, 31, 33, 35, 47, 49, 51, 63-70, 71, 73, 75, 77, 79, 81, 83, or 85, or a functional fragment, derivative, orthologue, or paralogue thereof;

(ii) the complementary sequence of anyone of the nucleic acids of (i);

(iii) a nucleic acid encoding a hydrophobin fusion protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 48, 50, 52, 28, 30, 32, 34, 36, 48, 50, 52, 72, 74, 76, 78, 80, 82, 84, or 86, or a functional fragment, derivative, orthologue, or paralogue thereof; preferably the hydrophobin fusion protein confers enhanced fungal resistance relative to control plants;

(iv) a nucleic acid molecule which hybridizes with a nucleic acid molecule of (i) to (iii) under high stringency hybridization conditions; and (v) a nucleic acid encoding the same hydrophobin fusion protein as the nucleic acids of (i) to (iv) above, but differing from the nucleic acids of (i) to (iv) above due to the degeneracy of the genetic code.

Preferably the hydrophobin nucleic acid encoding a hydrophobin fusion protein is an isolated nucleic acid molecule comprising a nucleic acid selected from the group consisting of:

(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 27, or a functional fragment, derivative, orthologue, or paralogue thereof;

(ii) the complementary sequence of anyone of the nucleic acids of (i);

(iii) a nucleic acid encoding a hydrophobin fusion protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 28, or a functional fragment, derivative, orthologue, or paralogue thereof; preferably the hydrophobin fusion protein confers enhanced fungal resistance relative to control plants;

(iv) a nucleic acid molecule which hybridizes with a nucleic acid molecule of (i) to (iii) under high stringency hybridization conditions; and (v) a nucleic acid encoding the same hydrophobin fusion protein as the nucleic acids of (i) to (iv) above, but differing from the nucleic acids of (i) to (iv) above due to the degeneracy of the genetic code.

Preferably the hydrophobin nucleic acid encoding a hydrophobin fusion protein is an isolated nucleic acid molecule comprising a nucleic acid selected from the group consisting of:

(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 29, or a functional fragment, derivative, orthologue, or paralogue thereof;

(ii) the complementary sequence of anyone of the nucleic acids of (i);

(iii) a nucleic acid encoding a hydrophobin fusion protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 30, or a functional fragment, derivative, orthologue, or paralogue thereof; preferably the hydrophobin fusion protein confers enhanced fungal resistance relative to control plants;
(iv) a nucleic acid molecule which hybridizes with a nucleic acid molecule of (i) to (iii) under high stringency hybridization conditions; and
(v) a nucleic acid encoding the same hydrophobin fusion protein as the nucleic acids of (i) to (iv) above, but differing from the nucleic acids of (i) to (iv) above due to the degeneracy of the genetic code.

More preferably, the isolated hydrophobin fusion protein nucleic acid encoding a hydrophobin fusion protein is an isolated nucleic acid molecule comprising a nucleic acid selected from the group consisting of:
(i) a nucleic acid having in increasing order of preference at least 60%, at least 70%, at least 80%, at least 90%, at least 91%, at least 92%, at least 93%, at least 94%, at least 95%, at least 96%, at least 97%, at least 98%, at least 99% or at least 100% sequence identity to the nucleic acid sequence represented by SEQ ID NO: 47, 49, 51, 27, 29, 31, 33, 35, 63-70, 71, 73, 75, 77, 79, 81, 83, or 85,
(ii) the complementary sequence of anyone of the nucleic acids of (i);
(iii) a nucleic acid encoding a hydrophobin fusion protein having in increasing order of preference at least 60%, at least 70%, at least 80%, at least 90%, at least 91%, at least 92%, at least 93%, at least 94%, at least 95%, at least 96%, at least 97%, at least 98%, at least 99% or at least 100% sequence identity to the amino acid sequence represented by SEQ ID NO: 48, 50, 52, 28, 30, 32, 34, 36, 72, 74, 76, 78, 80, 82, 84, or 86, preferably the hydrophobin fusion protein confers enhanced fungal resistance relative to control plants;
(iv) a nucleic acid molecule which hybridizes with a nucleic acid molecule of (i) to (iii) under high stringency hybridization conditions; and
(v) a nucleic acid encoding the same hydrophobin fusion protein as the nucleic acids of (i) to (iv) above, but differing from the nucleic acids of (i) to (iv) above due to the degeneracy of the genetic code.

More preferably, the isolated hydrophobin fusion protein nucleic acid encoding a hydrophobin fusion protein is an isolated nucleic acid molecule comprising a nucleic acid selected from the group consisting of:
(i) a nucleic acid having in increasing order of preference at least 90%, at least 91%, at least 92%, at least 93%, at least 94%, at least 95%, at least 96%, at least 97%, at least 98%, at least 99% or at least 100% sequence identity to the nucleic acid sequence represented by SEQ ID NO: 27,
(ii) the complementary sequence of anyone of the nucleic acids of (i);
(iii) a nucleic acid encoding a hydrophobin fusion protein having in increasing order of preference at least 90%, at least 91%, at least 92%, at least 93%, at least 94%, at least 95%, at least 96%, at least 97%, at least 98%, at least 99% or at least 100% sequence identity to the amino acid sequence represented by SEQ ID NO: 28, preferably the hydrophobin fusion protein confers enhanced fungal resistance relative to control plants;
(iv) a nucleic acid molecule which hybridizes with a nucleic acid molecule of (i) to (iii) under high stringency hybridization conditions; and
(v) a nucleic acid encoding the same hydrophobin fusion protein as the nucleic acids of (i) to (iv) above, but differing from the nucleic acids of (i) to (iv) above due to the degeneracy of the genetic code.

More preferably, the isolated hydrophobin fusion protein nucleic acid encoding a hydrophobin fusion protein is an isolated nucleic acid molecule comprising a nucleic acid selected from the group consisting of:
(i) a nucleic acid having in increasing order of preference at least at least 90%, at least 91%, at least 92%, at least 93%, at least 94%, at least 95%, at least 96%, at least 97%, at least 98%, at least 99% or at least 100% sequence identity to the nucleic acid sequence represented by SEQ ID NO: 29,
(ii) the complementary sequence of anyone of the nucleic acids of (i);
(iii) a nucleic acid encoding a hydrophobin fusion protein having in increasing order of preference at least 90%, at least 91%, at least 92%, at least 93%, at least 94%, at least 95%, at least 96%, at least 97%, at least 98%, at least 99% or at least 100% sequence identity to the amino acid sequence represented by SEQ ID NO: 30, preferably the hydrophobin fusion protein confers enhanced fungal resistance relative to control plants;
(iv) a nucleic acid molecule which hybridizes with a nucleic acid molecule of (i) to (iii) under high stringency hybridization conditions; and
(v) a nucleic acid encoding the same hydrophobin fusion protein as the nucleic acids of (i) to (iv) above, but differing from the nucleic acids of (i) to (iv) above due to the degeneracy of the genetic code.

Preferably, the hydrophobin fusion protein nucleic acid comprises at least about 400, at least about 450, at least about 500, at least about 550, at least about 600, at least about 650, at least about 700, at least about 750, at least about 800, at least about 850, at least about 900, at least about 950, at least about 1000 nucleotides, preferably continuous nucleotides, preferably counted from the 5' or 3' end of the nucleic acid or up to the full length of the nucleic acid sequence set out in SEQ ID NO: 47, 49, 51, 27, 29, 31, 33, 35, 63-70, 71, 73, 75, 77, 79, 81, 83, or 85, preferably of the nucleic acid sequence set out in SEQ ID NO: 27 or 29. Preferably, a hydrophobin nucleic acid fragment has substantially the same biological activity as the nucleic acid sequence given in SEQ ID NO: 47, 49, 51, 27, 29, 31, 33, 35, 63-70, 71, 73, 75, 77, 79, 81, 83, or 85, preferably, as SEQ ID NO: 27 or 29.

Preferably, the isolated hydrophobin fusion protein nucleic acid comprises or consists of a sequence as represented in SEQ ID NO: 47, 49, 51, 27, 29, 31, 33, 35, 63-70, 71, 73, 75, 77, 79, 81, 83, or 85, a complement thereof, a nucleic acid encoding a hydrophobin fusion protein with SEQ ID NO: 48, 50, 52, 28, 30, 32, 34, 36, 72, 74, 76, 78, 80, 82, 84, or 86, or a nucleic acid molecule which hybridizes with anyone of these nucleic acid molecules or a complementary sequence (complement) thereof under high stringency hybridization conditions.

Most preferably, the isolated hydrophobin fusion protein nucleic acid comprises or consists of a sequence as represented in SEQ ID NO: 27, a complement thereof, a nucleic acid encoding a hydrophobin protein with SEQ ID NO: 28, or a nucleic acid molecule which hybridizes with anyone of these nucleic acid molecules or a complementary sequence (complement) thereof under high stringency hybridization conditions.

Most preferably, the isolated hydrophobin fusion protein nucleic acid comprises or consists of a sequence as represented in SEQ ID NO: 29, a complement thereof, a nucleic acid encoding a hydrophobin protein with SEQ ID NO: 30, or a nucleic acid molecule which hybridizes with anyone of these nucleic acid molecules or a complementary sequence (complement) thereof under high stringency hybridization conditions.

Hydrophobin Fusion Proteins

Preferably, the hydrophobin fusion protein is a protein comprising an amino acid sequence selected from the group consisting of:
(i) an amino acid sequence having in increasing order of preference at least at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 48, 50, 52, 28, 30, 32, 34, 36, 72, 74, 76, 78, 80, 82, 84, or 86, or a functional fragment, derivative, orthologue, or paralogue thereof; preferably the hydrophobin fusion protein confers enhanced fungal resistance relative to control plants; or
(ii) amino acid sequence encoded by a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 47, 49, 51, 27, 29, 31, 33, 35, 63-70, 71, 73, 75, 77, 79, 81, 83, or 85, or a functional fragment, derivative, orthologue, or paralogue thereof; preferably the hydrophobin fusion protein confers enhanced fungal resistance relative to control plants.

Another embodiment of the present invention is a hydrophobin fusion protein. Preferably, the hydrophobin fusion protein is a protein comprising an amino acid sequence selected from the group consisting of:
(i) an amino acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 28, or a functional fragment, derivative, orthologue, or paralogue thereof; preferably the hydrophobin fusion protein confers enhanced fungal resistance relative to control plants; or
(ii) amino acid sequence encoded by a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 27, or a functional fragment, derivative, orthologue, or paralogue thereof; preferably the hydrophobin fusion protein confers enhanced fungal resistance relative to control plants.

Another embodiment of the present invention is a hydrophobin fusion protein. Preferably, the hydrophobin fusion protein is a protein comprising an amino acid sequence selected from the group consisting of:
(i) an amino acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 30, or a functional fragment, derivative, orthologue, or paralogue thereof; preferably the hydrophobin fusion protein confers enhanced fungal resistance relative to control plants; or
(ii) amino acid sequence encoded by a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 29, or a functional fragment, derivative, orthologue, or paralogue thereof; preferably the hydrophobin fusion protein confers enhanced fungal resistance relative to control plants.

Preferably, the hydrophobin fusion protein is a protein comprising an amino acid sequence selected from the group consisting of:
(i) an amino acid sequence having in increasing order of preference at least 90%, at least 91%, at least 92%, at least 93%, at least 94%, at least 95%, at least 96%, at least 97%, at least 98%, at least 99% or at least 100% sequence identity to the amino acid sequence represented by SEQ ID NO: 48, 50, 52, 28, 30, 32, 34, 36, 72, 74, 76, 78, 80, 82, 84, or 86, or a functional fragment, derivative, orthologue, or paralogue thereof; preferably the hydrophobin fusion protein confers enhanced fungal resistance relative to control plants; or
(ii) amino acid sequence encoded by a nucleic acid having in increasing order of preference at least 90%, at least 91%, at least 92%, at least 93%, at least 94%, at least 95%, at least 96%, at least 97%, at least 98%, at least 99% or at least 100% sequence identity to the nucleic acid sequence represented by SEQ ID NO: 47, 49, 51, 27, 29, 31, 33, 35, 63-70, 71, 73, 75, 77, 79, 81, 83, or 85 or a functional fragment, derivative, orthologue, or paralogue thereof; preferably the hydrophobin fusion protein confers enhanced fungal resistance relative to control plants.

Preferably, the hydrophobin fusion protein is a protein comprising an amino acid sequence selected from the group consisting of:
(i) an amino acid sequence having in increasing order of preference at least 90%, at least 91%, at least 92%, at least 93%, at least 94%, at least 95%, at least 96%, at least 97%, at least 98%, at least 99% or at least 100% sequence identity to the amino acid sequence represented by SEQ ID NO: 28, or a functional fragment, derivative, orthologue, or paralogue thereof; preferably the hydrophobin fusion protein confers enhanced fungal resistance relative to control plants; or
(ii) amino acid sequence encoded by a nucleic acid having in increasing order of preference at least 90%, at least 91%, at least 92%, at least 93%, at least 94%, at least 95%, at least 96%, at least 97%, at least 98%, at least 99% or at least 100% sequence identity to the nucleic acid sequence represented by SEQ ID NO: 27, or a functional fragment, derivative, orthologue, or paralogue thereof; preferably the hydrophobin fusion protein confers enhanced fungal resistance relative to control plants.

Preferably, the hydrophobin fusion protein is a protein comprising an amino acid sequence selected from the group consisting of:
(i) an amino acid sequence having in increasing order of preference at least 90%, at least 91%, at least 92%, at least 93%, at least 94%, at least 95%, at least 96%, at least 97%, at least 98%, at least 99% or at least 100% sequence identity to the amino acid sequence represented by SEQ ID NO: 30, or a functional fragment, derivative, orthologue, or paralogue thereof; preferably the hydrophobin fusion protein confers enhanced fungal resistance relative to control plants; or
(ii) amino acid sequence encoded by a nucleic acid having in increasing order of preference at least 90%, at least 91%, at least 92%, at least 93%, at least 94%, at least 95%, at least 96%, at least 97%, at least 98%, at least 99% or at least 100% sequence identity to the nucleic acid sequence represented by SEQ ID NO: 29, or a functional fragment, derivative, orthologue, or paralogue thereof; preferably the hydrophobin fusion protein confers enhanced fungal resistance relative to control plants.

Preferably, the hydrophobin fusion protein comprises at least about 100, at least about 150, at least about 175, at least about 200, at least about 250, at least about 300, at least about 350, at least about 400, at least about 450, at least about 500, at least about 550, at least about 600 amino acid residues, preferably continuous amino acid residues, preferably counted from the N-terminus or the C-terminus of the amino acid sequence, or up to the full length of the amino acid sequence set out in SEQ ID NO: 48, 50, 52, 28, 30, 32, 34, 36, 72, 74, 76, 78, 80, 82, 84, or 86, preferably of the amino acid sequence set out in SEQ ID NO: 28 or 30. Preferably, a hydrophobin protein fragment has substantially the same biological activity as the amino acid sequence given in SEQ ID NO: 48, 50, 52, 28, 30, 32, 34, 36, 72, 74, 76, 78, 80, 82, 84, or 86, preferably, as SEQ ID NO: 28 or 30.

Preferably, the isolated hydrophobin fusion protein comprises or consists of an amino acid sequence as represented in SEQ ID NO: 48, 50, 52, 28, 30, 32, 34, 36, 72, 74, 76, 78, 80, 82, 84, or 86, or is encoded by a nucleic acid with a sequence as shown in SEQ ID NO: 48, 50, 52, 27, 29, 31, 33, 35, 63-70, 71, 73, 75, 77, 79, 81, 83, or 85.

Preferably, the isolated hydrophobin fusion protein comprises or consists of an amino acid sequence as represented in SEQ ID NO: 28, or is encoded by a nucleic acid with a sequence as shown in SEQ ID NO: 27.

Preferably, the isolated hydrophobin fusion protein comprises or consists of an amino acid sequence as represented in SEQ ID NO: 30, or is encoded by a nucleic acid with a sequence as shown in SEQ ID NO: 29.

Expression Constructs and Vector Constructs

The invention also provides genetic constructs, like expression constructs or expression cassettes, or vector constructs, comprising a hydrophobin nucleic acid or a hydrophobin fusion protein nucleic acid. Preferably, these genetic constructs are suitable for the introduction and/or expression in plants, plant parts or plant cells of nucleic acids encoding hydrophobin proteins or hydrophobin fusion proteins. The expression constructs may be inserted into vectors, which may be commercially available, suitable for transforming into plants or host cells and suitable for expression of the gene of interest in the transformed cells. The invention also provides use of a genetic construct as defined herein in the methods of the invention. Thus, another embodiment of the present invention is an expression construct or expression cassette comprising a hydrophobin nucleic acid or a hydrophobin fusion protein nucleic acid.

The genetic constructs of the invention may be comprised in a host cell, plant cell, seed, agricultural product or plant or plant part. Plants or host cells are transformed with a genetic construct such as a vector construct or an expression construct comprising any of the hydrophobin nucleic acids or hydrophobin fusion protein nucleic acids described above.

In one embodiment the genetic construct of the invention confers increased fungal resistance to a plant when it has been introduced into said plant, which plant expresses the nucleic acid encoding the hydrophobin protein comprised in the genetic construct. In another embodiment the genetic construct of the invention confers increased fungal resistance to a plant comprising plant cells in which the construct has been introduced, which plant cells express the nucleic acid encoding the hydrophobin protein or hydrophobin fusion protein comprised in the genetic construct.

The skilled artisan is well aware of the genetic elements that must be present in the genetic construct in order to successfully transform, select and propagate host cells containing the sequence of interest.

More specifically, the present invention provides an expression construct comprising:
(a) a hydrophobin nucleic acid encoding a hydrophobin protein or a hydrophobin fusion protein as described above;
(b) one or more control sequences capable of driving expression of the nucleic acid sequence of (a), wherein the control sequence is preferably a promoter sequence; and optionally
(c) a transcription termination sequence.

Preferably, the present invention provides an expression construct comprising:
(a) a hydrophobin fusion protein nucleic acid encoding a hydrophobin fusion protein, wherein the hydrophobin fusion protein comprises one or more elements selected from the group consisting of signal sequence, fusion partner, hydrophobin protein, linker sequence, and purification sequence, all as described above;
(b) one or more control sequences capable of driving expression of the nucleic acid sequence of (a), wherein the control sequence is preferably a promoter sequence; and optionally
(c) a transcription termination sequence.

Preferably, the hydrophobin nucleic acid or the hydrophobin fusion protein nucleic acid of the expression construct comprises a nucleic acid selected from the group consisting of:
(i) a nucleic acid having in increasing order of preference at least 80%, at least 85%, at least 90%, at least 93%, at least 94%, at least 95%, at least 96%, at least 97%, at least 98%, at least 99% or at least 100% sequence identity to the nucleic acid sequence represented by SEQ ID NO: 1, 3, 5, 7, 9, 11, 13, 39, 41, 55-62, 89, 90, 47, 49, 51, 27, 29, 31, 33, 35, 63-70, 71, 73, 75, 77, 79, 81, 83, or 85;
(ii) the complementary sequence of anyone of the nucleic acids of (i);
(iii) a nucleic acid encoding a hydrophobin protein or hydrophobin fusion protein having in increasing order of preference at least 80%, at least 85%, at least 90%, at least 93%, at least 94%, at least 95%, at least 96%, at least 97%, at least 98%, at least 99% or at least 100% sequence identity to the amino acid sequence represented by SEQ ID NO: 2, 4, 6, 8, 10, 12, 14, 40, 42, 43, 44, 45, 46, 87, 88, 48, 50, 52, 28, 30, 32, 34, 36, 72, 74, 76, 78, 80, 82, 84, or 86, preferably the hydrophobin protein or hydrophobin fusion protein confers enhanced fungal resistance relative to control plants;
(iv) a nucleic acid molecule which hybridizes with a nucleic acid molecule of (i) to (iii) under high stringency hybridization conditions; and
(v) a nucleic acid encoding the same protein as the nucleic acids of (i) to (iv) above, but differing from the nucleic acids of (i) to (iv) above due to the degeneracy of the genetic code.

Most preferably, the hydrophobin nucleic acid or hydrophobin fusion protein nucleic acid of the expression construct has SEQ ID NO: 1, 3, 27, or 29, a complement thereof, a nucleic acid encoding a hydrophobin protein or hydrophobin fusion protein with SEQ ID NO: 2, 4, 28, 30, or a nucleic acid molecule which hybridizes with anyone of these nucleic acid molecules under high stringency hybridization conditions.

A recombinant vector construct comprising:
(a) an expression cassette, as described above, comprising a hydrophobin nucleic acid or a hydrophobin fusion protein nucleic acid, as described above, operably linked with
(b) a promoter and
(c) a transcription termination sequence is a further embodiment of the invention.

Preferably, the recombinant vector construct comprises:
(a) (i) a nucleic acid having at least 60% identity, preferably at least 70% sequence identity, at least 80%, at least 90%, at least 95%, at least 98%, at least 99% sequence identity, or even 100% sequence identity with SEQ ID NO: 1, 3, 5, 7, 9, 11, 13, 39, 41, 55-62, 89, 90, 47, 49, 51, 27, 29, 31, 33, 35, 63-70, 71, 73, 75, 77, 79, 81, 83, or 85 or a functional fragment thereof, or an orthologue or a paralogue thereof;
(ii) a nucleic acid coding for a protein having at least 60% identity, preferably at least 70% sequence identity, at least 80%, at least 90%, at least 95%, at least 98%, at least 99% sequence identity, or even 100% sequence identity with SEQ ID NO: 2, 4, 6, 8, 10, 12, 14, 40, 42, 43, 44, 45, 46, 87, 88, 48, 50, 52, 28, 30, 32, 34, 36, 72, 74, 76, 78, 80, 82, 84, or 86, a functional fragment thereof, an orthologue or a paralogue thereof;
(iii) a nucleic acid capable of hybridizing under stringent conditions with any of the nucleic acids according to (i) or (ii) or a complement thereof; and/or
(iv) a nucleic acid encoding the same protein as the nucleic acids of (i) to (iii) above, but differing from the nucleic acids of (i) to (iii) above due to the degeneracy of the genetic code;
operably linked with
(b) a promoter and
(c) a transcription termination sequence.

Furthermore, a recombinant vector construct is provided comprising:
(a) (i) a nucleic acid having at least 90%, at least 95%, at least 98%, at least 99% sequence identity, or even 100% sequence identity with SEQ ID NO: 1, 3, 27, or 29;
(ii) a nucleic acid coding for a protein having at least 90%, at least 95%, at least 98%, at least 99% sequence identity, or even 100% sequence identity with SEQ ID NO: 2, 4, 28, or 30; and/or
(iii) a nucleic acid capable of hybridizing under stringent conditions with any of the nucleic acids according to (i) or (ii) or a complement thereof; and/or
(iv) a nucleic acid encoding the same protein as the nucleic acids of (i) to (iii) above, but differing from the nucleic acids of (i) to (iii) above due to the degeneracy of the genetic code;
operably linked with
(b) a promoter and
(c) a transcription termination sequence is a further embodiment of the invention.

Preferably, the transcription termination sequence is the *Solanum tuberosum* (potato) cathepsin D inhibitor gene (CATHD) terminator (SEQ ID NO: 38). Preferably, the transcription termination sequence comprises a nucleic acid having at least 70%, at least 80%, at least 90%, at least 95%, at least 98%, at least 99% sequence identity, or even 100% sequence identity with SEQ ID NO: 38 or a functional fragment thereof, or an orthologue or a paralogue thereof.

Promoters according to the present invention may be constitutive, inducible, in particular pathogen-inducible, developmental stage-preferred, cell type-preferred, tissue-preferred or organ-preferred. Constitutive promoters are active under most conditions. Non-limiting examples of constitutive promoters include the CaMV 19S and 35S promoters (Odell et al., 1985, Nature 313:810-812), the sX CaMV 35S promoter (Kay et al., 1987, Science 236:1299-1302), the Sep1 promoter, the rice actin promoter (McElroy et al., 1990, Plant Cell 2:163-171), the *Arabidopsis* actin promoter, the ubiquitin promoter (Christensen et al., 1989, Plant Molec. Biol. 18:675-689); pEmu (Last et al., 1991, Theor. Appl. Genet. 81:581-588), the figwort mosaic virus 35S promoter, the Smas promoter (Velten et al., 1984, EMBO J. 3:2723-2730), the GRP1-8 promoter, the cinnamyl alcohol dehydrogenase promoter (U.S. Pat. No. 5,683,439), promoters from the T-DNA of *Agrobacterium*, such as mannopine synthase, nopaline synthase, and octopine synthase, the small subunit of ribulose biphosphate carboxylase (ssuRUBISCO) promoter, and/or the like.

Preferably, the expression vector of the invention comprises a constitutive promoter, mesophyll-specific promoter, epidermis-specific promoter, root-specific promoter, a pathogen inducible promoter, or a fungal-inducible promoter. A promoter is inducible, if its activity, measured on the amount of RNA produced under control of the promoter, is at least 30%, at least 40%, at least 50% preferably at least 60%, at least 70%, at least 80%, at least 90% more preferred at least 100%, at least 200%, at least 300% higher in its induced state, than in its un-induced state. A promoter is cell-, tissue- or organ-specific, if its activity, measured on the amount of RNA produced under control of the promoter, is at least 30%, at least 40%, at least 50% preferably at least 60%, at least 70%, at least 80%, at least 90% more preferred at least 100%, at least 200%, at least 300% higher in a particular cell-type, tissue or organ, then in other cell-types or tissues of the same plant, preferably the other cell-types or tissues are cell types or tissues of the same plant organ, e.g. a root. In the case of organ specific promoters, the promoter activity has to be compared to the promoter activity in other plant organs, e.g. leaves, stems, flowers or seeds. Preferably, the promoter is a constitutive promoter, mesophyll-specific promoter, or epidermis-specific promoter.

Preferably, the promoter is an epidermis-specific promoter, most preferred is the Glyma02g47670 promoter (SEQ ID NO: 37). Preferably, the promoter sequence comprises a nucleic acid having at least 70%, at least 80%, at least 90%, at least 95%, at least 98%, at least 99% sequence identity, or even 100% sequence identity with SEQ ID NO: 37 or a functional fragment thereof, or an orthologue or a paralogue thereof.

In preferred embodiments, the increase in the protein amount and/or activity of the hydrophobin protein takes place in a constitutive or tissue-specific manner. In especially preferred embodiments, an essentially pathogen-induced increase in the protein amount and/or protein activity takes place, for example by recombinant expression of the hydrophobin nucleic acid under the control of a fungal-inducible promoter. In particular, the expression of the hydrophobin nucleic acid takes place on fungal infected sites, where, however, preferably the expression of the hydrophobin nucleic acid remains essentially unchanged in tissues not infected by fungus.

Developmental stage-preferred promoters are preferentially expressed at certain stages of development. Tissue and organ preferred promoters include those that are preferentially expressed in certain tissues or organs, such as leaves, roots, seeds, or xylem. Examples of tissue preferred and organ preferred promoters include, but are not limited to, fruit-preferred, ovule-preferred, male tissue-preferred, seed-preferred, integument-preferred, tuber-preferred, stalk-preferred, pericarp-preferred, leaf-preferred, stigma-preferred, pollen-preferred, anther-preferred, a petal-preferred, sepal-preferred, pedicel-preferred, silique-preferred, stem-preferred, root-preferred promoters and/or the like. Seed preferred promoters are preferentially expressed during seed development and/or germination. For example, seed preferred promoters can be embryo-preferred, endosperm preferred and seed coat-preferred. See Thompson et al., 1989, BioEssays 10:108. Examples of seed preferred promoters include, but are not limited to cellulose synthase (celA), Cim1, gamma-zein, globulin-1, maize 19 kD zein (cZ19B1) and/or the like.

Other suitable tissue-preferred or organ-preferred promoters include, but are not limited to, the napin-gene promoter from rapeseed (U.S. Pat. No. 5,608,152), the USP-promoter from *Vicia faba* (Baeumlein et al., 1991, Mol Gen Genet. 225(3):459-67), the oleosin-promoter from *Arabidopsis* (PCT Application No. WO 98/45461), the phaseolin-promoter from *Phaseolus vulgaris* (U.S. Pat. No. 5,504,200), the Bce4-promoter from *Brassica* (PCT Application No. WO 91/13980), or the legumin B4 promoter (LeB4; Baeumlein et al., 1992, Plant Journal, 2(2):233-9), as well as promoters conferring seed specific expression in monocot plants like maize, barley, wheat, rye, rice, etc. Suitable promoters to note are the Ipt2 or Ipt1-gene promoter from barley (PCT Application No. WO 95/15389 and PCT Application No. WO 95/23230) or those described in PCT Application No. WO 99/16890 (promoters from the barley hordein-gene, rice glutelin gene, rice oryzin gene, rice prolamin gene, wheat gliadin gene, wheat glutelin gene, oat glutelin gene, Sorghum kasirin-gene, and/or rye secalin gene)

Promoters useful according to the invention include, but are not limited to, are the major chlorophyll a/b binding protein promoter, histone promoters, the Ap3 promoter, the β-conglycin promoter, the napin promoter, the soybean lectin promoter, the maize 15 kD zein promoter, the 22 kD zein promoter, the 27 kD zein promoter, the g-zein promoter, the waxy, shrunken 1, shrunken 2, bronze promoters, the Zm13 promoter (U.S. Pat. No. 5,086,169), the maize polygalacturonase promoters (PG) (U.S. Pat. Nos. 5,412,085 and 5,545,546), the SGB6 promoter (U.S. Pat. No. 5,470,359), as well as synthetic or other natural promoters.

Epidermis-specific promoters may be selected from the group consisting of:
WIR5 (=GstA1); acc. X56012; Dudler & Schweizer,
GLP4, acc. AJ310534; Wei Y., Zhang Z., Andersen C. H., Schmelzer E., Gregersen P. L., Collinge D. B., Smedegaard-Petersen V. and Thordal-Christensen H., Plant Molecular Biology 36, 101 (1998),
GLP2a, acc. AJ237942, Schweizer P., Christoffel A. and Dudler R., Plant J. 20, 541 (1999);
Prx7, acc. AJ003141, Kristensen B. K., Ammitzböll H., Rasmussen S. K. and Nielsen K. A., Molecular Plant Pathology, 2(6), 311 (2001);
GerA, acc. AF250933; Wu S., Druka A., Horvath H., Kleinhofs A., Kannangara G. and von Wettstein D., Plant Phys Biochem 38, 685 (2000);
OsROC1, acc. AP004656
RTBV, acc. AAV62708, AAV62707; Klöti A., Henrich C., Bieri S., He X., Chen G., Burkhardt P. K., Wiinn J., Lucca P., Hohn T., Potrykus I. and Fütterer J., PMB 40, 249 (1999);
Chitinase ChtC2-Promoter from potato (Ancillo et al., Planta. 217(4), 566, (2003));
AtProT3 Promoter (Grallath et al., Plant Physiology. 137(1), 117 (2005));
SHN-Promoters from *Arabidopsis* (AP2/EREBP transcription factors involved in cutin and wax production) (Aarón et al., Plant Cell. 16(9), 2463 (2004)); and/or
GSTA1 from wheat (Dudler et al., WP2005306368 and Altpeter et al., Plant Molecular Biology. 57(2), 271 (2005)).

Mesophyll-specific promoters may be selected from the group consisting of:
PPCZm1 (=PEPC); Kausch A. P., Owen T. P., Zachwieja S. J., Flynn A. R. and Sheen J., Plant Mol. Biol. 45, 1 (2001);
OsrbcS, Kyozuka et al., PlaNT Phys 102, 991 (1993); Kyozuka J., McElroy D., Hayakawa T., Xie Y., Wu R. and Shimamoto K., Plant Phys. 102, 991 (1993);
OsPPDK, acc. AC099041;
TaGF-2.8, acc. M63223; Schweizer P., Christoffel A. and Dudler R., Plant J. 20, 541 (1999);
TaFBPase, acc. X53957;
TaWIS1, acc. AF467542; US 200220115849;
HvBIS1, acc. AF467539; US 200220115849;
ZmMIS1, acc. AF467514; US 200220115849;

HvPR1a, acc. X74939; Bryngelsson et al., Mol. Plant Microbe Interacti. 7 (2), 267 (1994);

HvPR1b, acc. X74940; Bryngelsson et al., Mol. Plant Microbe Interact. 7(2), 267 (1994);

HvB1,3gluc; acc. AF479647;

HvPrx8, acc. AJ276227; Kristensen et al., Molecular Plant Pathology, 2(6), 311 (2001); and/or HvPAL, acc. X97313; Wei Y., Zhang Z., Andersen C. H., Schmelzer E., Gregersen P. L., Collinge D. B., Smedegaard-Petersen V. and Thordal-Christensen H. Plant Molecular Biology 36, 101 (1998).

Constitutve promoters may be selected from the group consisting of

PcUbi promoter from parsley (WO 03/102198)

CaMV 35S promoter: Cauliflower Mosaic Virus 35S promoter (Benfey et al. 1989 EMBO J. 8(8): 2195-2202), STPT promoter: *Arabidopsis thaliana* Short Triose phosphat translocator promoter (Accession NM_123979)

Act1 promoter:—*Oryza sativa* actin 1 gene promoter (McElroy et al. 1990 PLANT CELL 2(2) 163-171 a) and/or EF1A2 promoter: *Glycine max* translation elongation factor EF1 alpha (US 20090133159).

One type of vector construct is a "plasmid," which refers to a circular double stranded DNA loop into which additional DNA segments can be ligated. Another type of vector is a viral vector, wherein additional DNA segments can be ligated into the viral genome. Certain vector constructs are capable of autonomous replication in a host plant cell into which they are introduced. Other vector constructs are integrated into the genome of a host plant cell upon introduction into the host cell, and thereby are replicated along with the host genome. In particular the vector construct is capable of directing the expression of gene to which the vectors is operatively linked. However, the invention is intended to include such other forms of expression vector constructs, such as viral vectors (e.g., potato virus X, tobacco rattle virus, and/or Gemini virus), which serve equivalent functions.

The hydrophobin expression constructs and vectors described herein are useful in the methods, plants, harvestable parts and products of the invention.

In preferred embodiments, the increase in the protein quantity or function of the hydrophobin protein takes place in a constitutive or tissue-specific manner. In especially preferred embodiments, an essentially pathogen-induced increase in the protein quantity or protein function takes place, for example by exogenous expression of the hydrophobin nucleic acid under the control of a fungal-inducible promoter. In particular, the expression of the hydrophobin nucleic acid takes place on fungal infected sites, where, however, preferably the expression of the hydrophobin nucleic acid sequence remains essentially unchanged in tissues not infected by fungus. In preferred embodiments, the protein amount of a hydrophobin protein in the plant is increased by at least 10%, at least 20%, at least 30%, at least 40%, at least 50%, at least 60%, at least 70%, at least 80%, at least 90%, or at least 95% or more in comparison to a wild type plant that is not transformed with the hydrophobin nucleic acid.

Methods for Increasing Fungal Resistance; Methods for Modulating Gene Expression The present invention also provides a method for increasing resistance to fungal pathogens, in particular fungal pathogens of the family Phacopsoraceae, preferably against fungal pathogens of the genus *Phacopsora*, most preferably against *Phakopsora pachyrhizi* (Sydow) and *Phakopsora meibomiae* (Arthur), also known as soy bean rust in plants or plant cells, wherein in comparison to wild type plants, wild type plant parts, or wild type plant cells a hydrophobin protein or a functional fragment, orthologue, paralogue or homologue thereof is increased in expression.

The present invention further provides a method for increasing resistance to fungal pathogens of the genus *Phacopsora*, most preferably against *Phakopsora pachyrhizi* (Sydow) and *Phakopsora meibomiae* (Arthur), also known as soy bean rust in plants or plant cells by increasing the expression of a hydrophobin protein.

In preferred embodiments, the protein amount and/or function of the hydrophobin protein in the plant is increased by at least 10%, at least 20%, at least 30%, at least 40%, at least 50%, at least 60%, at least 60%, at least 70%, at least 80%, at least 90%, or at least 95% or more in comparison to a wild type plant that is not transformed with the hydrophobin nucleic acid.

In one embodiment of the invention, the hydrophobin protein is encoded by (i) a nucleic acid having at least 60%, at least 70%, for example at least 75%, more preferably at least 80%, for example at least 85%, even more preferably at least 90%, for example at least 95% or at least 96% or at least 97% or at least 98% most preferably 99% identity with SEQ ID NO: 1, 3, 5, 7, 9, 11, 13, 39, 41, 55-62, 89, or 90, a functional fragment thereof, or an orthologue or a paralogue thereof;

(ii) a nucleic acid encoding a protein having at least 60% identity, at least 70%, for example at least 75%, more preferably at least 80%, for example at least 85%, even more preferably at least 90%, for example at least 95% or at least 96% or at least 97% or at least 98% most preferably 99% homology with SEQ ID NO: 2, 4, 6, 8, 10, 12, 14, 40, 42, 43, 44, 45, 46, 87, or 88, a functional fragment thereof, an orthologue or a paralogue thereof, (iii) an exogenous nucleic acid capable of hybridizing under stringent conditions with any of the nucleic acids according to (i) or (ii) or a complementary sequence (complement) thereof; and/or by (iv) a nucleic acid encoding the same protein as the nucleic acids of (i) to (iii) above, but differing from the nucleic acids of (i) to (iii) above due to the degeneracy of the genetic code.

A method for increasing fungal resistance, preferably resistance to Phacopsoraceae, for example soy bean rust, in a plant, plant part, or plant cell, by increasing the expression of a hydrophobin protein or a functional fragment, orthologue, paralogue or homologue thereof wherein the hydrophobin protein is encoded by (i) an exogenous nucleic acid having at least 80%, at least 90%, at least 95%, at least 98%, at least 99% sequence identity, or even 100% sequence identity with SEQ ID NO: 1, 3, 5, 7, 9, 11, 13, 39, 41, 55-62, 89, or 90, or a functional fragment thereof, an orthologue or a paralogue thereof;

(ii) an exogenous nucleic acid encoding a protein having at least 80%, at least 90%, at least 95%, at least 98%, at least 99% sequence identity, or even 100% sequence identity with SEQ ID NO: 2, 4, 6, 8, 10, 12, 14, 40, 42, 43, 44, 45, 46, 87, or 88, or a functional fragment thereof, an orthologue or a paralogue thereof;

(iii) an exogenous nucleic acid capable of hybridizing under stringent conditions with any of the nucleic acids according to (i) or (ii) or a complement thereof is a further embodiment of the invention; and/or by (iv) a nucleic acid encoding the same protein as the nucleic acids of (i) to (iii) above, but differing from the nucleic acids of (i) to (iii) above due to the degeneracy of the genetic code.

In the method for increasing resistance to fungal pathogens the exogenous nucleic acid encoding a hydrophobin protein can also encode a hydrophobin fusion protein comprising the hydrophobin protein and one or more elements selected from the group consisting of signal sequence, fusion partner polypeptide, linker sequence, and purification sequence.

Preferably, the hydrophobin fusion protein comprises a signal sequence, preferably, the signal sequence being a secretion signal sequence. Preferably, the secretion signal sequence is encoded by (i) an exogenous nucleic acid having at least 80% identity with SEQ ID NO: 23; or a functional fragment thereof, an orthologue or a paralogue thereof;
(ii) an exogenous nucleic acid coding for a protein having at least 80% identity with SEQ ID NO: 24; or a functional fragment thereof, an orthologue or a paralogue thereof;
(iii) an exogenous nucleic acid capable of hybridizing under stringent conditions with any of the nucleic acids according to (i) or (ii) or a complementary sequence thereof; and/or
(iv) a nucleic acid encoding the same protein as the nucleic acids of (i) to (iii) above, but differing from the nucleic acids of (i) to (iii) above due to the degeneracy of the genetic code.

In another embodiment, the hydrophobin fusion protein comprises a fusion partner polypeptide and the fusion partner polypeptide is encoded by (i) an exogenous nucleic acid having at least 60% identity with SEQ ID NO: 15, 17, 19, or 21; or a fragment thereof, an orthologue or a paralogue thereof;
(ii) an exogenous nucleic acid coding for a protein having at least 60% identity with SEQ ID NO: 16, 18, 20, 22, 53, or 54; or a fragment thereof, an orthologue or a paralogue thereof;
(iii) an exogenous nucleic acid capable of hybridizing under stringent conditions with any of the nucleic acids according to (i) or (ii) or a complementary sequence thereof; and/or
(iv) a nucleic acid encoding the same protein as the nucleic acids of (i) to (iii) above, but differing from the nucleic acids of (i) to (iii) above due to the degeneracy of the genetic code;

Thus, preferably, in the method of increasing resistance to fungal pathogens the hydrophobin fusion protein is encoded by (i) a nucleic acid having at least 60%, at least 70%, for example at least 75%, more preferably at least 80%, for example at least 85%, even more preferably at least 90%, for example at least 95% or at least 96% or at least 97% or at least 98% most preferably 99% identity with SEQ ID NO: 47, 49, 51, 27, 29, 31, 33, 35, 63-70, 71, 73, 75, 77, 79, 81, 83, or 85, a functional fragment thereof, or an orthologue or a paralogue thereof; or by
(ii) a nucleic acid encoding a protein having at least 60% identity, at least 70%, for example at least 75%, more preferably at least 80%, for example at least 85%, even more preferably at least 90%, for example at least 95% or at least 96% or at least 97% or at least 98% most preferably 99% homology with SEQ ID NO: 48, 50, 52, 28, 30, 32, 34, 36, 72, 74, 76, 78, 80, 82, 84, or 86, a functional fragment thereof, an orthologue or a paralogue thereof,
(iii) an exogenous nucleic acid capable of hybridizing under stringent conditions with any of the nucleic acids according to (i) or (ii) or a complementary sequence (complement) thereof; or by
(iv) a nucleic acid encoding the same protein as the nucleic acids of (i) to (iii) above, but differing from the nucleic acids of (i) to (iii) above due to the degeneracy of the genetic code;

In a further method of the invention, the method comprises the steps of
(a) stably transforming a plant cell with a (i) recombinant expression cassette as described herein in functional linkage with a promoter or (ii) a recombinant vector construct as described herein;
(b) regenerating the plant from the plant cell; and
(c) expressing said nucleic acid, optionally wherein the nucleic acid which codes for a hydrophobin protein is expressed in an amount and for a period sufficient to generate or to increase soybean rust resistance in said plant.

In a further method of the invention, the method comprises the steps of
(a) stably transforming a plant cell with a recombinant expression cassette comprising
  (i) a nucleic acid having at least 60% identity, at least 70% sequence identity, at least 80%, at least 90%, at least 95%, at least 98%, at least 99% sequence identity, or even 100% sequence identity with SEQ ID NO: 1, 3, 5, 7, 9, 11, 13, 39, 41, 55-62, 89, 90, 47, 49, 51, 27, 29, 31, 33, 35, 63-70, 71, 73, 75, 77, 79, 81, 83, or 85; or a functional fragment thereof, or an orthologue or a paralogue thereof;
  (ii) a nucleic acid coding for a protein having at least 60% identity, at least 70% sequence identity, at least 80%, at least 90%, at least 95%, at least 98%, at least 99% sequence identity, or even 100% sequence identity with SEQ ID NO: 2, 4, 6, 8, 10, 12, 14, 40, 42, 43, 44, 45, 46, 87, 88, 48, 50, 52, 28, 30, 32, 34, 36, 72, 74, 76, 78, 80, 82, 84, or 86, a functional fragment thereof, an orthologue or a paralogue thereof;
  (iii) a nucleic acid capable of hybridizing under stringent conditions with any of the nucleic acids according to (i) or (ii) or a complement thereof; and/or
  (iv) a nucleic acid encoding the same protein as the nucleic acids of (i) to (iii) above, but differing from the nucleic acids of (i) to (iii) above due to the degeneracy of the genetic code;
in functional linkage with a promoter;
(b) regenerating the plant from the plant cell; and
(c) expressing said nucleic acid, optionally wherein the nucleic acid which codes for a hydrophobin protein is expressed in an amount and for a period sufficient to generate or to increase soybean rust resistance in said plant.

A preferred embodiment is a method for increasing resistance to soy bean rust in a soy bean plant, soy bean plant part, or soy bean plant cell, by increasing the expression of a hydrophobin protein or hydrophobin fusion protein, wherein the hydrophobin protein or hydrophobin fusion protein is encoded by
(i) an exogenous nucleic acid having at least 90%, at least 95%, at least 98%, at least 99% sequence identity, or even 100% sequence identity with SEQ ID NO: 1, 3, 5, 7, 9, 11, 13, 39, 41, 55-62, 89, 90, 47, 49, 51, 27, 29, 31, 33, 35, 63-70, 71, 73, 75, 77, 79, 81, 83, or 85;
(ii) an exogenous nucleic acid encoding a protein having at least 90%, at least 95%, at least 98%, at least 99% sequence identity, or even 100% sequence identity with SEQ ID NO: 2, 4, 6, 8, 10, 12, 14, 40, 42, 43, 44, 45, 46, 87, 88, 48, 50, 52, 28, 30, 32, 34, 36, 72, 74, 76, 78, 80, 82, 84, or 86;

(iii) an exogenous nucleic acid capable of hybridizing under stringent conditions with any of the nucleic acids according to (i) or (ii) or a complement thereof; and/or by (iv) a nucleic acid encoding the same protein as the nucleic acids of (i) to (iii) above, but differing from the nucleic acids of (i) to (iii) above due to the degeneracy of the genetic code;

wherein increasing the expression of the hydrophobin protein is achieved by transforming the soy bean plant, plant part or plant cell with a nucleic acid comprising the nucleic acid set out under item (i), (ii), (iii), or (iv).

Also a preferred embodiment is a method for increasing resistance to soy bean rust in a soy bean plant, soy bean plant part, or soy bean plant cell, by increasing the expression of a hydrophobin protein, wherein the hydrophobin protein is encoded by (i) an exogenous nucleic acid having at least 90%, at least 95%, at least 98%, at least 99% sequence identity, or even 100% sequence identity with SEQ ID NO: 1, 3, 27, or 29; or (ii) an exogenous nucleic acid encoding a protein having at least 90%, at least 95%, at least 98%, at least 99% sequence identity, or even 100% sequence identity with SEQ ID NO: 2, 4, 28, or 30;

wherein increasing the expression of the hydrophobin protein is achieved by transforming the soy bean plant, plant part or plant cell with a nucleic acid comprising the nucleic acid set out under item (i) or (ii).

Another embodiment of the present invention is a method for applying a hydrophobin protein as described herein to a surface of a plant, plant part or plant cell. Preferred parts of the plant are leaves, stem, flower, seed, or root, or parts thereof.

The application of the hydrophobin protein to the surface of the plant, plant part or plant cell can be achieved in several ways. Preferably, the hydrophobin protein is applied to the surface of the plant by spraying a formulation or solution containing the hydrophobin protein on the surface of the plant, plant part or plant cell. Alternatively, the plant, plant part or plant cell can be dipped into the hydrophobin containing formulation or solution or can be cultured or incubated or impregnated in the hydrophobin containing solution. Furthermore, the application of the hydrophobin protein to the surface of the plant, plant part or plant cell can be achieved by means of gene technology. For instance, a transgenic plant, plant part or plant cell can be generated, which express the hydrophobin protein and excretes the hydrophobin protein (preferably, by means of a hydrophobin fusion protein as described herein) to the surface of the plant, plant part or plant cell Preferred is thus a method for applying a hydrophobin protein to a surface of a plant, plant part or plant cell, wherein the hydrophobin protein is encoded by a nucleic acid selected from the group consisting of (i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 1, 3, 5, 7, 9, 11, 13, 39, 41, 55-62, 89, or 90, or a functional fragment, derivative, orthologue, or paralogue thereof;

(ii) the complementary sequence of anyone of the nucleic acids of (i);

(iii) a nucleic acid encoding a hydrophobin protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 2, 4, 6, 8, 10, 12, 14, 40, 42, 43, 44, 45, 46, 87, or 88, or a functional fragment, derivative, orthologue, or paralogue thereof; preferably the hydrophobin polypeptide confers enhanced fungal resistance relative to control plants; and (iv) a nucleic acid molecule which hybridizes with a nucleic acid molecule of (i) to (iii) under high stringency hybridization conditions; and/or (v) a nucleic acid encoding the same protein as the nucleic acids of (i) to (iv) above, but differing from the nucleic acids of (i) to (iv) above due to the degeneracy of the genetic code.

Further preferred is a method for applying a hydrophobin protein as described herein to a surface of a plant, plant part or plant cell, wherein the hydrophobin protein comprises an amino acid sequence with at least 60% identity with SEQ ID NO: 2, 4, 6, 8, 10, 12, 14, 40, 42, 43, 44, 45, 46, 87, or 88; or a functional fragment thereof, an orthologue or a paralogue thereof.

Thus, preferred is a method for increasing fungal resistance in a plant by applying a hydrophobin protein as described herein to a surface of a plant, plant part or plant cell, preferably by spraying a formulation comprising a hydrophobin protein to the surface of the plant, plant part or plant cell.

Hence, the present invention is also directed to the use of a hydrophobin protein as described herein for applying the hydrophobin protein to a surface of a plant, a plant part, or a plant cell.

Preferably, the present invention is also directed to the use of a hydrophobin protein as described herein for increasing fungal resistance in a plant, a plant part, or a plant cell, preferably by applying the hydrophobin protein to a surface of a plant, a plant part, or a plant cell.

Thus, the present invention is also directed to a surface of a plant, plant part or plant cell coated with a hydrophobin protein as described herein.

Preferably, the hydrophobin protein is applied to the surface of a plant, plant part or plant cell in the form of a hydrophobin fusion protein as described herein, preferably with a fusion protein comprising an amino acid sequence having at least 60%, at least 70%, at least 80%, at least 85%, at least 90%, at least 92%, at least 95%, at least 97%, at least 98%, at least 99%, or even 100% sequence identity with SEQ ID NO: 32, 34, 36, 48, 80, or 52, or an amino acid sequence encoded by a nucleic acid sequence having at least 60%, at least 70%, at least 80%, at least 85%, at least 90%, at least 92%, at least 95%, at least 97%, at least 98%, at least 99%, or even 100% sequence identity with SEQ ID NO: 31, 33, 35, 47, 49, or 51.

The surface of a plant or plant part coated with a hydrophobin protein can be the surface of any plant organ. Preferably, the surface of a plant or plant part coated with a hydrophobin protein is a plant organ surface with the plant organ being selected from the group consisting of leave, stem, flower, root, and seed.

Also part of the invention is a plant, plant part or plant cell having a surface coated with a hydrophobin protein as described herein.

The formulation containing the hydrophobin preferably comprises one or more of the following: solvent, buffer, surfactant, detergent (ionic and/or non-ionic), stabilizer and preservative. Appropriate hydrophobin formulations and conditions for coating a surface with a hydrophobin protein are described in the Examples and, for instance, in WO2006/082253A2, WO2006/082251 A2 and WO2006/131564A2.

The fungal pathogens or fungus-like pathogens (such as, for example, Chromista) can belong to the group comprising Plasmodiophoramycota, Oomycota, Ascomycota, Chytridiomycetes, Zygomycetes, Basidiomycota or Deuteromycetes (Fungi imperfecti). Pathogens which may be mentioned by way of example, but not by limitation, are those detailed in Tables 2 and 3, and the diseases which are associated with them.

TABLE 2

Diseases caused by biotrophic and/or heminecrotrophic phytopathogenic fungi

| Disease | Pathogen |
|---|---|
| Leaf rust | *Puccinia recondita* |
| Yellow rust | *P. striiformis* |
| Powdery mildew | *Erysiphe graminis/Blumeria graminis* |
| Rust (common corn) | *Puccinia sorghi* |
| Rust (Southern corn) | *Puccinia polysora* |
| Tobacco leaf spot | *Cercospora nicotianae* |
| Rust (soybean) | *Phakopsora pachyrhizi*, *P. meibomiae* |
| Rust (tropical corn) | *Physopella pallescens*, *P. zeae* = *Angiopsora zeae* |

TABLE 3

Diseases caused by necrotrophic and/or hemibiotrophic fungi and Oomycetes

| Disease | Pathogen |
|---|---|
| Plume blotch | *Septoria* (*Stagonospora*) *nodorum* |
| Leaf blotch | *Septoria tritici* |
| Ear fusarioses | *Fusarium* spp. |
| Late blight | *Phytophthora infestans* |
| Anthrocnose leaf blight<br>Anthracnose stalk rot | *Colletotrichum graminicola* (teleomorph: *Glomerella graminicola* Politis); *Glomerella tucumanensis* (anamorph: *Glomerella falcatum* Went) |
| *Curvularia* leaf spot | *Curvularia clavata*, *C. eragrostidis*, = *C. maculans* (teleomorph: *Cochliobolus eragrostidis*), *Curvularia inaequalis*, C. intermedia (teleomorph: *Cochliobolus intermedius*), *Curvularia lunata* (teleomorph: *Cochliobolus lunatus*), *Curvularia pallescens* (teleomorph: *Cochliobolus pallescens*), *Curvularia senegalensis*, *C. tuberculata* (teleomorph: *Cochliobolus tuberculatus*) |
| *Didymella* leaf spot | *Didymella exitalis* |
| *Diplodia* leaf spot or streak | *Stenocarpella macrospora* = *Diplodialeaf macrospora* |
| Brown stripe downy mildew | *Sclerophthora rayssiae* var. *zeae* |
| Crazy top downy mildew | *Sclerophthora macrospora* = *Sclerospora macrospora* |
| Green ear downy mildew (*graminicola* downy mildew) | *Sclerospora graminicola* |
| Leaf spots, minor | *Alternaria alternata*, *Ascochyta maydis*, *A. tritici*, *A. zeicola*, *Bipolaris victoriae* = *Helminthosporium victoriae* (teleomorph: *Cochliobolus victoriae*), *C. sativus* (anamorph: *Bipolaris sorokiniana* = *H. sorokinianum* = *H. sativum*), *Epicoccum nigrum*, *Exserohilum prolatum* = *Drechslera prolata* (teleomorph: *Setosphaeria prolata*) *Graphium penicillioides*, *Leptosphaeria maydis*, *Leptothyrium zeae*, *Ophiosphaerella herpotricha*, (anamorph: *Scolecosporiella* sp.), *Paraphaeosphaeria michotii*, *Phoma* sp., *Septoria zeae*, *S. zeicola*, *S. zeina* |
| Northern corn leaf blight (white blast, crown stalk rot, stripe) | *Setosphaeria turcica* (anamorph: *Exserohilum turcicum* = *Helminthosporium turcicum*) |
| Northern corn leaf spot *Helminthosporium* ear rot (race 1) | *Cochliobolus carbonum* (anamorph: *Bipolaris zeicola* = *Helminthosporium carbonum*) |
| *Phaeosphaeria* leaf spot | *Phaeosphaeria maydis* = *Sphaerulina maydis* |

TABLE 3-continued

Diseases caused by necrotrophic and/or hemibiotrophic fungi and Oomycetes

| Disease | Pathogen |
|---|---|
| *Rostratum* leaf spot (*Helminthosporium* leaf disease, ear and stalk rot) | *Setosphaeria rostrata*, (anamorph: *xserohilum rostratum* = *Helminthosporium rostratum*) |
| Java downy mildew | *Peronosclerospora maydis* = *Sclerospora maydis* |
| Philippine downy mildew | *Peronosclerospora philippinensis* = *Sclerospora philippinensis* |
| *Sorghum* downy mildew | *Peronosclerospora sorghi* = *Sclerospora sorghi* |
| *Spontaneum* downy mildew | *Peronosclerospora spontanea* = *Sclerospora spontanea* |
| Sugarcane downy mildew | *Peronosclerospora sacchari* = *Sclerospora sacchari* |
| *Sclerotium* ear rot (southern blight) | *Sclerotium rolfsii* Sacc. (teleomorph: *Athelia rolfsii*) |
| Seed rot-seedling blight | *Bipolaris sorokiniana*, *B. zeicola* = *Helminthosporium carbonum*, *Diplodia maydis*, *Exserohilum pedicillatum*, *Exserohilum turcicum* = *Helminthosporium turcicum*, *Fusarium avenaceum*, *F. culmorum*, *F. moniliforme*, *Gibberella zeae* (anamorph: *F. graminearum*), *Macrophomina phaseolina*, *Penicillium* spp., *Phomopsis* sp., *Pythium* spp., *Rhizoctonia solani*, *R. zeae*, *Sclerotium rolfsii*, *Spicaria* sp. |
| *Selenophoma* leaf spot | *Selenophoma* sp. |
| Yellow leaf blight | *Ascochyta ischaemi*, *Phyllosticta maydis* (teleomorph: *Mycosphaerella zeae-maydis*) |
| Zonate leaf spot | *Gloeocercospora sorghi* |

The following are especially preferred:

Plasmodiophoromycota such as *Plasmodiophora brassicae* (clubroot of crucifers), *Spongospora subterranea*, *Polymyxa graminis*, Oomycota such as *Bremia lactucae* (downy mildew of lettuce), *Peronospora* (downy mildew) in snapdragon (*P. antirrhini*), onion (*P. destructor*), spinach (*P. effusa*), soybean (*P. manchurica*), tobacco ("blue mold"; *P. tabacina*) alfalfa and clover (*P. trifolium*), *Pseudoperonospora humuli* (downy mildew of hops), *Plasmopara* (downy mildew in grapevines) (*P. viticola*) and sunflower (*P. halstedii*), *Sclerophthora macrospora* (downy mildew in cereals and grasses), *Pythium* (for example damping-off of Beta beet caused by *P. debaryanum*), *Phytophthora infestans* (late blight in potato and in tomato and the like), *Albugo* spec.

Ascomycota such as *Microdochium nivale* (snow mold of rye and wheat), *Fusarium, Fusarium graminearum, Fusarium culmorum* (partial ear sterility mainly in wheat), *Fusarium oxysporum* (*Fusarium* wilt of tomato), *Blumeria graminis* (powdery mildew of barley (f.sp. *hordei*) and wheat (f.sp. *tritici*)), *Erysiphe pisi* (powdery mildew of pea), *Nectria galligena* (*Nectria* canker of fruit trees), *Uncinula necator* (powdery mildew of grapevine), *Pseudopeziza tracheiphila* (red fire disease of grapevine), *Claviceps purpurea* (ergot on, for example, rye and grasses), *Gaeumannomyces graminis* (take-all on wheat, rye and other grasses), *Magnaporthe grisea, Pyrenophora graminea* (leaf stripe of barley), *Pyrenophora teres* (net blotch of barley), *Pyrenophora tritici-repentis* (leaf blight of wheat), *Venturia inaequalis* (apple scab), *Sclerotinia sclerotium* (stalk break, stem rot), *Pseudopeziza medicaginis* (leaf spot of alfalfa, white and red clover).

Basidiomycetes such as *Typhula incarnata* (*typhula* blight on barley, rye, wheat), *Ustilago maydis* (blister smut on maize), *Ustilago nuda* (loose smut on barley), *Ustilago tritici* (loose smut on wheat, spelt), *Ustilago avenae* (loose smut on oats), *Rhizoctonia solani* (*rhizoctonia* root rot of potato), *Sphacelotheca* spp. (head smut of sorghum), *Melampsora lini* (rust of flax), *Puccinia graminis* (stem rust of wheat, barley, rye, oats), *Puccinia recondita* (leaf rust on wheat), *Puccinia dispersa* (brown rust on rye), *Puccinia hordei* (leaf rust of barley), *Puccinia coronata* (crown rust of oats), *Puccinia striiformis* (yellow rust of wheat, barley, rye and a large number of grasses), *Uromyces appendiculatus* (brown rust of bean), *Sclerotium rolfsii* (root and stem rots of many plants).

Deuteromycetes (Fungi imperfecti) such as *Septoria* (*Stagonospora*) *nodorum* (glume blotch) of wheat (*Septoria tritici*), *Pseudocercosporella herpotrichoides* (eyespot of wheat, barley, rye), *Rynchosporium secalis* (leaf spot on rye and barley), *Alternaria solani* (early blight of potato, tomato), *Phoma betae* (blackleg on Beta beet), *Cercospora beticola* (leaf spot on Beta beet), *Alternaria brassicae* (black spot on oilseed rape, cabbage and other crucifers), *Verticillium dahliae* (*verticillium* wilt), *Colletotrichum, Colletotrichum lindemuthianum* (bean anthracnose), *Phoma lingam* (blackleg of cabbage and oilseed rape), *Botrytis cinerea* (grey mold of grapevine, strawberry, tomato, hops and the like).

Especially preferred are biotrophic pathogens, e.g., *Phakopsora pachyrhizi* and/or those pathogens which have essentially a similar infection mechanism as *Phakopsora pachyrhizi*, as described herein. Particularly preferred are pathogens from the subclass Pucciniomycetes, preferably from the order Pucciniales (rust), previously known as Uredinales, among which in particular the Melompsoraceae. Preferred are Phakopsoraceae, more preferably *Phakopsora*. Especially preferred are *Phakopsora pachyrhizi* and/or *Phakopsora meibomiae*.

Also preferred rust fungi are selected from the group of *Puccinia, Gymnosporangium, Juniperus, Cronartium, Hemlleia,* and *Uromyces,* preferably *Puccinia sorghi, Gymnosporangium juniperi-virginianae, Juniperus virginiana, Cronartium ribicola, Hemlleia vastatrix, Puccinia graminis, Puccinia coronata, Uromyces phaseoli, Puccinia hemerocallidis, Puccinia persistens* subsp. *Triticina, Puccinia stniformis, Puccinia graminis* causes, and/or *Uromyces appendeculatus.*

Transgenic Organisms; Transgenic Plants, Plant Parts, and Plant Cells

A preferred embodiment is a transgenic plant, transgenic plant part, or transgenic plant cell overexpressing an exogenous hydrophobin protein or hydrophobin fusion protein, as described above. Preferably, the hydrophobin protein overexpressed in the plant, plant part or plant cell is encoded by (i) an exogenous nucleic acid having at least 60% identity with SEQ ID NO: 1, 3, 5, 7, 9, 11, 13, 39, 41, 55-62, 89, or 90, or a functional fragment, thereof, an orthologue or a paralogue thereof; or by (ii) an exogenous nucleic acid encoding a protein having at least 60% identity with SEQ ID NO: 2, 4, 6, 8, 10, 12, 14, 40, 42, 43, 44, 45, 46, 87, or 88, a functional fragment thereof, an orthologue or a paralogue thereof;

(iii) an exogenous nucleic acid capable of hybridizing under stringent conditions with any of the nucleic acids according to (i) or (ii) or a complement thereof. Most preferably, the exogenous nucleic acid has at least 95%, at least 98%, at least 99% sequence identity, or even 100% sequence identity with SEQ ID NO: 1; or comprises an exogenous nucleic acid encoding a protein having at least 95%, at least 98%, at least 99% sequence identity, or even 100% sequence identity with SEQ ID NO: 2; and/or by (iv) a nucleic acid encoding the same protein as the nucleic acids of (i) to (iii) above, but differing from the nucleic acids of (i) to (iii) above due to the degeneracy of the genetic code.

Preferably, the hydrophobin fusion protein overexpressed in the plant, plant part or plant cell is encoded by (i) an exogenous nucleic acid having at least 60% identity with SEQ ID NO: 47, 49, 51, 27, 29, 31, 33, 35, 63-70, 71, 73, 75, 77, 79, 81, 83, or 85, or a functional fragment, thereof, an orthologue or a paralogue thereof; or by (ii) an exogenous nucleic acid encoding a protein having at least 60% identity with SEQ ID NO: 48, 50, 52, 28, 30, 32, 34, 36, 72, 74, 76, 78, 80, 82, 84, or 86, a functional fragment thereof, an orthologue or a paralogue thereof;

(iii) an exogenous nucleic acid capable of hybridizing under stringent conditions with any of the nucleic acids according to (i) or (ii) or a complement thereof; most preferably, the exogenous nucleic acid has at least 95%, at least 98%, at least 99% sequence identity, or even 100% sequence identity with SEQ ID NO: 27 or 29; or comprises an exogenous nucleic acid encoding a protein having at least 95%, at least 98%, at least 99% sequence identity, or even 100% sequence identity with SEQ ID NO: 28 or 30; and/or by (iv) a nucleic acid encoding the same protein as the nucleic acids of (i) to (iii) above, but differing from the nucleic acids of (i) to (iii) above due to the degeneracy of the genetic code.

More preferably, the transgenic plant, transgenic plant part, or transgenic plant cell according to the present invention has been obtained by transformation with a recombinant vector described herein.

Suitable methods for transforming or transfecting host cells including plant cells are well known in the art of plant biotechnology. Any method may be used to transform the recombinant expression vector into plant cells to yield the transgenic plants of the invention. General methods for transforming dicotyledonous plants are disclosed, for example, in U.S. Pat. Nos. 4,940,838; 5,464,763, and the like. Methods for transforming specific dicotyledonous plants, for example, cotton, are set forth in U.S. Pat. Nos. 5,004,863; 5,159,135; and 5,846,797. Soy transformation methods are set forth in U.S. Pat. Nos. 4,992,375; 5,416,011; 5,569,834; 5,824,877; 6,384,301 and in EP 0301749B1 may be used. Transformation methods may include direct and indirect methods of transformation. Suitable direct methods include polyethylene glycol induced DNA uptake, liposome-mediated transformation (U.S. Pat. No. 4,536,475), biolistic methods using the gene gun (Fromm M E et a/., Bio/Technology. 8(9):833-9, 1990; Gordon-Kamm et al. Plant Cell 2:603, 1990), electroporation, incubation of dry embryos in DNA-comprising solution, and microinjection. In the case of these direct transformation methods, the plasmids used need not meet any particular requirements. Simple plasmids, such as those of the pUC series, pBR322, M13mp series, pACYC184 and the like can be used. If intact plants are to be regenerated from the transformed cells, an additional selectable marker gene is preferably located on the plasmid. The direct transformation techniques are equally suitable for dicotyledonous and monocotyledonous plants.

Transformation can also be carried out by bacterial infection by means of *Agrobacterium* (for example EP 0 116 718), viral infection by means of viral vectors (EP 0 067 553; U.S. Pat. No. 4,407,956; WO 95/34668; WO 93/03161) or by means of pollen (EP 0 270 356; WO 85/01856; U.S. Pat. No. 4,684,611). *Agrobacterium* based transformation techniques (especially for dicotyledonous plants) are well known in the art. The *Agrobacterium* strain (e.g., *Agrobacterium tumefaciens* or *Agrobacterium rhizogenes*) comprises a plasmid (Ti or Ri plasmid) and a T-DNA element which is transferred to the plant following infection with *Agrobacterium*. The T-DNA (transferred DNA) is integrated into the genome of the plant cell. The T-DNA may be localized on the Ri- or Ti-plasmid or is separately comprised in a so-called binary vector. Methods for the *Agrobacterium*-mediated transformation are described, for example, in Horsch R B et al. (1985) Science 225:1229. The *Agrobacterium*-mediated transformation is best suited to dicotyledonous plants but has also been adapted to monocotyledonous plants. The transformation of plants by *Agrobacteria* is described in, for example, White F F, Vectors for Gene Transfer in Higher Plants, Transgenic Plants, Vol. 1, Engineering and Utilization, edited by S. D. Kung and R. Wu, Academic Press, 1993, pp. 15-38; Jenes B et al. Techniques for Gene Transfer, Transgenic Plants, Vol. 1, Engineering and Utilization, edited by S. D. Kung and R. Wu, Academic Press, 1993, pp. 128-143; Potrykus (1991) Annu Rev Plant Physiol Plant Molec Biol 42:205-225. Transformation may result in transient or stable transformation and expression. Although a nucleotide sequence of the present invention can be inserted into any plant and plant cell falling within these broad classes, it is particularly useful in crop plant cells.

The genetically modified plant cells can be regenerated via all methods with which the skilled worker is familiar. Suitable methods can be found in the abovementioned publications by S. D. Kung and R. Wu, Potrykus or Höfgen and Willmitzer.

After transformation, plant cells or cell groupings may be selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above. The transformed plants may also be directly selected by screening for the presence of the hydrophobin nucleic acid.

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

Preferably, the transgenic plant of the present invention or the plant obtained by the method of the present invention has increased resistance against fungal pathogens, preferably against fungal pathogens of the family Phacopsoraceae, more preferably against fungal pathogens of the genus *Phacopsora*, most preferably against *Phakopsora pachyrhizi* (Sydow) and *Phakopsora meibomiae* (Arthur), also known as soybean rust. Preferably, resistance against *Phakopsora pachyrhizi* (Sydow) and/or *Phakopsora meibomiae* (Arthur) is increased.

Preferably, the plant, plant part, or plant cell is a plant or derived from a plant selected from the group consisting of beans, soya, pea, clover, kudzu, lucerne, lentils, lupins, vetches, groundnut, rice, wheat, barley, *arabidopsis*, lentil, banana, canola, cotton, potato, corn, sugar cane, alfalfa, and sugar beet.

In one embodiment of the present invention the plant is selected from the group consisting of beans, soya, pea, clover, kudzu, lucerne, lentils, lupins, vetches, and/or groundnut. Preferably, the plant is a legume, comprising plants of the genus *Phaseolus* (comprising French bean, dwarf bean, climbing bean (*Phaseolus vulgaris*), Lima bean (*Phaseolus lunatus* L.), Tepary bean (*Phaseolus acutifolius* A. Gray), runner bean (*Phaseolus coccineus*)); the genus *Glycine* (comprising *Glycine soja*, soybeans (*Glycine max* (L.) Merill)); pea (*Pisum*) (comprising shelling peas (*Pisum sativum* L. convar. *sativum*), also called smooth or round-seeded peas; marrowfat pea (*Pisum sativum* L. convar. medullare Alef. emend. C.O. Lehm), sugar pea (*Pisum sativum* L. convar. axiphium Alef emend. C.O. Lehm), also called snow pea, edible-podded pea or mangetout, (*Pisum granda sneida* L. convar. sneidulo p. shneiderium)); peanut (*Arachis hypogaea*), clover (*Trifolium* spec.), medick (*Medicago*), kudzu vine (*Pueraria lobata*), common lucerne, alfalfa (*M. sativa* L.), chickpea (*Cicer*), lentils (Lens) (*Lens culinaris* Medik.), lupins (*Lupinus*); vetches (*Vicia*), field bean, broad bean (*Vicia faba*), vetchling (*Lathyrus*) (comprising chickling pea (*Lathyrus sativus*), heath pea (*Lathyrus tuberosus*)); genus *Vigna* (comprising moth bean (*Vigna aconitifolia* (Jacq.) Maréchal), adzuki bean (*Vigna angularis* (Willd.) Ohwi & H. Ohashi), urd bean (*Vigna mungo* (L.) Hepper), mung bean (*Vigna radiata* (L.) R. Wilczek), bambara groundnut (*Vigna subterrane* (L.) Verdc.), rice bean (*Vigna umbellata* (Thunb.) Ohwi & H. Ohashi), *Vigna vexillata* (L.) A. Rich., *Vigna unguiculata* (L.) Walp., in the three subspecies asparagus bean, cowpea, catjang bean)); pigeonpea (*Cajanus cajan* (L.) Millsp.), the genus *Macrotyloma* (comprising geocarpa groundnut (*Macrotyloma geocarpum* (Harms) Marechal & Baudet), horse bean (*Macrotyloma uniflorum* (Lam.) Verdc.)); goa bean (*Psophocarpus tetragonolobus* (L.) DC.), African yam bean (*Sphenostylis stenocarpa* (Hochst. ex A. Rich.) Harms), Egyptian black bean, dolichos bean, *lablab* bean (*Lablab purpureus* (L.) Sweet), yam bean (*Pachyrhizus*), guar bean (*Cyamopsis tetragonolobus* (L.) Taub.); and/or the genus *Canavalia* (comprising jack bean (*Canavalia ensiformis* (L.) DC.), sword bean (*Canavalia gladiata* (Jacq.) DC.)).

Further preferred is a plant selected from plant is selected from the group consisting of beans, soya, pea, clover, kudzu, lucerne, lentils, lupins, vetches, and groundnut. Most preferably, the plant, plant part, or plant cell is or is derived from soy.

Methods for the Production of Transgenic Plants

One embodiment according to the present invention provides a method for producing a transgenic plant, a transgenic plant part, or a transgenic plant cell resistant to a fungal pathogen, preferably of the family Phacopsoraceae, for example soybean rust, wherein the recombinant nucleic acid used to generate a transgenic plant comprises a promoter that is functional in the plant cell, operably linked to a hydrophobin nucleic acid, which is preferably SEQ ID NO: 1, and a terminator regulatory sequence.

In one embodiment, the present invention refers to a method for the production of a transgenic plant, transgenic plant part, or transgenic plant cell having increased fungal resistance, comprising (a) introducing a recombinant vector construct according to the present invention into a plant, a plant part or a plant cell and (b) generating a transgenic plant from the plant, plant part or plant cell.

Preferably, the method for the production of the transgenic plant, transgenic plant part, or transgenic plant cell further comprises the step (c) expressing the hydrophobin protein, preferably encoded by (i) an exogenous nucleic acid having at least 60% identity with SEQ ID NO: 1, 3, 5, 7, 9, 11, 13, 39, 41, 55-62, 89, or 90, or a functional fragment, thereof, an orthologue or a paralogue thereof; or by (ii) an exogenous nucleic acid encoding a protein having at least 60% identity with SEQ ID NO: 2, 4, 6, 8, 10, 12, 14, 40, 42, 43, 44, 45, 46, 87, or 88, a functional fragment thereof, an orthologue or a paralogue thereof;

(iii) an exogenous nucleic acid capable of hybridizing under stringent conditions with any of the nucleic acids according to (i) or (ii) or a complement thereof. Most preferably, the exogenous nucleic acid has at least 95%, at least 98%, at least 99% sequence identity, or even 100% sequence identity with SEQ ID NO: 1; or comprises an exogenous nucleic acid encoding a protein having at least 95%, at least 98%, at least 99% sequence identity, or even 100% sequence identity with SEQ ID NO: 2; and/or by (iv) a nucleic acid encoding the same protein as the nucleic acids of (i) to (iii) above, but differing from the nucleic acids of (i) to (iii) above due to the degeneracy of the genetic code.

In case the coding sequence for a hydrophobin fusion protein is transformed, the hydrophobin fusion protein expressed in the plant, plant part or plant cell is preferably encoded by (i) an exogenous nucleic acid having at least 60% identity with SEQ ID NO: 47, 49, 51, 27, 29, 31, 33, 35, 63-70, 71, 73, 75, 77, 79, 81, 83, or 85, or a functional fragment, thereof, an orthologue or a paralogue thereof; or by (ii) an exogenous nucleic acid encoding a protein having at least 60% identity with SEQ ID NO: 48, 50, 52, 28, 30, 32, 34, 36, 72, 74, 76, 78, 80, 82, 84, or 86, a functional fragment thereof, an orthologue or a paralogue thereof;

(iii) an exogenous nucleic acid capable of hybridizing under stringent conditions with any of the nucleic acids according to (i) or (ii) or a complement thereof. Most preferably, the exogenous nucleic acid has at least 95%, at least 98%, at least 99% sequence identity, or even 100% sequence identity with SEQ ID NO: 27 or 29; or comprises an exogenous nucleic acid encoding a protein having at least 95%, at least 98%, at least 99% sequence identity, or even 100% sequence identity with SEQ ID NO: 28 or 30; and/or by (iv) a nucleic acid encoding the same protein as the nucleic acids of (i) to (iii) above, but differing from the nucleic acids of (i) to (iii) above due to the degeneracy of the genetic code;

Preferably, the method for the production of the transgenic plant, transgenic plant part, or transgenic plant cell additionally comprises the step of harvesting the seeds of the transgenic plant and planting the seeds and growing the seeds to plants, wherein the grown plant(s) comprises (i) an exogenous nucleic acid having at least 60% identity with SEQ ID NO: 1, 3, 5, 7, 9, 11, 13, 39, 41, 55-62, 89, or 90, or a functional fragment, thereof, an orthologue or a paralogue thereof; or by (ii) an exogenous nucleic acid encoding a protein having at least 60% identity with SEQ ID NO: 2, 4, 6, 8, 10, 12, 14, 40, 42, 43, 44, 45, 46, 87, or 88, a functional fragment thereof, an orthologue or a paralogue thereof;

(iii) an exogenous nucleic acid capable of hybridizing under stringent conditions with any of the nucleic acids according to (i) or (ii) or a complement thereof. Most preferably, the exogenous nucleic acid has at least 95%, at least 98%, at least 99% sequence identity, or even 100% sequence identity with SEQ ID NO: 1; or comprises an exogenous nucleic acid encoding a protein having at least 95%, at least 98%, at least 99% sequence identity, or even 100% sequence identity with SEQ ID NO: 2; and/or by (iv) a nucleic acid encoding the same protein as the nucleic acids of (i) to (iii) above, but differing from the nucleic acids of (i) to (iii) above due to the degeneracy of the genetic code;

In case the coding sequence for a hydrophobin fusion protein is used, the grown plant(s) comprises (i) an exogenous nucleic acid having at least 60% identity with SEQ ID NO: 47, 49, 51, 27, 29, 31, 33, 35, 63-70, 71, 73, 75, 77, 79, 81, 83, or 85, or a functional fragment, thereof, an orthologue or a paralogue thereof; or by (ii) an exogenous nucleic acid encoding a protein having at least 60% identity with SEQ ID NO: 48, 50, 52, 28, 30, 32, 34, 36, 72, 74, 76, 78, 80, 82, 84, or 86, a functional fragment thereof, an orthologue or a paralogue thereof;

(iii) an exogenous nucleic acid capable of hybridizing under stringent conditions with any of the nucleic acids according to (i) or (ii) or a complement thereof. Most preferably, the exogenous nucleic acid has at least 95%, at least 98%, at least 99% sequence identity, or even 100% sequence identity with SEQ ID NO: 27 or 29; or comprises an exogenous nucleic acid encoding a protein having at least 95%, at least 98%, at least 99% sequence identity, or even 100% sequence identity with SEQ ID NO: 28 or 30; and/or by (iv) a nucleic acid encoding the same protein as the nucleic acids of (i) to (iii) above, but differing from the nucleic acids of (i) to (iii) above due to the degeneracy of the genetic code;

The transgenic plants may be selected by known methods as described above (e.g., by screening for the presence of one or more markers which are encoded by plant-expressible genes co-transferred with the hydrophobin gene or by directly screening for the hydrophobin nucleic acid).

Furthermore, the use of the exogenous hydrophobin nucleic acid or the recombinant vector construct comprising the hydrophobin nucleic acid for the transformation of a plant, plant part, or plant cell to provide a fungal resistant plant, plant part, or plant cell is provided.

Harvestable Parts and Products

Harvestable parts of the transgenic plant according to the present invention are part of the invention. The harvestable parts may be seeds, roots, leaves and/or flowers comprising the hydrophobin nucleic acid or hydrophobin protein or parts thereof. Preferred parts of soy plants are soy beans comprising the hydrophobin nucleic acid or hydrophobin protein.

Products derived from a transgenic plant according to the present invention, parts thereof or harvestable parts thereof are part of the invention. A preferred product is soybean meal or soybean oil.

Preferably, the harvestable part of the transgenic plant or the product derived from the transgenic plant comprises an exogenous hydrophobin nucleic acid, wherein the exogenous hydrophobin nucleic acid is selected from the group consisting of:

(i) an exogenous nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 1, 3, 5, 7, 9, 11, 13, 39, 41, 55-62, 89, or 90, or a functional fragment, derivative, orthologue, or paralogue thereof;

(ii) the complementary sequence of anyone of the nucleic acids of (i);

(iii) an exogenous nucleic acid encoding a hydrophobin protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 2, 4, 6, 8, 10, 12, 14, 40, 42, 43, 44, 45, 46, 87, or 88, or a functional fragment, derivative, orthologue, or paralogue thereof; preferably the hydrophobin polypeptide confers enhanced fungal resistance relative to control plants;

(iv) an exogenous nucleic acid molecule which hybridizes with a nucleic acid molecule of (i) to (iii) under high stringency hybridization conditions; and (v) a nucleic acid encoding the same protein as the nucleic acids of (i) to (iv) above, but differing from the nucleic acids of (i) to (iv) above due to the degeneracy of the genetic code;

or wherein the harvestable part of the transgenic plant or the product derived from the transgenic plant comprises a hydrophobin protein encoded by any one of the hydrophobin nucleic acids of (i) to (v).

Method for Manufacturing a Product

In one embodiment the method for the production of a product comprises a) growing the plants of the invention or obtainable by the methods of invention and b) producing said product from or by the plants of the invention and/or parts, e.g. seeds, of these plants.

In a further embodiment the method comprises the steps a) growing the plants of the invention, b) removing the harvestable parts as described above from the plants and c) producing said product from or by the harvestable parts of the invention.

Preferably, the product obtained by said method comprises an exogenous hydrophobin nucleic acid selected from the group consisting of:

(i) an exogenous nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 1, 3, 5, 7, 9, 11, 13, 39, 41, 55-62, 89, or 90, or a functional fragment, derivative, orthologue, or paralogue thereof;

(ii) the complementary sequence of anyone of the nucleic acids of (i);

(iii) an exogenous nucleic acid encoding a hydrophobin protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 2, 4, 6, 8, 10, 12, 14, 40, 42, 43, 44, 45, 46, 87, or 88, or a functional fragment, derivative, orthologue, or paralogue thereof; preferably the hydrophobin polypeptide confers enhanced fungal resistance relative to control plants;

(iv) an exogenous nucleic acid molecule which hybridizes with a nucleic acid molecule of (i) to (iii) under high stringency hybridization conditions; and (v) a nucleic acid encoding the same protein as the nucleic acids of (i) to (iv) above, but differing from the nucleic acids of (i) to (iv) above due to the degeneracy of the genetic code;

or wherein the product obtained by said method comprises a hydrophobin protein encoded by any one of the hydrophobin nucleic acids of (i) to (v).

The product may be produced at the site where the plant has been grown, the plants and/or parts thereof may be removed from the site where the plants have been grown to produce the product. Typically, the plant is grown, the desired harvestable parts are removed from the plant, if feasible in repeated cycles, and the product made from the harvestable parts of the plant. The step of growing the plant may be performed only once each time the methods of the invention is performed, while allowing repeated times the steps of product production e.g. by repeated removal of harvestable parts of the plants of the invention and if necessary further processing of these parts to arrive at the product. It is also possible that the step of growing the plants of the invention is repeated and plants or harvestable parts are stored until the production of the product is then performed once for the accumulated plants or plant parts. Also, the steps of growing the plants and producing the product may be performed with an overlap in time, even simultaneously to a large extend or sequentially. Generally the plants are grown for some time before the product is produced.

In one embodiment the products produced by said methods of the invention are plant products such as, but not limited to, a foodstuff, feedstuff, a food supplement, feed supplement, fiber, cosmetic and/or pharmaceutical. Foodstuffs are regarded as compositions used for nutrition and/or for supplementing nutrition. Animal feedstuffs and animal feed supplements, in particular, are regarded as foodstuffs.

In another embodiment the inventive methods for the production are used to make agricultural products such as, but not limited to, plant extracts, proteins, amino acids, carbohydrates, fats, oils, polymers, vitamins, and the like.

It is possible that a plant product consists of one or more agricultural products to a large extent.

The transgenic plants of the invention may be crossed with similar transgenic plants or with transgenic plants lacking the nucleic acids of the invention or with non-transgenic plants, using known methods of plant breeding, to prepare seeds. Further, the transgenic plant cells or plants of the present invention may comprise, and/or be crossed to another transgenic plant that comprises one or more exogenous nucleic acids, thus creating a "stack" of transgenes in the plant and/or its progeny. The seed is then planted to obtain a crossed fertile transgenic plant comprising the hydrophobin nucleic acid. The crossed fertile transgenic plant may have the particular expression cassette inherited through a female parent or through a male parent. The second plant may be an inbred plant. The crossed fertile transgenic may be a hybrid. Also included within the present invention are seeds of any of these crossed fertile transgenic plants. The seeds of this invention can be harvested from fertile transgenic plants and be used to grow progeny generations of transformed plants of this invention including hybrid plant lines comprising the exogenous nucleic acid.

Method for Breeding

Thus, one embodiment of the present invention is a method for breeding a fungal resistant plant comprising the steps of
(a) crossing a transgenic plant described herein or a plant obtainable by a method described herein with a second plant;
(b) obtaining a seed or seeds resulting from the crossing step described in (a);
(c) planting said seed or seeds and growing the seed or seeds to plants; and
(d) selecting from said plants the plants expressing a hydrophobin protein, preferably encoded by
  (i) an exogenous nucleic acid having at least 60% identity with SEQ ID NO: 1, 3, 5, 7, 9, 11, 13, 39, 41, 55-62, 89, or 90, or a functional fragment, thereof, an orthologue or a paralogue thereof; or by
  (ii) an exogenous nucleic acid encoding a protein having at least 60% identity with SEQ ID NO: 2, 4, 6, 8, 10, 12, 14, 40, 42, 43, 44, 45, 46, 87, or 88, a functional fragment thereof, an orthologue or a paralogue thereof;
  (iii) an exogenous nucleic acid capable of hybridizing under stringent conditions with any of the nucleic acids according to (i) or (ii) or a complement thereof. Most preferably, the exogenous nucleic acid has at least 95%, at least 98%, at least 99% sequence identity, or even 100% sequence identity with SEQ ID NO: 1; or comprises an exogenous nucleic acid encoding a protein having at least 95%, at least 98%, at least 99% sequence identity, or even 100% sequence identity with SEQ ID NO: 2; and/or by
  (iv) a nucleic acid encoding the same protein as the nucleic acids of (i) to (iii) above, but differing from the nucleic acids of (i) to (iii) above due to the degeneracy of the genetic code.

In case the coding sequence for a hydrophobin fusion protein is used, plants are selected expressing a hydrophobin fusion protein, preferably encoded by
(i) an exogenous nucleic acid having at least 60% identity with SEQ ID NO: 47, 49, 51, 27, 29, 31, 33, 35, 63-70, 71, 73, 75, 77, 79, 81, 83, or 85, or a functional fragment, thereof, an orthologue or a paralogue thereof; or by
(ii) an exogenous nucleic acid encoding a protein having at least 60% identity with SEQ ID NO: 48, 50, 52, 28, 30, 32, 34, 36, 72, 74, 76, 78, 80, 82, 84, or 86, a functional fragment thereof, an orthologue or a paralogue thereof; and/or by
(iii) an exogenous nucleic acid capable of hybridizing under stringent conditions with any of the nucleic acids according to (i) or (ii) or a complement thereof. Most preferably, the exogenous nucleic acid has at least 95%, at least 98%, at least 99% sequence identity, or even 100% sequence identity with SEQ ID NO: 27 or 29; or comprises an exogenous nucleic acid encoding a protein having at least 95%, at least 98%, at least 99% sequence identity, or even 100% sequence identity with SEQ ID NO: 28 or 30; and/or by
(iv) a nucleic acid encoding the same protein as the nucleic acids of (i) to (iii) above, but differing from the nucleic acids of (i) to (iii) above due to the degeneracy of the genetic code.

The transgenic plants may be selected by known methods as described above (e.g., by screening for the presence of one or more markers which are encoded by plant-expressible genes co-transferred with the hydrophobin gene or screening for the hydrophobin nucleic acid itself).

According to the present invention, the introduced hydrophobin nucleic acid may be maintained in the plant cell stably if it is incorporated into a non-chromosomal autonomous replicon or integrated into the plant chromosomes. Whether present in an extra-chromosomal non-replicating or replicating vector construct or a vector construct that is integrated into a chromosome, the exogenous hydrophobin nucleic acid preferably resides in a plant expression cassette. A plant expression cassette preferably contains regulatory sequences capable of driving gene expression in plant cells that are functional linked so that each sequence can fulfill its function, for example, termination of transcription by polyadenylation signals. Preferred polyadenylation signals are those originating from *Agrobacterium tumefaciens* t-DNA such as the gene 3 known as octopine synthase of the Ti-plasmid pTiACH5 (Gielen et al, 1984, EMBO J. 3:835) or functional equivalents thereof, but also all other terminators functionally active in plants are suitable. As plant gene expression is very often not limited on transcriptional levels, a plant expression cassette preferably contains other functional linked sequences like translational enhancers such as the overdrive-sequence containing the 5'-untranslated leader sequence from tobacco mosaic virus increasing the polypeptide per RNA ratio (Gallie et al, 1987, Nucl. Acids Research 15:8693-8711). Examples of plant expression vectors include those detailed in: Becker, D. et al, 1992, New plant binary vectors with selectable markers located proximal to the left border, Plant Mol. Biol. 20:1195-1197; Bevan, M. W., 1984, Binary *Agrobacterium* vectors for plant transformation, Nucl. Acid. Res. 12:8711-8721; and Vectors for Gene Transfer in Higher Plants; in: Transgenic Plants, Vol. 1, Engineering and Utilization, eds.: Kung and R. Wu, Academic Press, 1993, S. 15-38.

EXAMPLES

The following examples are not intended to limit the scope of the claims to the invention, but are rather intended to be exemplary of certain embodiments. Any variations in the exemplified methods that occur to the skilled artisan are intended to fall within the scope of the present invention.

Example 1: General Methods

The chemical synthesis of oligonucleotides can be affected, for example, in the known fashion using the phosphoramidite method (Voet, Voet, 2nd Edition, Wiley Press New York, pages 896-897). The cloning steps carried out for the purposes of the present invention such as, for example, restriction cleavages, agarose gel electrophoresis, purification of DNA fragments, transfer of nucleic acids to nitrocellulose and nylon membranes, linking DNA fragments, transformation of *E. coli* cells, bacterial cultures, phage multiplication and sequence analysis of recombinant DNA, are carried out as described by Sambrook et al. Cold Spring Harbor Laboratory Press (1989), ISBN 0-87969-309-6. The sequencing of recombinant DNA molecules is carried out with an MWG-Licor laser fluorescence DNA sequencer following the method of Sanger (Sanger et al., Proc. Natl. Acad. Sci. USA 74, 5463 (1977)).

Example 2: Cloning of Overexpression Vector Constructs

The cDNAs of all genes mentioned in this application were generated by DNA synthesis (Geneart, Regensburg, Germany).

The hydrophobin nucleic acids (as shown in SEQ ID NO: 27 and SEQ ID NO: 29) were synthesized in a way that a PacI restriction site is located in front of the start-ATG and a AscI restriction site downstream of the stop-codon. The synthesized cDNAs were digested using the restriction enzymes PacI and AscI (NEB Biolabs) and ligated in a PacI/AscI digested Gateway pENTRY vector (Invitrogen, Life Technologies, Carlsbad, Calif., USA) in a way that the full-length fragment is located in sense direction between the Glyma02g47670 promoter (epidermis-specific promoter) and a Solanum tuberosum [Potato] cathepsin D inhibitor gene terminator (CATHD) terminator.

To obtain the binary plant transformation vector, a triple LR reaction (Gateway system, Invitrogen, Life Technologies, Carlsbad, Calif., USA) was performed according to manufacturers protocol by using an empty pENTRY-A vector, the promoter::cDNA::terminator in a pENTRY-B vector and an empty pENTRY-C vector. As target a binary pDEST vector was used which is composed of: (1) a Spectinomycin/Streptomycin resistance cassette for bacterial selection (2) a pVS1 origin for replication in Agrobacteria (3) a pBR322 origin of replication for stable maintenance in E. coli and (4) between the right and left border an AHAS selection under control of a pcUbi-promoter (FIG. 4). The recombination reaction was transformed into E. coli (DH5alpha), miniprepped and screened by specific restriction digestions. A positive clone from each vector construct was sequenced and submitted soy transformation.

Example 3: Soy Transformation

The expression vector constructs (see example 2) were transformed into soy.

3.1 Sterilization and Germination of Soy Seeds

Virtually any seed of any soy variety can be employed in the method of the invention. A variety of soycultivar (including Jack, Williams 82, Jake, Stoddard and Resnik) is appropriate for soy transformation. Soy seeds were sterilized in a chamber with a chlorine gas produced by adding 3.5 ml 12N HCl drop wise into 100 ml bleach (5.25% sodium hypochlorite) in a desiccator with a tightly fitting lid. After 24 to 48 hours in the chamber, seeds were removed and approximately 18 to 20 seeds were plated on solid GM medium with or without 5 µM 6-benzyl-aminopurine (BAP) in 100 mm Petri dishes. Seedlings without BAP are more elongated and roots develop, especially secondary and lateral root formation. BAP strengthens the seedling by forming a shorter and stockier seedling.

Seven-day-old seedlings grown in the light (>100 µEinstein/m$^2$s) at 25° C. were used for explant material for the three-explant types. At this time, the seed coat was split, and the epicotyl with the unifoliate leaves have grown to, at minimum, the length of the cotyledons. The epicotyl should be at least 0.5 cm to avoid the cotyledonary-node tissue (since soycultivars and seed lots may vary in the developmental time a description of the germination stage is more accurate than a specific germination time).

For inoculation of entire seedlings, see Method A (example 3.3. and 3.3.2) or leaf explants, see Method B (example 3.3.3).

For method C (see example 3.3.4), the hypocotyl and one and a half or part of both cotyledons were removed from each seedling. The seedlings were then placed on propagation media for 2 to 4 weeks. The seedlings produce several branched shoots to obtain explants from. The majority of the explants originated from the plantlet growing from the apical bud. These explants were preferably used as target tissue.

3.2—Growth and Preparation of Agrobacterium Culture

Agrobacterium cultures were prepared by streaking Agrobacterium (e.g., A. tumefaciens or A. rhizogenes) carrying the desired binary vector (e.g. H. Klee. R. Horsch and S. Rogers 1987 Agrobacterium-Mediated Plant Transformation and its further Applications to Plant Biology; Annual Review of Plant Physiology Vol. 38: 467-486) onto solid YEP growth medium YEP media: 10 g yeast extract, 10 g Bacto Peptone, 5 g NaCl, Adjust pH to 7.0, and bring final volume to 1 liter with H2O, for YEP agar plates add 20 g Agar, autoclave) and incubating at 25° C. until colonies appeared (about 2 days). Depending on the selectable marker genes present on the Ti or Ri plasmid, the binary vector, and the bacterial chromosomes, different selection compounds were be used for A. tumefaciens and rhizogenes selection in the YEP solid and liquid media. Various Agrobacterium strains can be used for the transformation method.

After approximately two days, a single colony (with a sterile toothpick) was picked and 50 ml of liquid YEP was inoculated with antibiotics and shaken at 175 rpm (25° C.) until an $OD_{600}$ between 0.8-1.0 is reached (approximately 2 d). Working glycerol stocks (15%) for transformation are prepared and one-ml of Agrobacterium stock aliquoted into 1.5 ml Eppendorf tubes then stored at −80° C.

The day before explant inoculation, 200 ml of YEP were inoculated with 5 µl to 3 ml of working Agrobacterium stock in a 500 ml Erlenmeyer flask. The flask was shaked overnight at 25° C. until the $OD_{600}$ was between 0.8 and 1.0. Before preparing the soy explants, the Agrobacteria were pelleted by centrifugation for 10 min at 5,500+g at 20° C. The pellet was resuspended in liquid CCM to the desired density ($OD_{600}$ 0.5-0.8) and placed at room temperature at least 30 min before use.

3.3—Explant Preparation and Co-Cultivation (Inoculation)

3.3.1 Method a: Explant Preparation on the Day of Transformation.

Seedlings at this time had elongated epicotyls from at least 0.5 cm but generally between 0.5 and 2 cm. Elongated epicotyls up to 4 cm in length had been successfully employed. Explants were then prepared with: i) with or without some roots, ii) with a partial, one or both cotyledons, all preformed leaves were removed including apical meristem, and the node located at the first set of leaves was injured with several cuts using a sharp scalpel.

This cutting at the node not only induced Agrobacterium infection but also distributed the axillary meristem cells and damaged pre-formed shoots. After wounding and preparation, the explants were set aside in a Petri dish and subsequently co-cultivated with the liquid CCM/Agrobacterium mixture for 30 minutes. The explants were then removed from the liquid medium and plated on top of a sterile filter paper on 15×100 mm Petri plates with solid co-cultivation medium. The wounded target tissues were placed such that they are in direct contact with the medium.

3.3.2 Modified Method A: Epicotyl Explant Preparation

Soyepicotyl segments prepared from 4 to 8 d old seedlings were used as explants for regeneration and transformation. Seeds of soya cv. L00106CN, 93-41131 and Jack were germinated in 1/10 MS salts or a similar composition medium with or without cytokinins for 4 to 8 d. Epicotyl explants were prepared by removing the cotyledonary node and stem node from the stem section. The epicotyl was cut into 2 to 5 segments. Especially preferred are segments attached to the primary or higher node comprising axillary meristematic tissue.

The explants were used for Agrobacterium infection. Agrobacterium AGL1 harboring a plasmid with the gene of interest (GOI) and the AHAS, bar or dsdA selectable marker gene was cultured in LB medium with appropriate antibiotics overnight, harvested and resuspended in a inoculation medium with acetosyringone. Freshly prepared epicotyl segments were soaked in the Agrobacterium suspension for 30 to 60 min and then the explants were blotted dry on sterile filter papers. The inoculated explants were then cultured on a coculture medium with L-cysteine and TTD and other chemicals such as acetosyringone for increasing T-DNA delivery for 2 to 4 d. The infected epicotyl explants were then placed on a shoot induction medium with selection agents such as imazapyr (for AHAS gene), glufosinate (for bar gene), or D-serine (for dsdA gene). The regenerated shoots were subcultured on elongation medium with the selective agent.

For regeneration of transgenic plants the segments were then cultured on a medium with cytokinins such as BAP, TDZ and/or Kinetin for shoot induction. After 4 to 8 weeks, the cultured tissues were transferred to a medium with lower concentration of cytokinin for shoot elongation. Elongated shoots were transferred to a medium with auxin for rooting and plant development. Multiple shoots were regenerated.

Many stable transformed sectors showing strong cDNA expression were recovered. Soyplants were regenerated from epicotyl explants. Efficient T-DNA delivery and stable transformed sectors were demonstrated.

3.3.3 Method B: Leaf Explants

For the preparation of the leaf explant the cotyledon was removed from the hypocotyl. The cotyledons were separated from one another and the epicotyl is removed. The primary leaves, which consist of the lamina, the petiole, and the stipules, were removed from the epicotyl by carefully cutting at the base of the stipules such that the axillary meristems were included on the explant. To wound the explant as well as to stimulate de novo shoot formation, any preformed shoots were removed and the area between the stipules was cut with a sharp scalpel 3 to 5 times.

The explants are either completely immersed or the wounded petiole end dipped into the Agrobacterium suspension immediately after explant preparation. After inoculation, the explants are blotted onto sterile filter paper to remove excess Agrobacterium culture and place explants with the wounded side in contact with a round 7 cm Whatman paper overlaying the solid CCM medium (see above). This filter paper prevents A. tumefaciens overgrowth on the soy-explants. Wrap five plates with Parafilm™ "M" (American National Can, Chicago, Ill., USA) and incubate for three to five days in the dark or light at 25° C.

3.3.4 Method C: Propagated Axillary Meristem

For the preparation of the propagated axillary meristem explant propagated 3-4 week-old plantlets were used. Axillary meristem explants can be pre-pared from the first to the fourth node. An average of three to four explants could be obtained from each seedling. The explants were prepared from plantlets by cutting 0.5 to 1.0 cm below the axillary node on the internode and removing the petiole and leaf from the explant. The tip where the axillary meristems lie was cut with a scalpel to induce de novo shoot growth and allow access of target cells to the Agrobacterium. Therefore, a 0.5 cm explant included the stem and a bud.

Once cut, the explants were immediately placed in the Agrobacterium suspension for 20 to 30 minutes. After inoculation, the explants were blotted onto sterile filter paper to remove excess Agrobacterium culture then placed almost completely immersed in solid CCM or on top of a round 7 cm filter paper overlaying the solid CCM, depending on the Agrobacterium strain. This filter paper prevents Agrobacterium overgrowth on the soy-explants. Plates were wrapped with Parafilm™ "M" (American National Can, Chicago, Ill., USA) and incubated for two to three days in the dark at 25° C.

3.4—Shoot Induction

After 3 to 5 days co-cultivation in the dark at 25° C., the explants were rinsed in liquid SIM medium (to remove excess Agrobacterium) (SIM, see Olhoft et al 2007 A novel Agrobacterium rhizogenes-mediated transformation method of soy using primary-node explants from seedlings In Vitro Cell. Dev. Biol.—Plant (2007) 43:536-549; to remove excess Agrobacterium) or Modwash medium (1×B5 major salts, 1×B5 minor salts, 1×MSIII iron, 3% Sucrose, 1×B5 vitamins, 30 mM MES, 350 mg/L Timentin™ pH 5.6, WO 2005/121345) and blotted dry on sterile filter paper (to prevent damage especially on the lamina) before placing on the solid SIM medium. The approximately 5 explants (Method A) or 10 to 20 (Methods B and C) explants were placed such that the target tissue was in direct contact with the medium. During the first 2 weeks, the explants could be cultured with or without selective medium. Preferably, explants were transferred onto SIM without selection for one week.

For leaf explants (Method B), the explant should be placed into the medium such that it is perpendicular to the surface of the medium with the petiole imbedded into the medium and the lamina out of the medium.

For propagated axillary meristem (Method C), the explant was placed into the medium such that it was parallel to the surface of the medium (basipetal) with the explant partially embedded into the medium.

Wrap plates with Scotch 394 venting tape (3M, St. Paul, Minn., USA) were placed in a growth chamber for two weeks with a temperature averaging 25° C. under 18 h light/6 h dark cycle at 70-100 $\mu E/m^2 s$. The explants remained on the SIM medium with or without selection until de novo shoot growth occurred at the target area (e.g., axillary meristems at the first node above the epicotyl). Transfers to fresh medium can occur during this time. Explants were transferred from the SIM with or without selection to SIM with selection after about one week. At this time, there was considerable de novo shoot development at the base of the petiole of the leaf explants in a variety of SIM (Method B), at the primary node for seedling explants (Method A), and at the axillary nodes of propagated explants (Method C).

Preferably, all shoots formed before transformation were removed up to 2 weeks after co-cultivation to stimulate new growth from the meristems. This helped to reduce chimerism in the primary transformant and increase amplification of transgenic meristematic cells. During this time the explant may or may not be cut into smaller pieces (i.e. detaching the node from the explant by cutting the epicotyl).

3.5—Shoot Elongation

After 2 to 4 weeks (or until a mass of shoots was formed) on SIM medium (preferably with selection), the explants were transferred to SEM medium (shoot elongation medium, see Olhoft et al 2007 A novel *Agrobacterium rhizogenes*-mediated transformation method of soy using primary-node explants from seedlings. In Vitro Cell. Dev. Biol.—Plant (2007) 43:536-549) that stimulates shoot elongation of the shoot primordia. This medium may or may not contain a selection compound.

After every 2 to 3 weeks, the explants were transfer to fresh SEM medium (preferably containing selection) after carefully removing dead tissue. The explants should hold together and not fragment into pieces and retain somewhat healthy. The explants were continued to be transferred until the explant dies or shoots elongate. Elongated shoots >3 cm were removed and placed into RM medium for about 1 week (Method A and B), or about 2 to 4 weeks depending on the cultivar (Method C) at which time roots began to form. In the case of explants with roots, they were transferred directly into soil. Rooted shoots were transferred to soil and hardened in a growth chamber for 2 to 3 weeks before transferring to the greenhouse. Regenerated plants obtained using this method were fertile and produced on average 500 seeds per plant.

After 5 days of co-cultivation with *Agrobacterium tumefaciens* transient expression of the gene of interest (GOI) was widespread on the seedling axillary meristem explants especially in the regions wounding during explant preparation (Method A). Explants were placed into shoot induction medium without selection to see how the primary-node responds to shoot induction and regeneration. Thus far, greater than 70% of the explants were formed new shoots at this region. Expression of the GOI was stable after 14 days on SIM, implying integration of the T-DNA into the soy genome. In addition, preliminary experiments resulted in the formation of cDNA expressing shoots forming after 3 weeks on SIM.

For Method C, the average regeneration time of a soy plantlet using the propagated axillary meristem protocol was 14 weeks from explant inoculation. Therefore, this method has a quick regeneration time that leads to fertile, healthy soy plants.

Example 4: Pathogen Assay 4.1. Recovery of Clones 2-3 clones per To event were potted into small 6 cm pots. For recovery the clones were kept for 12-18 days in the phytochamber (16 h-day- and 8 h-night-Rhythm at a temperature of 16°-22° C. and a humidity of 75%).

4.2 Inoculation

The plants were inoculated with *P. pachyrhizi*

In order to obtain appropriate spore material for the inoculation, soy leaves which had been infected with rust 15-20 days ago, were taken 2-3 days before the inoculation and transferred to agar plates (1% agar in H2O). The leaves were placed with their upper side onto the agar, which allowed the fungus to grow through the tissue and to produce very young spores. For the inoculation solution, the spores were knocked off the leaves and were added to a Tween-H2O solution. The counting of spores was performed under a light microscope by means of a Thoma counting chamber. For the inoculation of the plants, the spore suspension was added into a compressed-air operated spray flask and applied uniformly onto the plants or the leaves until the leaf surface is well moisturized. For macroscopic assays we used a spore density of 1-5×105 spores/ml. For the microscopy, a density of >5×105 spores/ml is used. The inoculated plants were placed for 24 hours in a greenhouse chamber with an average of 22° C. and >90% of air humidity. The following cultivation was performed in a chamber with an average of 25° C. and 70% of air humidity.

Example 5: Microscopical Screening

For the evaluation of the pathogen development, the inoculated leaves of plants were stained with aniline blue 48 hours after infection.

The aniline blue staining serves for the detection of fluorescent substances. During the defense reactions in host interactions and non-host interactions, substances such as phenols, callose or lignin accumulated or were produced and were incorporated at the cell wall either locally in papillae or in the whole cell (hypersensitive reaction, HR). Complexes were formed in association with aniline blue, which lead e.g. in the case of callose to yellow fluorescence. The leaf material was transferred to falcon tubes or dishes containing destaining solution II (ethanol/acetic acid 6/1) and was incubated in a water bath at 90° C. for 10-15 minutes. The destaining solution II was removed immediately thereafter, and the leaves were washed 2× with water. For the staining, the leaves were incubated for 1.5-2 hours in staining solution II (0.05% aniline blue=methyl blue, 0.067 M di-potassium hydrogen phosphate) and analyzed by microscopy immediately thereafter.

The different interaction types were evaluated (counted) by microscopy. An Olympus UV microscope BX61 (incident light) and a UV Longpath filter (excitation: 375/15, Beam splitter: 405 LP) are used. After aniline blue staining, the spores appeared blue under UV light. The papillae could be recognized beneath the fungal appressorium by a green/yellow staining. The hypersensitive reaction (HR) was characterized by a whole cell fluorescence.

Example 6: Evaluating the Susceptibility to Soybean Rust

The progression of the soybean rust disease was scored by the estimation of the diseased area (area which was covered by sporulating uredinia) on the backside (abaxial side) of the leaf. Additionally the yellowing of the leaf was taken into account (for scheme see FIG. 2).

$T_0$ soybean plants expressing hydrophobin protein (as shown in SEQ ID NO: 30) were inoculated with spores of *Phakopsora pachyrhizi*. The macroscopic disease symptoms of soy against *P. pachyrhizi* of 25 $T_0$ soybean plants were scored 14 days after inoculation.

The average of the percentage of the leaf area showing fungal colonies or strong yellowing/browning on all leaves was considered as diseased leaf area. At all 25 soybean $T_0$ plants expressing hydrophobin (expression checked by RT-PCR) were evaluated in parallel to non-transgenic control plants. Clones from non-transgenic soy plants were used as control. The average of the diseased leaf area is shown in FIG. 7 for plants expressing recombinant hydrophobin compared with wildtype plants. Overexpression of hydrophobin reduces the diseased leaf area in comparison to non-transgenic control plants by 26% in average over all events generated. This data clearly indicates that the in-planta expression of the hydrophobin expression vector construct significantly (*: $p<0.05$) leads to a lower disease scoring of transgenic plants compared to non-transgenic controls. So, the expression of a hydrophobin nucleic acid (as shown in SEQ ID NO: 29) in the soybean epidermis increases the resistance of soy against soybean rust.

Example 7: Production of Purified Hydrophobin Proteins

The Hydrophobin proteins can be ordered at various companies. For example the hydrophobin SC3 (SEQ ID NO: 43, SEQ ID NO: 44) was purchased from Biomade Technology (Groningen, Netherlands) and HFPII protein (SEQ ID NO: 45, SEQ ID NO: 46) was custom synthezised by VTT (VTT Technical Research Centre of Finland, LAS-KUT, Finland). The other hydrophobin proteins were produced as a protein-fusion with the yaad-protein for better expression (yaaD_TT1: SEQ IDNO: 52, yaaD_HFPI: SEQ ID NO: 50, yaaD_HFBII: SEQ ID NO: 48). The yaad protein represents the synthase subunit Pdx1 (Yaad) of Plp synthase from *Bacillus subtilis*. The protein fusions were subsequently purified as described in WO 2007/014897.

Example 8: Spray-Application of Hydrophobin Proteins

Soybean wild type plants were grown in the phytochamber for 12-18 days (16 h-day- und 8 h-night-rhythm at a temperature of 16° to 22° C. und a humidity of ~75%).

Twenty-five (25) days-old plants were sprayed with a hydrophobin-protein solution (solved in PBS) to obtain a concentration of 1 mg/m$^2$, which is enough to obtain a fully covered monolayer of hydrophobin. 24 h after the application of hydrophobin the plants were inoculated with soybean rust spores, as described in Example 4. For each hydrophobin protein 10 plants were inoculated with the soybean rust fungus *Phakopsora pachyrhizi*.

Figure 2:
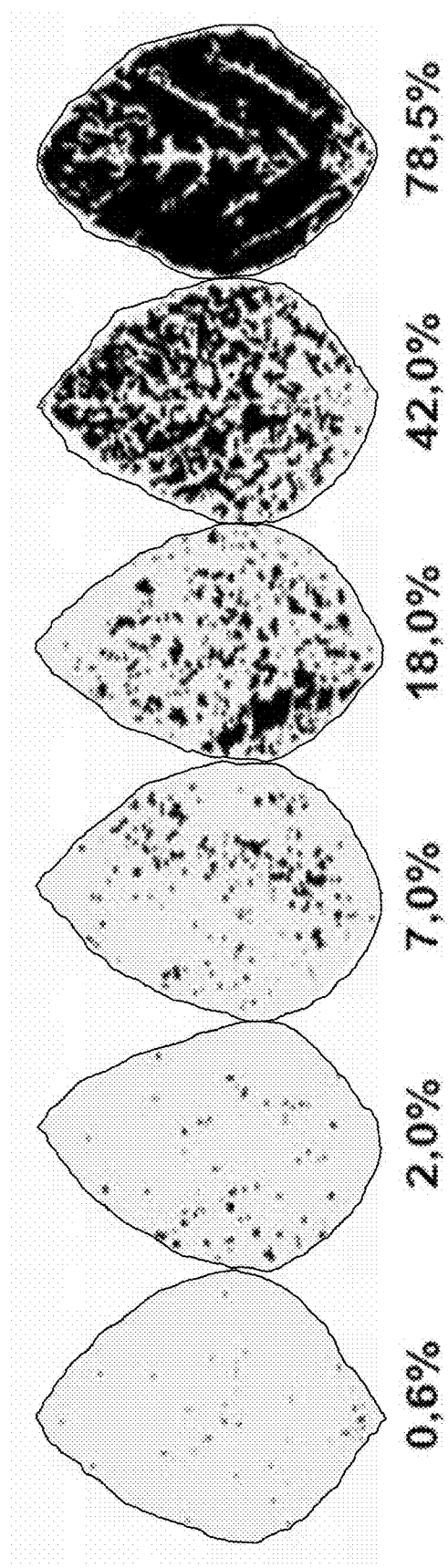
Figures 6, 7:
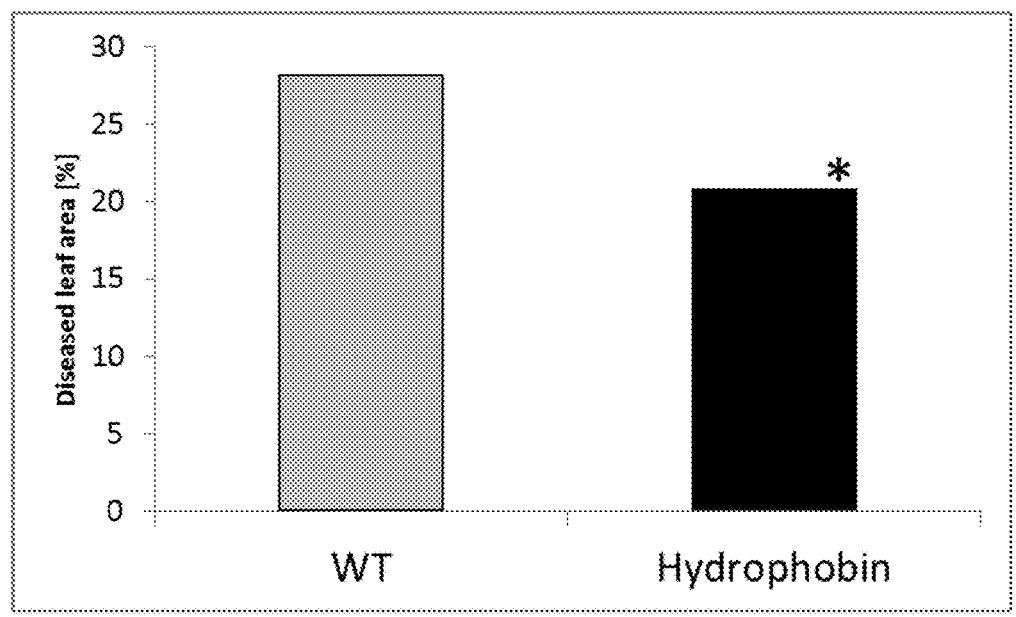

Fourteen (14) days after the inoculation with soybean rust, the diseased leaf area was scored by the estimation of the diseased area (area which was covered by sporulating uredinia) on the backside (abaxial side) of the leaf. Additionally the yellowing of the leaf was taken into account (for scheme see FIG. 2).

The macroscopic disease symptoms of hydrophobin-sprayed soybean (10 plants per hydrophobin variant) were scored 14 days after inoculation. The average of the percentage of the leaf area showing fungal colonies or strong yellowing/browning on all leaves was considered as diseased leaf area. At all 50 soybean T$_0$ plants sprayed with 5 different hydrophobin varieties (HFBII: SEQ ID NO: 45, Hydrophbin SC3: SEQ-ID NO: 43, yaaD TT1: SEQ ID NO: 52, yaaD HFPI: SEQ ID NO: 50, yaaD HFBII: SEQ ID NO: 48).

The average of the diseased leaf area is shown in FIG. 9 for plants sprayed with hydrophobin HFBII, Hydrophbin SC3 and yaaD_HFPI compared with untreated soybean plants. Spraying with these hydrophobin variants reduces the diseased leaf area in comparison to non-transgenic control plants by 6%-20% in average over all plants tested. The results for yaaD TT1 and yaaD HFBII were 51.1% and 47.3%, respectively. These results might be explained with the observation that coverage of the leaves with the hydrophobin after spraying was partially incomplete.

The data obtained with applying hydrophobins to a plant surface thus clearly indicates that the application of hydrophobins leads to a lower disease scoring compared to non-transgenic controls. The formulation for applying the hydrophobins to the plant surface by spraying might be further improved, e.g., by the addition of surfactants or detergents.

Overall the results demonstrate that the application of hydrophobins to soybean plants increases the resistance of soy against fungal pathogens.

The invention claimed is:

1. A method for preventing, reducing, or delaying *Phakopsora* infection in a transgenic soybean plant, a transgenic soybean plant part, or a transgenic soybean plant cell, the method comprising:

providing a transgenic soybean plant, a transgenic soybean plant part, or a transgenic soybean plant cell with an exogenous nucleic acid encoding a hydrophobin protein comprising an amino acid sequence with at least 90% identity to SEQ ID NO: 42 over the entire length of SEQ ID NO: 42, wherein the hydrophobin protein confers increased resistance against *Phakopsora* thereto in comparison to a wild type soybean plant, wild type soybean plant part, or wild type soybean plant cell, and growing the transgenic soybean plant, transgenic soybean plant part, or transgenic soybean plant cell in the presence of a fungal pathogen of the genus *Phakopsora*, wherein *Phakopsora* infection is prevented, reduced, or delayed in the transgenic soybean plant, transgenic soybean plant part, or transgenic soybean plant cell as compared to a wild type soybean plant, wild type soybean plant part, or wild type soybean plant cell.

2. The method of claim 1, wherein the exogenous nucleic acid is in functional linkage with a promoter.

3. The method of claim 2, wherein the exogenous nucleic acid encoding a hydrophobin protein encodes a hydrophobin fusion protein comprising the hydrophobin protein and one or more elements selected from the group consisting of signal sequence, fusion partner polypeptide, linker sequence, and purification sequence.

4. The method of claim 3, wherein the hydrophobin fusion protein comprises a signal sequence.

5. The method of claim 4, wherein the secretion signal sequence is encoded by:

an exogenous nucleic acid coding for a protein having an amino acid sequence with at least 80% identity to SEQ ID NO: 24.

6. The method of claim 3, wherein the hydrophobin fusion protein comprises a fusion partner polypeptide and the fusion partner polypeptide is encoded by an exogenous nucleic acid coding for a protein having an amino acid sequence with at least 70% identity to SEQ ID NO: 16.

7. The method of claim 2, wherein the promoter is a constitutive, pathogen-inducible promoter, a mesophyll-specific promoter or an epidermis specific-promoter.

8. A transgenic soybean plant, transgenic soybean plant part, or transgenic soybean plant cell having resistance to *Phakopsora* infection, comprising an exogenous nucleic acid coding for a hydrophobin protein having an amino acid sequence with at least 90% identity to SEQ ID NO: 42 in functional linkage with a promoter, wherein expression of the exogenous nucleic acid leads to increased resistance to *Phakopsora* infection thereto as compared to a wild type soybean plant, wild type soybean plant part, or wild type soybean plant cell.

9. A method for the production of a transgenic soybean plant, transgenic soybean plant part, or transgenic soybean plant cell having increased resistance to *Phakopsora* infection, comprising:

(a) introducing an expression cassette comprising:

an exogenous nucleic acid coding for a protein having an amino acid sequence with at least 90% identity to SEQ ID NO: 42 in functional linkage with a promoter; and (b) generating a transgenic soybean plant, transgenic soybean plant part, or transgenic soybean plant cell from the plant, plant part or plant cell, wherein expression of the exogenous nucleic acid leads to increased resistance to *Phakopsora* infection thereto as compared to a wild type soybean plant, wild type soybean plant part, or wild type soybean plant cell.

10. The method of claim 9, further comprising the step of harvesting the seeds of the transgenic plant and planting the seeds and growing the seeds to plants, wherein the grown plants comprise:

the exogenous nucleic acid encoding a protein having an amino acid sequence with at least 90% identity to SEQ ID NO: 42.

11. A harvestable part of the transgenic plant of claim 8, wherein the harvestable part of the transgenic plant comprises the exogenous hydrophobin nucleic acid encoding a protein having an amino acid sequence with at least 90% identity to SEQ ID NO: 42.

12. A product produced from the transgenic plant of claim 8, wherein the product comprises the exogenous hydrophobin nucleic acid encoding a protein having an amino acid sequence with at least 90% identity to SEQ ID NO: 42.

13. A method for the production of a product comprising:

a) growing the transgenic plant of claim 8; and b) producing said product from or by the plant or a part of the plant, wherein the product comprises the exogenous hydrophobin nucleic acid encoding a protein having an amino acid sequence with at least 90% identity to SEQ ID NO: 42.

14. The method of claim 13, wherein said product is produced from or by harvestable parts of the plant.

15. The method of claim 1, wherein the fungal pathogen is *Phakopsora meibomiae, Phakopsora pachyrhizi*, or a combination thereof.

16. The method of claim 1, wherein the plant is selected from the group consisting of beans, soya, pea, clover, kudzu, lucerne, lentils, lupins, vetches, groundnut, rice, wheat, barley, *arabidopsis*, lentil, banana, canola, cotton, potato, corn, sugar cane, alfalfa, and sugar beet.

17. A method for breeding a fungal resistant plant comprising:

(a) crossing the transgenic plant of claim 8 with a second plant;

(b) obtaining seed from the cross of step (a);

(c) planting said seeds and growing the seeds to plants; and (d) selecting from the plants produced in step (c) plants expressing the hydrophobin protein.

18. The method of claim 1, wherein exogenous nucleic acid encodes a hydrophobin protein with at least 95% identity to SEQ ID NO: 42 over the entire length of SEQ ID NO: 42.

19. The method of claim 1, wherein exogenous nucleic acid encodes a hydrophobin protein with at least 98% identity to SEQ ID NO: 42 over the entire length of SEQ ID NO: 42.

20. The transgenic soybean plant, transgenic soybean plant part, or transgenic soybean plant cell of claim method of claim 8, wherein exogenous nucleic acid encodes a hydrophobin protein comprising an amino acid sequence with at least 95% identity to SEQ ID NO: 42.

21. The transgenic soybean plant, transgenic soybean plant part, or transgenic soybean plant cell of claim method of claim 8, wherein exogenous nucleic acid encodes a hydrophobin protein comprising an amino acid sequence with at least 98% identity to SEQ ID NO: 42.

* * * * *

SEQUENCE LISTING

```
<160> NUMBER OF SEQ ID NOS: 90

<210> SEQ ID NO 1
<211> LENGTH: 408
<212> TYPE: DNA
<213> ORGANISM: Aspergillus nidulans

<400> SEQUENCE: 1
atgcgtttta tcgttagcct tcttgctttc actgctgctg ctactgctac agctttgcca      60
gctagtgctg ctaagaacgc taagcttgct actagtgctg ctttcgctaa gcaagctgag     120
ggaactactt gtaacgtggg atctattgcc tgctgtaact caccagctga gactaacaac     180
gatagccttc ttagtggact tcttggagct ggacttctta acggacttag tggtaacact     240
ggatcagctt gcgctaaggc tagccttatt gatcaacttg gacttcttgc tctcgttgat     300
cacactgaag agggaccagt gtgtaagaat attgtggctt gctgcccaga gggtactact     360
aactgtgttg ctgttgataa cgctggtgct ggaactaagg ctgaataa                  408

<210> SEQ ID NO 2
<211> LENGTH: 135
<212> TYPE: PRT
<213> ORGANISM: Aspergillus nidulans

<400> SEQUENCE: 2

Met Arg Phe Ile Val Ser Leu Leu Ala Phe Thr Ala Ala Ala Thr Ala
```

```
1               5                   10                  15
Thr Ala Leu Pro Ala Ser Ala Ala Lys Asn Ala Lys Leu Ala Thr Ser
                20                  25                  30

Ala Ala Phe Ala Lys Gln Ala Glu Gly Thr Thr Cys Asn Val Gly Ser
                35                  40                  45

Ile Ala Cys Cys Asn Ser Pro Ala Glu Thr Asn Asn Asp Ser Leu Leu
    50                  55                  60

Ser Gly Leu Leu Gly Ala Gly Leu Leu Asn Gly Leu Ser Gly Asn Thr
65                  70                  75                  80

Gly Ser Ala Cys Ala Lys Ala Ser Leu Ile Asp Gln Leu Gly Leu Leu
                85                  90                  95

Ala Leu Val Asp His Thr Glu Glu Gly Pro Val Cys Lys Asn Ile Val
                100                 105                 110

Ala Cys Cys Pro Glu Gly Thr Thr Asn Cys Val Ala Val Asp Asn Ala
                115                 120                 125

Gly Ala Gly Thr Lys Ala Glu
                130                 135
```

<210> SEQ ID NO 3
<211> LENGTH: 471
<212> TYPE: DNA
<213> ORGANISM: Artificial sequence
<220> FEATURE:
<223> OTHER INFORMATION: Coding sequence for hydrophobin rodA

<400> SEQUENCE: 3

```
atgaagttct ccattgctgc cgctgtcgtt gctttcgccg cctccgtcgc ggccctccct      60
cctgcccatg attcccagtt cgctggcaat ggtgttggca acaagggcaa cagcaacgtc    120
aagttccctg tccccgaaaa cgtgaccgtc aagcaggcct ccgacaagtg cggtgaccag    180
gcccagctct cttgctgcaa caaggccacg tacgccggtg acaccacaac cgttgatgag    240
ggtcttctgt ctggtgccct cagcggcctc atcggcgccg gtctggtgc cgaaggtctt     300
ggtctcttcg atcagtgctc caagcttgat gttgctgtcc tcattggcat ccaagatctt    360
gtcaaccaga agtgcaagca aaacattgcc tgctgccaga ctcccccctc agcgcggat     420
ggcaacctta ttggtgtcgg tctcccttgc gttgcccttg gctccatcct c              471
```

<210> SEQ ID NO 4
<211> LENGTH: 157
<212> TYPE: PRT
<213> ORGANISM: Artificial sequence
<220> FEATURE:
<223> OTHER INFORMATION: Hydrophobin rodA

<400> SEQUENCE: 4

```
Met Lys Phe Ser Ile Ala Ala Val Val Ala Phe Ala Ala Ser Val
1               5                   10                  15

Ala Ala Leu Pro Pro Ala His Asp Ser Gln Phe Ala Gly Asn Gly Val
                20                  25                  30

Gly Asn Lys Gly Asn Ser Asn Val Lys Phe Pro Val Pro Glu Asn Val
                35                  40                  45

Thr Val Lys Gln Ala Ser Asp Lys Cys Gly Asp Gln Ala Gln Leu Ser
    50                  55                  60

Cys Cys Asn Lys Ala Thr Tyr Ala Gly Asp Thr Thr Val Asp Glu
65                  70                  75                  80

Gly Leu Leu Ser Gly Ala Leu Ser Gly Leu Ile Gly Ala Gly Ser Gly
                85                  90                  95
```

Ala Glu Gly Leu Gly Leu Phe Asp Gln Cys Ser Lys Leu Asp Val Ala
            100                 105                 110

Val Leu Ile Gly Ile Gln Asp Leu Val Asn Gln Lys Cys Lys Gln Asn
        115                 120                 125

Ile Ala Cys Cys Gln Asn Ser Pro Ser Ser Ala Asp Gly Asn Leu Ile
130                 135                 140

Gly Val Gly Leu Pro Cys Val Ala Leu Gly Ser Ile Leu
145                 150                 155

<210> SEQ ID NO 5
<211> LENGTH: 336
<212> TYPE: DNA
<213> ORGANISM: Artificial sequence
<220> FEATURE:
<223> OTHER INFORMATION: Coding sequence for hydrophobin HypA

<400> SEQUENCE: 5
atgatctctc gcgtccttgt cgctgctctc gtcgctctcc ccgctcttgt tactgcaact    60
cctgctcccg gaaagcctaa agccagcagt cagtgcgacg tcggtgaaat ccattgctgt   120
gacactcagc agactcccga ccacaccagc gccgccgcgt ctggtttgct tggtgttccc   180
atcaaccttg gtgctttcct cggtttcgac tgtaccccca tttccgtcct tggcgtcggt   240
ggcaacaact gtgctgctca gcctgtctgc tgcacaggaa atcaattcac cgcattgatt   300
aacgctcttg actgctctcc tgtcaatgtc aacctc                              336

<210> SEQ ID NO 6
<211> LENGTH: 112
<212> TYPE: PRT
<213> ORGANISM: Artificial sequence
<220> FEATURE:
<223> OTHER INFORMATION: Hydrophobin HypA

<400> SEQUENCE: 6

Met Ile Ser Arg Val Leu Val Ala Ala Leu Val Ala Leu Pro Ala Leu
1               5                   10                  15

Val Thr Ala Thr Pro Ala Pro Gly Lys Pro Lys Ala Ser Ser Gln Cys
            20                  25                  30

Asp Val Gly Glu Ile His Cys Cys Asp Thr Gln Gln Thr Pro Asp His
        35                  40                  45

Thr Ser Ala Ala Ala Ser Gly Leu Leu Gly Val Pro Ile Asn Leu Gly
    50                  55                  60

Ala Phe Leu Gly Phe Asp Cys Thr Pro Ile Ser Val Leu Gly Val Gly
65                  70                  75                  80

Gly Asn Asn Cys Ala Ala Gln Pro Val Cys Cys Thr Gly Asn Gln Phe
                85                  90                  95

Thr Ala Leu Ile Asn Ala Leu Asp Cys Ser Pro Val Asn Val Asn Leu
            100                 105                 110

<210> SEQ ID NO 7
<211> LENGTH: 357
<212> TYPE: DNA
<213> ORGANISM: Artificial sequence
<220> FEATURE:
<223> OTHER INFORMATION: Coding sequence for hydrophobin HypB

<400> SEQUENCE: 7
atggtcagca cgttcatcac tgtcgcaaag acccttctcg tcgcgctcct cttcgtcaat    60
atcaatatcg tcgttggtac tgcaactacc ggcaagcatt gtagcaccgg tcctatcgag   120

```
tgctgcaagc aggtcatgga ttctaagagc cctcaggcta cggagcttct tacgaagaat    180
ggccttggcc tgggtgtcct tgctggcgtg aagggtcttg ttggcgcgaa ttgcagccct    240
atcacggcaa ttggtattgg ctccggcagc caatgctctg ccagaccgt ttgctgccag    300 aataataatt tcaacggtgt tgtcgctatt ggttgcactc ccattaatgc caatgtg      357
```

<210> SEQ ID NO 8
<211> LENGTH: 64
<212> TYPE: PRT
<213> ORGANISM: Artificial sequence
<220> FEATURE:
<223> OTHER INFORMATION: Hydrophobin HypB

<400> SEQUENCE: 8

Met Val Ser Thr Phe Ile Thr Val Ala Lys Thr Leu Leu Val Ala Leu
1               5                   10                  15

Leu Phe Val Asn Ile Asn Ile Val Val Gly Thr Ala Thr Thr Gly Lys
            20                  25                  30

His Cys Ser Thr Gly Pro Ile Glu Cys Cys Lys Gln Val Met Asp Ser
        35                  40                  45

Lys Ser Pro Gln Ala Thr Glu Leu Leu Thr Lys Asn Gly Leu Gly Leu
    50                  55                  60

<210> SEQ ID NO 9
<211> LENGTH: 408
<212> TYPE: DNA
<213> ORGANISM: Artificial sequence
<220> FEATURE:
<223> OTHER INFORMATION: Coding sequence for Hydrophobin Sc3

<400> SEQUENCE: 9

```
atgttcgccc gtctccccgt cgtgttcctc tacgccttcg tcgcgttcgg cgccctcgtc     60
gctgccctcc caggtggcca cccgggcacg accacgccgc cggttacgac gacggtgacg    120
gtgaccacgc cgccctcgac gacgaccatc gccgccggtg gcacgtgtac tacggggtcg    180
ctctcttgct gcaaccaggt tcaatcggcg agcagcagcc ctgttaccgc cctcctcggc    240
ctgctcggca ttgtcctcag cgacctcaac gttctcgttg gcatcagctg ctctcccctc    300
actgtcatcg gtgtcggagg cagcggctgt tcggcgcaga ccgtctgctg cgaaaacacc    360
caattcaacg gctgatcaa catcggttgc acccccatca acatcctc                 408
```

<210> SEQ ID NO 10
<211> LENGTH: 136
<212> TYPE: PRT
<213> ORGANISM: Artificial sequence
<220> FEATURE:
<223> OTHER INFORMATION: Hydrophobin Sc3

<400> SEQUENCE: 10

Met Phe Ala Arg Leu Pro Val Val Phe Leu Tyr Ala Phe Val Ala Phe
1               5                   10                  15

Gly Ala Leu Val Ala Ala Leu Pro Gly Gly His Pro Gly Thr Thr Thr
            20                  25                  30

Pro Pro Val Thr Thr Thr Val Thr Val Thr Pro Pro Ser Thr Thr
        35                  40                  45

Thr Ile Ala Ala Gly Gly Thr Cys Thr Thr Gly Ser Leu Ser Cys Cys
    50                  55                  60

Asn Gln Val Gln Ser Ala Ser Ser Ser Pro Val Thr Ala Leu Leu Gly
65                  70                  75                  80

Leu Leu Gly Ile Val Leu Ser Asp Leu Asn Val Leu Gly Ile Ser
            85                  90                  95

Cys Ser Pro Leu Thr Val Ile Gly Val Gly Ser Gly Cys Ser Ala
            100                 105                 110

Gln Thr Val Cys Cys Glu Asn Thr Gln Phe Asn Gly Leu Ile Asn Ile
        115                 120                 125

Gly Cys Thr Pro Ile Asn Ile Leu
    130                 135

<210> SEQ ID NO 11
<211> LENGTH: 483
<212> TYPE: DNA
<213> ORGANISM: Artificial sequence
<220> FEATURE:
<223> OTHER INFORMATION: Coding sequence for hydrophobin BASF1

<400> SEQUENCE: 11

```
atgaagttct ccgtctccgc cgccgtcctc gccttcgccg cctccgtcgc cgccctccct      60
cagcacgact ccgccgccgg caacggcaac ggcgtcggca acaagttccc tgtccctgac     120
gacgtcaccg tcaagcaggc caccgacaag tgcggcgacc aggcccagct ctcctgctgc     180
aacaaggcca cctacgccgg cgacgtcctc accgacatcg acgagggcat cctcgccggc     240
ctcctcaaga acctcatcgg cggcggctcc ggctccgagg gctcggcct cttcgaccag     300 tgcgtcaagc tcgacctcca gatctccgtc atcggcatcc ctatccagga cctcctcaac     360
caggtcaaca gcagtgcaa gcagaacatc gcctgctgcc agaactcccc ttccgacgcc     420
accggctccc tcgtcaacct cggcctcggc aacccttgca tccctgtctc cctcctccat     480
atg                                                                   483
```

<210> SEQ ID NO 12
<211> LENGTH: 161
<212> TYPE: PRT
<213> ORGANISM: Artificial sequence
<220> FEATURE:
<223> OTHER INFORMATION: Hydrophobin BASF1

<400> SEQUENCE: 12

Met Lys Phe Ser Val Ser Ala Val Leu Ala Phe Ala Ala Ser Val
1               5                   10                  15

Ala Ala Leu Pro Gln His Asp Ser Ala Ala Gly Asn Gly Asn Gly Val
            20                  25                  30

Gly Asn Lys Phe Pro Val Pro Asp Asp Val Thr Val Lys Gln Ala Thr
        35                  40                  45

Asp Lys Cys Gly Asp Gln Ala Gln Leu Ser Cys Cys Asn Lys Ala Thr
    50                  55                  60

Tyr Ala Gly Asp Val Leu Thr Asp Ile Asp Glu Gly Ile Leu Ala Gly
65                  70                  75                  80

Leu Leu Lys Asn Leu Ile Gly Gly Gly Ser Gly Ser Glu Gly Leu Gly
            85                  90                  95

Leu Phe Asp Gln Cys Val Lys Leu Asp Leu Gln Ile Ser Val Ile Gly
            100                 105                 110

Ile Pro Ile Gln Asp Leu Leu Asn Gln Val Asn Lys Gln Cys Lys Gln
        115                 120                 125

Asn Ile Ala Cys Cys Gln Asn Ser Pro Ser Asp Ala Thr Gly Ser Leu
    130                 135                 140

Val Asn Leu Gly Leu Gly Asn Pro Cys Ile Pro Val Ser Leu Leu His 145             150             155             160

Met

<210> SEQ ID NO 13
<211> LENGTH: 465
<212> TYPE: DNA
<213> ORGANISM: Artificial sequence
<220> FEATURE:
<223> OTHER INFORMATION: Coding sequence for hydrophobin BASF2

<400> SEQUENCE: 13

```
atgaagttct ccgtctccgc cgccgtcctc gccttcgccg cctccgtcgc cgccctccct      60
cagcacgact ccgccgccgg caacggcaac ggcgtcggca acaagttccc tgtccctgac     120
gacgtcaccg tcaagcaggc caccgacaag tgcggcgacc aggcccagct tcctgctgc      180
aacaaggcca cctacgccgg cgacgtcacc gacatcgacg agggcatcct cgccggcctc     240
ctcaagaacc tcatcggcgg cggctccggc tccgagggcc tcggcctctt cgaccagtgc     300
gtcaagctcg acctccagat ctccgtcatc ggcatcccta tccaggacct cctcaaccag     360
cagtgcaagc agaacatcgc ctgctgccag aactcccctt ccgacgccac cggctccctc     420
gtcaacctcg gcaaccccttg catccctgtc tccctcctcc atatg                    465
```

<210> SEQ ID NO 14
<211> LENGTH: 155
<212> TYPE: PRT
<213> ORGANISM: Artificial sequence
<220> FEATURE:
<223> OTHER INFORMATION: Hydrophobin BASF2

<400> SEQUENCE: 14

Met Lys Phe Ser Val Ser Ala Val Leu Ala Phe Ala Ala Ser Val
1               5                   10                  15

Ala Ala Leu Pro Gln His Asp Ser Ala Ala Gly Asn Gly Asn Gly Val
            20                  25                  30

Gly Asn Lys Phe Pro Val Pro Asp Asp Val Thr Val Lys Gln Ala Thr
        35                  40                  45

Asp Lys Cys Gly Asp Gln Ala Gln Leu Ser Cys Cys Asn Lys Ala Thr
50                  55                  60

Tyr Ala Gly Asp Val Thr Asp Ile Asp Glu Gly Ile Leu Ala Gly Leu
65                  70                  75                  80

Leu Lys Asn Leu Ile Gly Gly Gly Ser Gly Ser Glu Gly Leu Gly Leu
                85                  90                  95

Phe Asp Gln Cys Val Lys Leu Asp Leu Gln Ile Ser Val Ile Gly Ile
            100                 105                 110

Pro Ile Gln Asp Leu Leu Asn Gln Gln Cys Lys Gln Asn Ile Ala Cys
        115                 120                 125

Cys Gln Asn Ser Pro Ser Asp Ala Thr Gly Ser Leu Val Asn Leu Gly
    130                 135                 140

Asn Pro Cys Ile Pro Val Ser Leu Leu His Met
145                 150                 155

<210> SEQ ID NO 15
<211> LENGTH: 117
<212> TYPE: DNA
<213> ORGANISM: Bacillus subtilis

<400> SEQUENCE: 15

```
gctcaaactg gaactgaaag ggttaagagg ggtatggctg aaatgcaaaa gggtggtgtg      60
```

```
attatggacg tgatcaacgc tgagcaggct aagattgctg aagaggctgg tgctgtt        117
```

<210> SEQ ID NO 16
<211> LENGTH: 39
<212> TYPE: PRT
<213> ORGANISM: Bacillus subtilis

<400> SEQUENCE: 16

Ala Gln Thr Gly Thr Glu Arg Val Lys Arg Gly Met Ala Glu Met Gln
1               5                   10                  15

Lys Gly Gly Val Ile Met Asp Val Ile Asn Ala Glu Gln Ala Lys Ile
            20                  25                  30

Ala Glu Glu Ala Gly Ala Val
        35

<210> SEQ ID NO 17
<211> LENGTH: 882
<212> TYPE: DNA
<213> ORGANISM: Artificial sequence
<220> FEATURE:
<223> OTHER INFORMATION: Coding sequence for fusion partner yaad

<400> SEQUENCE: 17

```
atggctcaaa caggtactga acgtgtaaaa cgcggaatgg cagaaatgca aaaaggcggc        60
gtcatcatgg acgtcatcaa tgcggaacaa gcgaaaatcg ctgaagaagc tggagctgtc       120
gctgtaatgg cgctagaacg tgtgccagca gatattcgcg cggctggagg agttgcccgt       180
atggctgacc ctacaatcgt ggaagaagta atgaatgcag tatctatccc ggtaatggca       240
aaagcgcgta tcggacatat tgttgaagcg cgtgtgcttg aagctatggg tgttgactat       300
attgatgaaa gtgaagttct gacgccggct gacgaagaat tcatttaaa taaaaatgaa       360
tacacagttc cttttgtctg tggctgccgt gatcttggtg aagcaacacg ccgtattgcg       420
gaaggtgctt ctatgcttcg cacaaaaggt gagcctggaa caggtaatat tgttgaggct       480
gttcgccata tgcgtaaagt taacgctcaa gtgcgcaaag tagttgcgat gagtgaggat       540
gagctaatga cagaagcgaa aaacctaggt gctccttacg agcttcttct tcaaattaaa       600
aaagacggca gcttcctgt cgttaacttt gccgctggcg gcgtagcaac tccagctgat       660
gctgctctca tgatgcagct tggtgctgac ggagtatttg ttggttctgg tatttttaaa       720
tcagacaacc ctgctaaatt tgcgaaagca attgtggaag caacaactca ctttactgat       780
tacaaattaa tcgctgagtt gtcaaaagag cttggtactg caatgaaagg gattgaaatc       840
tcaaacttac ttccagaaca gcgtatgcaa gaacgcggct gg                          882
```

<210> SEQ ID NO 18
<211> LENGTH: 294
<212> TYPE: PRT
<213> ORGANISM: Artificial sequence
<220> FEATURE:
<223> OTHER INFORMATION: Fusion partner yaad

<400> SEQUENCE: 18

Met Ala Gln Thr Gly Thr Glu Arg Val Lys Arg Gly Met Ala Glu Met
1               5                   10                  15

Gln Lys Gly Gly Val Ile Met Asp Val Ile Asn Ala Glu Gln Ala Lys
            20                  25                  30

Ile Ala Glu Glu Ala Gly Ala Val Ala Val Met Ala Leu Glu Arg Val
        35                  40                  45

```
Pro Ala Asp Ile Arg Ala Ala Gly Gly Val Ala Arg Met Ala Asp Pro
    50                  55                  60
Thr Ile Val Glu Glu Val Met Asn Ala Val Ser Ile Pro Val Met Ala
65                  70                  75                  80
Lys Ala Arg Ile Gly His Ile Val Glu Ala Arg Val Leu Glu Ala Met
                85                  90                  95
Gly Val Asp Tyr Ile Asp Glu Ser Glu Val Leu Thr Pro Ala Asp Glu
            100                 105                 110
Glu Phe His Leu Asn Lys Asn Glu Tyr Thr Val Pro Phe Val Cys Gly
        115                 120                 125
Cys Arg Asp Leu Gly Glu Ala Thr Arg Arg Ile Ala Glu Gly Ala Ser
    130                 135                 140
Met Leu Arg Thr Lys Gly Glu Pro Gly Thr Gly Asn Ile Val Glu Ala
145                 150                 155                 160
Val Arg His Met Arg Lys Val Asn Ala Gln Val Arg Lys Val Val Ala
                165                 170                 175
Met Ser Glu Asp Glu Leu Met Thr Glu Ala Lys Asn Leu Gly Ala Pro
            180                 185                 190
Tyr Glu Leu Leu Leu Gln Ile Lys Lys Asp Gly Lys Leu Pro Val Val
        195                 200                 205
Asn Phe Ala Ala Gly Gly Val Ala Thr Pro Ala Asp Ala Ala Leu Met
    210                 215                 220
Met Gln Leu Gly Ala Asp Gly Val Phe Val Gly Ser Gly Ile Phe Lys
225                 230                 235                 240
Ser Asp Asn Pro Ala Lys Phe Ala Lys Ala Ile Val Glu Ala Thr Thr
                245                 250                 255
His Phe Thr Asp Tyr Lys Leu Ile Ala Glu Leu Ser Lys Glu Leu Gly
            260                 265                 270
Thr Ala Met Lys Gly Ile Glu Ile Ser Asn Leu Leu Pro Glu Gln Arg
        275                 280                 285
Met Gln Glu Arg Gly Trp
    290

<210> SEQ ID NO 19
<211> LENGTH: 591
<212> TYPE: DNA
<213> ORGANISM: Artificial sequence
<220> FEATURE:
<223> OTHER INFORMATION: Coding sequence for fusion partner yaae

<400> SEQUENCE: 19
atgggattaa caataggtgt actaggactt caaggagcag ttagagagca catccatgcg      60
attgaagcat gcggcgcggc tggtcttgtc gtaaaacgtc cggagcagct gaacgaagtt     120
gacgggttga ttttgccggg cggtgagagc acgacgatgc gccgtttgat cgatacgtat     180
caattcatgg agccgcttcg tgaattcgct gctcagggca aaccgatgtt tggaacatgt     240
gccggattaa ttatattagc aaaagaaatt gccggttcag ataatcctca tttaggtctt     300
ctgaatgtgg ttgtagaacg taattcattt ggccggcagg ttgacagctt tgaagctgat     360
ttaacaatta aaggcttgga cgagcctttt actggggtat tcatccgtgc tccgcatatt     420
ttagaagctg gtgaaaatgt tgaagttcta tcggagcata atggtcgtat tgtagccgcg     480
aaacagggc aattccttgg ctgctcattc catccggagc tgacagaaga tcaccgagtg     540
acgcagctgt tgttgaaat ggttgaggaa tataagcaaa aggcacttgt a              591
```

<210> SEQ ID NO 20
<211> LENGTH: 197
<212> TYPE: PRT
<213> ORGANISM: Artificial sequence
<220> FEATURE:
<223> OTHER INFORMATION: Fusion partner yaae

<400> SEQUENCE: 20

Met Gly Leu Thr Ile Gly Val Leu Gly Leu Gln Gly Ala Val Arg Glu
1               5                   10                  15

His Ile His Ala Ile Glu Ala Cys Gly Ala Ala Gly Leu Val Val Lys
            20                  25                  30

Arg Pro Glu Gln Leu Asn Glu Val Asp Gly Leu Ile Leu Pro Gly Gly
        35                  40                  45

Glu Ser Thr Thr Met Arg Arg Leu Ile Asp Thr Tyr Gln Phe Met Glu
    50                  55                  60

Pro Leu Arg Glu Phe Ala Ala Gln Gly Lys Pro Met Phe Gly Thr Cys
65                  70                  75                  80

Ala Gly Leu Ile Ile Leu Ala Lys Glu Ile Ala Gly Ser Asp Asn Pro
                85                  90                  95

His Leu Gly Leu Leu Asn Val Val Val Glu Arg Asn Ser Phe Gly Arg
            100                 105                 110

Gln Val Asp Ser Phe Glu Ala Asp Leu Thr Ile Lys Gly Leu Asp Glu
        115                 120                 125

Pro Phe Thr Gly Val Phe Ile Arg Ala Pro His Ile Leu Glu Ala Gly
    130                 135                 140

Glu Asn Val Glu Val Leu Ser Glu His Asn Gly Arg Ile Val Ala Ala
145                 150                 155                 160

Lys Gln Gly Gln Phe Leu Gly Cys Ser Phe His Pro Glu Leu Thr Glu
                165                 170                 175

Asp His Arg Val Thr Gln Leu Phe Val Glu Met Val Glu Glu Tyr Lys
            180                 185                 190

Gln Lys Ala Leu Val
        195

<210> SEQ ID NO 21
<211> LENGTH: 384
<212> TYPE: DNA
<213> ORGANISM: Escherichia coli

<400> SEQUENCE: 21
atgttacacc aacaacgaaa ccaacacgcc aggcttattc ctgtggagtt atatatgagc      60
gataaaatta ttcacctgac tgacgacagt tttgacacgg atgtactcaa agcggacggg     120
gcgatcctcg tcgatttctg ggcagagtgg tgcggtccgt gcaaaatgat cgcccccgatt    180 ctggatgaaa tcgctgacga atatcagggc aaactgaccg ttgcaaaact gaacatcgat     240
caaaaccctg gcactgcgcc gaaatatggc atccgtggta tcccgactct gctgctgttc     300
aaaaacggtg aagtggcggc aaccaaagtg ggtgcactgt ctaaaggtca gttgaaagag     360
ttcctcgacg ctaacctggc gtaa                                            384

<210> SEQ ID NO 22
<211> LENGTH: 127
<212> TYPE: PRT
<213> ORGANISM: Escherichia coli

<400> SEQUENCE: 22

Met Leu His Gln Gln Arg Asn Gln His Ala Arg Leu Ile Pro Val Glu

```
              1               5                  10                 15
Leu Tyr Met Ser Asp Lys Ile Ile His Leu Thr Asp Asp Ser Phe Asp
                    20                 25                 30

Thr Asp Val Leu Lys Ala Asp Gly Ala Ile Leu Val Asp Phe Trp Ala
                35                 40                 45

Glu Trp Cys Gly Pro Cys Lys Met Ile Ala Pro Ile Leu Asp Glu Ile
        50                 55                 60

Ala Asp Glu Tyr Gln Gly Lys Leu Thr Val Ala Lys Leu Asn Ile Asp
65                  70                 75                 80

Gln Asn Pro Gly Thr Ala Pro Lys Tyr Gly Ile Arg Gly Ile Pro Thr
                    85                 90                 95

Leu Leu Leu Phe Lys Asn Gly Glu Val Ala Ala Thr Lys Val Gly Ala
                100                105                110

Leu Ser Lys Gly Gln Leu Lys Glu Phe Leu Asp Ala Asn Leu Ala
            115                120                125
```

<210> SEQ ID NO 23
<211> LENGTH: 60
<212> TYPE: DNA
<213> ORGANISM: Artificial sequence
<220> FEATURE:
<223> OTHER INFORMATION: Coding sequence for secretion signal sequence

<400> SEQUENCE: 23
atgaagacta acctgttcct cttcctgatc ttctcacttt tgcttagcct tagctcagct    60

<210> SEQ ID NO 24
<211> LENGTH: 20
<212> TYPE: PRT
<213> ORGANISM: Artificial sequence
<220> FEATURE:
<223> OTHER INFORMATION: Secretion signal sequence

<400> SEQUENCE: 24

```
Met Lys Thr Asn Leu Phe Leu Phe Leu Ile Phe Ser Leu Leu Leu Ser
1               5                   10                  15

Leu Ser Ser Ala
            20
```

<210> SEQ ID NO 25
<211> LENGTH: 27
<212> TYPE: DNA
<213> ORGANISM: Artificial sequence
<220> FEATURE:
<223> OTHER INFORMATION: Coding sequence for His tag

<400> SEQUENCE: 25
ggtagtcatc atcatcacca tcactaa                                        27

<210> SEQ ID NO 26
<211> LENGTH: 8
<212> TYPE: PRT
<213> ORGANISM: Artificial sequence
<220> FEATURE:
<223> OTHER INFORMATION: His tag

<400> SEQUENCE: 26

```
Gly Ser His His His His His His
1               5
```

<210> SEQ ID NO 27
<211> LENGTH: 597

<212> TYPE: DNA
<213> ORGANISM: Artificial sequence
<220> FEATURE:
<223> OTHER INFORMATION: Coding sequence for fusion protein secretion
      signal, synthase subunit Pdx1 (39aa), Xa protease site, and
      hydrophobin

<400> SEQUENCE: 27

```
atgaagacta acctgttcct cttcctgatc ttctcacttt tgcttagcct tagctcagct    60
gctcaaactg gaactgaaag ggttaagagg ggtatggctg aaatgcaaaa gggtggtgtg   120
attatggacg tgatcaacgc tgagcaggct aagattgctg aagaggctgg tgctgttatt   180
gagggtagaa tgcgttttat cgttagcctt cttgctttca ctgctgctgc tactgctaca   240
gctttgccag ctagtgctgc taagaacgct aagcttgcta ctagtgctgc tttcgctaag   300
caagctgagg gaactacttg taacgtggga tctattgcct gctgtaactc accagctgag   360
actaacaacg atagccttct tagtggactt cttggagctg gacttcttaa cggacttagt   420
ggtaacactg gatcagcttg cgctaaggct agccttattg atcaacttgg acttcttgct   480
ctcgttgatc acactgaaga gggaccagtg tgtaagaata ttgtggcttg ctgcccagag   540
ggtactacta actgtgttgc tgttgataac gctggtgctg gaactaaggc tgaataa     597
```

<210> SEQ ID NO 28
<211> LENGTH: 198
<212> TYPE: PRT
<213> ORGANISM: Artificial sequence
<220> FEATURE:
<223> OTHER INFORMATION: Fusion protein secretion signal, synthase
      subunit Pdx1 (39aa), Xa protease site, and hydrophobin

<400> SEQUENCE: 28

```
Met Lys Thr Asn Leu Phe Leu Phe Leu Ile Phe Ser Leu Leu Ser
 1               5                  10                  15

Leu Ser Ser Ala Ala Gln Thr Gly Thr Glu Arg Val Lys Arg Gly Met
                20                  25                  30

Ala Glu Met Gln Lys Gly Gly Val Ile Met Asp Val Ile Asn Ala Glu
            35                  40                  45

Gln Ala Lys Ile Ala Glu Glu Ala Gly Ala Val Ile Glu Gly Arg Met
        50                  55                  60

Arg Phe Ile Val Ser Leu Leu Ala Phe Thr Ala Ala Thr Ala Thr
65                  70                  75                  80

Ala Leu Pro Ala Ser Ala Ala Lys Asn Ala Lys Leu Ala Thr Ser Ala
                85                  90                  95

Ala Phe Ala Lys Gln Ala Glu Gly Thr Thr Cys Asn Val Gly Ser Ile
            100                 105                 110

Ala Cys Cys Asn Ser Pro Ala Glu Thr Asn Asn Asp Ser Leu Leu Ser
        115                 120                 125

Gly Leu Leu Gly Ala Gly Leu Leu Asn Gly Leu Ser Gly Asn Thr Gly
    130                 135                 140

Ser Ala Cys Ala Lys Ala Ser Leu Ile Asp Gln Leu Gly Leu Leu Ala
145                 150                 155                 160

Leu Val Asp His Thr Glu Glu Gly Pro Val Cys Lys Asn Ile Val Ala
                165                 170                 175

Cys Cys Pro Glu Gly Thr Thr Asn Cys Val Ala Val Asp Asn Ala Gly
            180                 185                 190

Ala Gly Thr Lys Ala Glu
        195
```

<210> SEQ ID NO 29
<211> LENGTH: 621
<212> TYPE: DNA
<213> ORGANISM: Artificial sequence
<220> FEATURE:
<223> OTHER INFORMATION: Coding sequence for fusion protein with
      secretion signal, synthase subunit Pdx1 (39aa), Xa protease site,
      hydrophobin, his-tag

<400> SEQUENCE: 29

```
atgaagacta acctgttcct cttcctgatc ttctcacttt tgcttagcct tagctcagct      60
gctcaaactg gaactgaaag ggttaagagg ggtatggctg aaatgcaaaa gggtggtgtg     120
attatggacg tgatcaacgc tgagcaggct aagattgctg aagaggctgg tgctgttatt     180
gagggtagaa tgcgttttat cgttagcctt cttgctttca ctgctgctgc tactgctaca     240
gctttgccag ctagtgctgc taagaacgct aagcttgcta ctagtgctgc tttcgctaag     300
caagctgagg gaactacttg taacgtggga tctattgcct gctgtaactc accagctgag     360
actaacaacg atagccttct tagtggactt cttggagctg gacttcttaa cggacttagt     420
ggtaacactg gatcagcttg cgctaaggct agccttattg atcaacttgg acttcttgct     480
ctcgttgatc acactgaaga gggaccagtg tgtaagaata ttgtggcttg ctgcccagag     540
ggtactacta actgtgttgc tgttgataac gctggtgctg aactaaggc tgaaggtagt     600 catcatcatc accatcacta a                                                621
```

<210> SEQ ID NO 30
<211> LENGTH: 206
<212> TYPE: PRT
<213> ORGANISM: Artificial sequence
<220> FEATURE:
<223> OTHER INFORMATION: Fusion protein with secretion signal, synthase
      subunit Pdx1 (39aa), Xa protease site, hydrophobin, his-tag

<400> SEQUENCE: 30

Met Lys Thr Asn Leu Phe Leu Phe Leu Ile Phe Ser Leu Leu Leu Ser
1               5                   10                  15

Leu Ser Ser Ala Ala Gln Thr Gly Thr Glu Arg Val Lys Arg Gly Met
            20                  25                  30

Ala Glu Met Gln Lys Gly Gly Val Ile Met Asp Val Ile Asn Ala Glu
        35                  40                  45

Gln Ala Lys Ile Ala Glu Glu Ala Gly Ala Val Ile Glu Gly Arg Met
    50                  55                  60

Arg Phe Ile Val Ser Leu Leu Ala Phe Thr Ala Ala Ala Thr Ala Thr
65                  70                  75                  80

Ala Leu Pro Ala Ser Ala Ala Lys Asn Ala Lys Leu Ala Thr Ser Ala
                85                  90                  95

Ala Phe Ala Lys Gln Ala Glu Gly Thr Thr Cys Asn Val Gly Ser Ile
            100                 105                 110

Ala Cys Cys Asn Ser Pro Ala Glu Thr Asn Asn Asp Ser Leu Leu Ser
        115                 120                 125

Gly Leu Leu Gly Ala Gly Leu Leu Asn Gly Leu Ser Gly Asn Thr Gly
    130                 135                 140

Ser Ala Cys Ala Lys Ala Ser Leu Ile Asp Gln Leu Gly Leu Leu Ala
145                 150                 155                 160

Leu Val Asp His Thr Glu Glu Gly Pro Val Cys Lys Asn Ile Val Ala
                165                 170                 175

Cys Cys Pro Glu Gly Thr Thr Asn Cys Val Ala Val Asp Asn Ala Gly

```
                180               185              190
Ala Gly Thr Lys Ala Glu Gly Ser His His His His His His
         195              200             205

<210> SEQ ID NO 31
<211> LENGTH: 1329
<212> TYPE: DNA
<213> ORGANISM: Artificial sequence
<220> FEATURE:
<223> OTHER INFORMATION: Coding sequence for fusion protein yaad, Xa,
      dewA, his tag

<400> SEQUENCE: 31
atggctcaaa caggtactga acgtgtaaaa cgcggaatgg cagaaatgca aaaaggcggc      60
gtcatcatgg acgtcatcaa tgcggaacaa gcgaaaatcg ctgaagaagc tggagctgtc    120
gctgtaatgg cgctagaacg tgtgccagca gatattcgcg cggctggagg agttgcccgt    180
atggctgacc ctacaatcgt ggaagaagta atgaatgcag tatctatccc ggtaatggca    240
aaagcgcgta tcggacatat tgttgaagcg cgtgtgcttg aagctatggg tgttgactat    300
attgatgaaa gtgaagttct gacgccggct gacgaagaat tcattttaaa taaaaatgaa    360
tacacagttc cttttgtctg tggctgccgt gatcttggtg aagcaacacg ccgtattgcg    420
gaaggtgctt ctatgcttcg cacaaaaggt gagcctggaa caggtaatat tgttgaggct    480
gttcgccata tgcgtaaagt taacgctcaa gtgcgcaaag tagttgcgat gagtgaggat    540
gagctaatga cagaagcgaa aaacctaggt gctccttacg agcttcttct tcaaattaaa    600
aaagacggca gcttcctgtc gttaactttt gccgctggcg cgtagcaac tccagctgat    660 gctgctctca tgatgcagct tggtgctgac ggagtatttg ttggttctgg tattttaaa     720 tcagacaacc ctgctaaatt tgcgaaagca attgtggaag caacaactca ctttactgat    780
tacaaattaa tcgctgagtt gtcaaagag cttggtactg caatgaaagg gattgaaatc     840
tcaaacttac ttccagaaca gcgtatgcaa gaacgcggct ggagatccat tgaaggccgc    900
atgcgcttca tcgtctctct cctcgccttc actgccgcgg ccaccgcgac cgccctcccg    960
gcctctgccg caaagaacgc gaagctggcc acctcggcgg ccttcgccaa gcaggctgaa   1020
ggcaccacct gcaatgtcgg ctcgatcgct tgctgcaact ccccgctga ccaacaac     1080 gacagtctgt tgagcggtct gctcggtgct ggccttctca acgggctctc gggcaacact   1140
ggcagcgcct gcgccaaggc gagcttgatt gaccagctgg tctgctcgc tctcgtcgac   1200 cacactgagg aaggccccgt ctgcaagaac atcgtcgctt gctgccctga gggaaccacc   1260
aactgtgttg ccgtcgacaa cgctggcgct ggtaccaagg ctgagggatc tcatcaccat   1320
caccatcac                                                           1329

<210> SEQ ID NO 32
<211> LENGTH: 443
<212> TYPE: PRT
<213> ORGANISM: Artificial sequence
<220> FEATURE:
<223> OTHER INFORMATION: Fusion protein yaad, Xa, dewA, his tag

<400> SEQUENCE: 32

Met Ala Gln Thr Gly Thr Glu Arg Val Lys Arg Gly Met Ala Glu Met
 1               5                  10                  15

Gln Lys Gly Gly Val Ile Met Asp Val Ile Asn Ala Glu Gln Ala Lys
             20                  25                  30

Ile Ala Glu Glu Ala Gly Ala Val Ala Val Met Ala Leu Glu Arg Val
```

```
            35                  40                  45
Pro Ala Asp Ile Arg Ala Ala Gly Gly Val Ala Arg Met Ala Asp Pro
         50                  55                  60
Thr Ile Val Glu Glu Val Met Asn Ala Val Ser Ile Pro Val Met Ala
 65                  70                  75                  80
Lys Ala Arg Ile Gly His Ile Val Glu Ala Arg Val Leu Glu Ala Met
                 85                  90                  95
Gly Val Asp Tyr Ile Asp Glu Ser Glu Val Leu Thr Pro Ala Asp Glu
                100                 105                 110
Glu Phe His Leu Asn Lys Asn Glu Tyr Thr Val Pro Phe Val Cys Gly
                115                 120                 125
Cys Arg Asp Leu Gly Glu Ala Thr Arg Arg Ile Ala Glu Gly Ala Ser
            130                 135                 140
Met Leu Arg Thr Lys Gly Glu Pro Gly Thr Gly Asn Ile Val Glu Ala
145                 150                 155                 160
Val Arg His Met Arg Lys Val Asn Ala Gln Val Arg Lys Val Val Ala
                165                 170                 175
Met Ser Glu Asp Glu Leu Met Thr Glu Ala Lys Asn Leu Gly Ala Pro
            180                 185                 190
Tyr Glu Leu Leu Leu Gln Ile Lys Lys Asp Gly Lys Leu Pro Val Val
                195                 200                 205
Asn Phe Ala Ala Gly Gly Val Ala Thr Pro Ala Asp Ala Ala Leu Met
            210                 215                 220
Met Gln Leu Gly Ala Asp Gly Val Phe Val Gly Ser Gly Ile Phe Lys
225                 230                 235                 240
Ser Asp Asn Pro Ala Lys Phe Ala Lys Ala Ile Val Glu Ala Thr Thr
                245                 250                 255
His Phe Thr Asp Tyr Lys Leu Ile Ala Glu Leu Ser Lys Glu Leu Gly
                260                 265                 270
Thr Ala Met Lys Gly Ile Glu Ile Ser Asn Leu Leu Pro Glu Gln Arg
            275                 280                 285
Met Gln Glu Arg Gly Trp Arg Ser Ile Glu Gly Arg Met Arg Phe Ile
        290                 295                 300
Val Ser Leu Leu Ala Phe Thr Ala Ala Thr Ala Thr Ala Leu Pro
305                 310                 315                 320
Ala Ser Ala Ala Lys Asn Ala Lys Leu Ala Thr Ser Ala Ala Phe Ala
                325                 330                 335
Lys Gln Ala Glu Gly Thr Thr Cys Asn Val Gly Ser Ile Ala Cys Cys
                340                 345                 350
Asn Ser Pro Ala Glu Thr Asn Asn Asp Ser Leu Leu Ser Gly Leu Leu
            355                 360                 365
Gly Ala Gly Leu Leu Asn Gly Leu Ser Gly Asn Thr Gly Ser Ala Cys
        370                 375                 380
Ala Lys Ala Ser Leu Ile Asp Gln Leu Gly Leu Leu Ala Leu Val Asp
385                 390                 395                 400
His Thr Glu Glu Gly Pro Val Cys Lys Asn Ile Val Ala Cys Cys Pro
                405                 410                 415
Glu Gly Thr Thr Asn Cys Val Ala Val Asp Asn Ala Gly Ala Gly Thr
            420                 425                 430
Lys Ala Glu Gly Ser His His His His His His
            435                 440

<210> SEQ ID NO 33
```

<211> LENGTH: 1395
<212> TYPE: DNA
<213> ORGANISM: Artificial sequence
<220> FEATURE:
<223> OTHER INFORMATION: Coding sequence for fusion protein yaad, Xa, rodA, his tag

<400> SEQUENCE: 33

```
atggctcaaa caggtactga acgtgtaaaa cgcggaatgg cagaaatgca aaaaggcggc      60
gtcatcatgg acgtcatcaa tgcggaacaa gcgaaaatcg ctgaagaagc tggagctgtc     120
gctgtaatgg cgctagaacg tgtgccagca gatattcgcg cggctggagg agttgcccgt     180
atggctgacc ctacaatcgt ggaagaagta atgaatgcag tatctatccc ggtaatggca     240
aaagcgcgta tcggacatat tgttgaagcg cgtgtgcttg aagctatggg tgttgactat     300
attgatgaaa gtgaagttct gacgccggct gacgaagaat tcatttaaa taaaaatgaa      360
tacacagttc cttttgtctg tggctgccgt gatcttggtg aagcaacacg ccgtattgcg     420
gaaggtgctt ctatgcttcg cacaaaaggt gagcctggaa caggtaatat tgttgaggct     480
gttcgccata tgcgtaaagt taacgctcaa gtgcgcaaag tagttgcgat gagtgaggat     540
gagctaatga cagaagcgaa aaacctaggt gctccttacg agcttcttct tcaaattaaa     600
aaagacggca agcttcctgt cgttaacttt gccgctggcg gcgtagcaac tccagctgat     660
gctgctctca tgatgcagct tggtgctgac ggagtatttg ttggttctgg tattttttaaa   720
tcagacaacc ctgctaaatt tgcgaaagca attgtggaag caacaactca ctttactgat     780
tacaaattaa tcgctgagtt gtcaaaagag cttggtactg caatgaaagg gattgaaatc     840
tcaaacttac ttccagaaca gcgtatgcaa gaacgcggct ggagatctat tgaaggccgc     900
atgaagttct ccattgctgc cgctgtcgtt gctttcgccg cctccgtcgc ggccctccct     960
cctgcccatg attcccagtt cgctggcaat ggtgttggca acaagggcaa cagcaacgtc    1020
aagttccctg tccccgaaaa cgtgaccgtc aagcaggcct ccgacaagtg cggtgaccag    1080
gcccagctct cttgctgcaa caaggccacg tacgccggtg acaccacaac cgttgatgag    1140
ggtcttctgt ctggtgccct cagcggcctc atcggcgccg gtctggtgc gaaggtctt      1200
ggtctcttcg atcagtgctc caagcttgat gttgctgtcc tcattggcat ccaagatctt    1260
gtcaaccaga gtgcaagca aaacattgcc tgctgccaga actcccccct cagcgcggat     1320
ggcaacctta ttggtgtcgg tctcccttgc gttgcccttg ctccatcct cggatctcat    1380
caccatcacc atcac                                                     1395
```

<210> SEQ ID NO 34
<211> LENGTH: 465
<212> TYPE: PRT
<213> ORGANISM: Artificial sequence
<220> FEATURE:
<223> OTHER INFORMATION: Fusion protein yaad, Xa, rodA, his tag

<400> SEQUENCE: 34

```
Met Ala Gln Thr Gly Thr Glu Arg Val Lys Arg Gly Met Ala Glu Met
1               5                   10                  15

Gln Lys Gly Gly Val Ile Met Asp Val Ile Asn Ala Glu Gln Ala Lys
            20                  25                  30

Ile Ala Glu Glu Ala Gly Ala Val Ala Val Met Ala Leu Glu Arg Val
        35                  40                  45

Pro Ala Asp Ile Arg Ala Ala Gly Gly Val Ala Arg Met Ala Asp Pro
    50                  55                  60
```

```
Thr Ile Val Glu Glu Val Met Asn Ala Val Ser Ile Pro Val Met Ala
 65                  70                  75                  80

Lys Ala Arg Ile Gly His Ile Val Glu Ala Arg Val Leu Glu Ala Met
                 85                  90                  95

Gly Val Asp Tyr Ile Asp Glu Ser Glu Val Leu Thr Pro Ala Asp Glu
            100                 105                 110

Glu Phe His Leu Asn Lys Asn Glu Tyr Thr Val Pro Phe Val Cys Gly
        115                 120                 125

Cys Arg Asp Leu Gly Glu Ala Thr Arg Arg Ile Ala Glu Gly Ala Ser
    130                 135                 140

Met Leu Arg Thr Lys Gly Glu Pro Gly Thr Gly Asn Ile Val Glu Ala
145                 150                 155                 160

Val Arg His Met Arg Lys Val Asn Ala Gln Val Arg Lys Val Val Ala
                165                 170                 175

Met Ser Glu Asp Glu Leu Met Thr Glu Ala Lys Asn Leu Gly Ala Pro
            180                 185                 190

Tyr Glu Leu Leu Gln Ile Lys Lys Asp Gly Lys Leu Pro Val Val
        195                 200                 205

Asn Phe Ala Ala Gly Val Ala Thr Pro Ala Asp Ala Ala Leu Met
    210                 215                 220

Met Gln Leu Gly Ala Asp Gly Val Phe Val Gly Ser Gly Ile Phe Lys
225                 230                 235                 240

Ser Asp Asn Pro Ala Lys Phe Ala Lys Ala Ile Val Glu Ala Thr Thr
                245                 250                 255

His Phe Thr Asp Tyr Lys Leu Ile Ala Glu Leu Ser Lys Glu Leu Gly
            260                 265                 270

Thr Ala Met Lys Gly Ile Glu Ile Ser Asn Leu Leu Pro Glu Gln Arg
        275                 280                 285

Met Gln Glu Arg Gly Trp Arg Ser Ile Glu Gly Arg Met Lys Phe Ser
290                 295                 300

Ile Ala Ala Ala Val Val Ala Phe Ala Ala Ser Val Ala Ala Leu Pro
305                 310                 315                 320

Pro Ala His Asp Ser Gln Phe Ala Gly Asn Gly Val Gly Asn Lys Gly
                325                 330                 335

Asn Ser Asn Val Lys Phe Pro Val Pro Glu Asn Val Thr Val Lys Gln
            340                 345                 350

Ala Ser Asp Lys Cys Gly Asp Gln Ala Gln Leu Ser Cys Cys Asn Lys
        355                 360                 365

Ala Thr Tyr Ala Gly Asp Thr Thr Thr Val Asp Glu Gly Leu Leu Ser
    370                 375                 380

Gly Ala Leu Ser Gly Leu Ile Gly Ala Gly Ser Gly Ala Glu Gly Leu
385                 390                 395                 400

Gly Leu Phe Asp Gln Cys Ser Lys Leu Asp Val Ala Val Leu Ile Gly
                405                 410                 415

Ile Gln Asp Leu Val Asn Gln Lys Cys Lys Asn Ile Ala Cys Cys
        420                 425                 430

Gln Asn Ser Pro Ser Ser Ala Asp Gly Asn Leu Ile Gly Val Gly Leu
    435                 440                 445

Pro Cys Val Ala Leu Gly Ser Ile Leu Gly Ser His His His His
    450                 455                 460

His
465
```

<210> SEQ ID NO 35
<211> LENGTH: 1407
<212> TYPE: DNA
<213> ORGANISM: Artificial sequence
<220> FEATURE:
<223> OTHER INFORMATION: Coding sequence for fusion protein yaad, Xa, BASF1, his tag

<400> SEQUENCE: 35

| | | | | |
|---|---|---|---|---|
| atggctcaaa caggtactga acgtgtaaaa cgcggaatgg cagaaatgca aaaaggcggc | 60 |
| gtcatcatgg acgtcatcaa tgcggaacaa gcgaaaatcg ctgaagaagc tggagctgtc | 120 |
| gctgtaatgg cgctagaacg tgtgccagca gatattcgcg cggctggagg agttgcccgt | 180 |
| atggctgacc ctacaatcgt ggaagaagta atgaatgcag tatctatccc ggtaatggca | 240 |
| aaagcgcgta tcggacatat tgttgaagcg cgtgtgcttg aagctatggg tgttgactat | 300 |
| attgatgaaa gtgaagttct gacgccggct gacgaagaat tcatttaaa taaaaatgaa | 360 |
| tacacagttc cttttgtctg tggctgccgt gatcttggtg aagcaacacg ccgtattgcg | 420 |
| gaaggtgctt ctatgcttcg cacaaaaggt gagcctggaa caggtaatat tgttgaggct | 480 |
| gttcgccata tgcgtaaagt taacgctcaa gtgcgcaaag tagttgcgat gagtgaggat | 540 |
| gagctaatga cagaagcgaa aaacctaggt gctccttacg agcttcttct tcaaattaaa | 600 |
| aaagacggca gcttcctgt cgttaacttt gccgctggcg cgtagcaac tccagctgat | 660 |
| gctgctctca tgatgcagct tggtgctgac ggagtatttg ttggttctgg tatttttaaa | 720 |
| tcagacaacc ctgctaaatt tgcgaaagca attgtggaag caacaactca ctttactgat | 780 |
| tacaaattaa tcgctgagtt gtcaaaagag cttggtactg caatgaaagg gattgaaatc | 840 |
| tcaaacttac ttccagaaca gcgtatgcaa gaacgcggct ggagatctat tgaaggccgc | 900 |
| atgaagttct ccgtctccgc cgccgtcctc gccttcgccg cctccgtcgc cgccctccct | 960 |
| cagcacgact ccgccgccgg caacggcaac ggcgtcggca acaagttccc tgtccctgac | 1020 |
| gacgtcaccg tcaagcaggc caccgacaag tgcggcgacc aggcccagct cctcctgctg | 1080 |
| aacaaggcca cctacgccgg cgacgtcctc accgacatcg acgagggcat cctcgccggc | 1140 |
| ctcctcaaga acctcatcgg cggcggctcc ggctccgagg gcctcggcct cttcgaccag | 1200 |
| tgcgtcaagc tcgacctcca gatctccgtc atcggcatcc tatccagga cctcctcaac | 1260 |
| caggtcaaca gcagtgcaa gcagaacatc gcctgctgcc agaactcccc ttccgacgcc | 1320 |
| accggctccc tcgtcaacct cggcctcggc aacccttgca tccctgtctc cctcctccat | 1380 |
| atgggatctc atcaccatca ccatcac | 1407 |

<210> SEQ ID NO 36
<211> LENGTH: 469
<212> TYPE: PRT
<213> ORGANISM: Artificial sequence
<220> FEATURE:
<223> OTHER INFORMATION: Fusion protein yaad, Xa, BASF1, his tag

<400> SEQUENCE: 36

Met Ala Gln Thr Gly Thr Glu Arg Val Lys Arg Gly Met Ala Glu Met
1               5                   10                  15

Gln Lys Gly Gly Val Ile Met Asp Val Ile Asn Ala Glu Gln Ala Lys
            20                  25                  30

Ile Ala Glu Glu Ala Gly Ala Val Ala Val Met Ala Leu Glu Arg Val
        35                  40                  45

Pro Ala Asp Ile Arg Ala Ala Gly Gly Val Ala Arg Met Ala Asp Pro
    50                  55                  60

```
Thr Ile Val Glu Glu Val Met Asn Ala Val Ser Ile Pro Val Met Ala
 65                  70                  75                  80

Lys Ala Arg Ile Gly His Ile Val Glu Ala Arg Val Leu Glu Ala Met
                 85                  90                  95

Gly Val Asp Tyr Ile Asp Glu Ser Glu Val Leu Thr Pro Ala Asp Glu
                100                 105                 110

Glu Phe His Leu Asn Lys Asn Glu Tyr Thr Val Pro Phe Val Cys Gly
            115                 120                 125

Cys Arg Asp Leu Gly Glu Ala Thr Arg Arg Ile Ala Glu Gly Ala Ser
        130                 135                 140

Met Leu Arg Thr Lys Gly Glu Pro Gly Thr Gly Asn Ile Val Glu Ala
145                 150                 155                 160

Val Arg His Met Arg Lys Val Asn Ala Gln Val Arg Lys Val Val Ala
                165                 170                 175

Met Ser Glu Asp Glu Leu Met Thr Glu Ala Lys Asn Leu Gly Ala Pro
            180                 185                 190

Tyr Glu Leu Leu Leu Gln Ile Lys Lys Asp Gly Lys Leu Pro Val Val
        195                 200                 205

Asn Phe Ala Ala Gly Gly Val Ala Thr Pro Ala Asp Ala Ala Leu Met
210                 215                 220

Met Gln Leu Gly Ala Asp Gly Val Phe Val Gly Ser Gly Ile Phe Lys
225                 230                 235                 240

Ser Asp Asn Pro Ala Lys Phe Ala Lys Ala Ile Val Glu Ala Thr Thr
                245                 250                 255

His Phe Thr Asp Tyr Lys Leu Ile Ala Glu Leu Ser Lys Glu Leu Gly
            260                 265                 270

Thr Ala Met Lys Gly Ile Glu Ile Ser Asn Leu Leu Pro Glu Gln Arg
        275                 280                 285

Met Gln Glu Arg Gly Trp Arg Ser Ile Glu Gly Arg Met Lys Phe Ser
290                 295                 300

Val Ser Ala Ala Val Leu Ala Phe Ala Ala Ser Val Ala Ala Leu Pro
305                 310                 315                 320

Gln His Asp Ser Ala Ala Gly Asn Gly Asn Gly Val Gly Asn Lys Phe
                325                 330                 335

Pro Val Pro Asp Asp Val Thr Val Lys Gln Ala Thr Asp Lys Cys Gly
            340                 345                 350

Asp Gln Ala Gln Leu Ser Cys Cys Asn Lys Ala Thr Tyr Ala Gly Asp
        355                 360                 365

Val Leu Thr Asp Ile Asp Glu Gly Ile Leu Ala Gly Leu Leu Lys Asn
        370                 375                 380

Leu Ile Gly Gly Gly Ser Gly Ser Glu Gly Leu Gly Leu Phe Asp Gln
385                 390                 395                 400

Cys Val Lys Leu Asp Leu Gln Ile Ser Val Ile Gly Ile Pro Ile Gln
                405                 410                 415

Asp Leu Leu Asn Gln Val Asn Lys Gln Cys Lys Gln Asn Ile Ala Cys
            420                 425                 430

Cys Gln Asn Ser Pro Ser Asp Ala Thr Gly Ser Leu Val Asn Leu Gly
        435                 440                 445

Leu Gly Asn Pro Cys Ile Pro Val Ser Leu Leu His Met Gly Ser His
        450                 455                 460

His His His His
465
```

<210> SEQ ID NO 37
<211> LENGTH: 1753
<212> TYPE: DNA
<213> ORGANISM: Glycine max

<400> SEQUENCE: 37

```
cctctcaatc aaggccttta tttgttctgc acaatttaaa ataaaataac aagaattttg      60
ttgctctaaa atctcattgc tccctatctt ggaacattgc gagtgcgaca acaaggcaac     120
cctaaagatg ataatgtgca cctcacttgt ggcgtcgaca actgtatggt gcgacgatag     180
agcggatgat gaagcagaag atggtgccaa ttaacatcaa cttcgatagg cacggaggac     240
accagcgggg tcgagctagg tagcgggtgg tggtaggaga aagggtcggt gagttgggct     300
tggaagggaa gggataggaa cgagtgaaca atgttttta ttttcttata aaaatatatt      360
ctagtgcatt aattacaaga tattcatatc taacgtatca tatgtttctc acggtgggaa     420
atttgatgag ctttcccatc ctagaatcaa tcatcttttt atatgtagtt tgtgggatta     480
tggatgtagc tgtcttggaa aaacattaaa ctttaaacac accacgagaa actcgtaaga     540
cattcgttgg ggattacttg tgataacatg atccagaaac agaacaagag tttcaatgaa     600
tctaaatatt tcgaattgaa gcatttgact gttaaacatg tcattttagg ttgctatagt     660
tgtgggagat ataaggttaa tctaatggtt ggggaagaga gggggagggg gagacaaact     720
aatgaggcat atagcaacgc gcgccgggag gagtatgcca gaatcaacaa tgaaacgaca     780
tataatgact taataatcag attcaaacca tttttttta taaaattttt gctaaaggct      840
actccaatag ttacagtacg cataggacga atggtatttg cgagcatatt atttgaaagt     900
atcatgaaaa atgtggtgtt gttgaaaggt ctacggtgca ttccattgac aaagtcaatt     960
actcgttcgt ggttaatttt gctgaaaaga taagctctat ggataaactc aactgagttg    1020
cttgtttatt tttacgtctt gcaaaacaaa agtattaaaa cgacatgata aactcacaag    1080
actacaatgt tgctctataa gaagaagaat ttcaatagaa acgtttcaga ttaaagcatt    1140
tgactagtag acatgtcgtc atcaaggtgt tgaatacatt gatgcaattt tcatgttaat    1200
tgaaggaaaa taataatgta actaaaccag ttttagaata attgaaagaa tcgctgaaga    1260
ttacaccagt agttagttgt tgagttattg tacactttgc atggggcgaa tggtatttat    1320
ttgcatgggg ttgttgaaga caacaatatt ggttggtggt tgagcactca gcacgggctt    1380
tgcctgaaac tttaatgttt ccccattctt cccgtgaacg ttcagaatcc agatccattg    1440
attctcatta cattacgatt tcgcgtcaaa agtagaaact aaaaacaaaa atagagaaaa    1500
ggagaacact tgccacctca tccaacagct gcttatttaa tctctacact tgctcgtagg    1560
gtctcaattc gaggtcgcag attagattcc caattctccg ttcgccatct gttaaggtaa    1620
gcttttcttc ttaaactatt gtactttcca gttcatgcat aatagtatca ggaaacaaaa    1680
aaaaaaagta taagataaga tcattgatgt gatgtgttgt gtagcgtagg agatagagag    1740
ggagagattg aaa                                                      1753
```

<210> SEQ ID NO 38
<211> LENGTH: 235
<212> TYPE: DNA
<213> ORGANISM: Solanum tuberosum

<400> SEQUENCE: 38

```
cctgcagata gactatacta tgttttagcc tgcctgctgg ctagctacta tgttatgtta      60
tgttgtaaaa taaacaccctg ctaaggtata tctatctata ttttagcatg gctttctcaa    120
```

-continued

```
taaattgtct ttccttatcg tttactatct tatacctaat aatgaaataa taatatcaca    180
tatgaggaac gggcaggtt taggcatata tatacgagtg tagggcggag tgggg          235
```

<210> SEQ ID NO 39
<211> LENGTH: 621
<212> TYPE: DNA
<213> ORGANISM: Artificial sequence
<220> FEATURE:
<223> OTHER INFORMATION: Hydrophobin_Gm-His

<400> SEQUENCE: 39

```
atgaagacta acctgttcct cttcctgatc ttctcacttt tgcttagcct tagctcagct    60
gctcaaactg gaactgaaag ggttaagagg ggtatggctg aaatgcaaaa gggtggtgtg   120
attatggacg tgatcaacgc tgagcaggct aagattgcta agaggctgg tgctgttatt    180 gagggtagaa tgcgttttat cgttagcctt cttgctttca ctgctgctgc tactgctaca   240
gctttgccag ctagtgctgc taagaacgct aagcttgcta ctagtgctgc tttcgctaag   300
caagctgagg gaactacttg taacgtggga tctattgcct gctgtaactc accagctgag   360
actaacaacg atagccttct tagtggactt cttggagctg gacttcttaa cggacttagt   420
ggtaacactg gatcagcttg cgctaaggct agccttattg atcaacttgg acttcttgct   480
ctcgttgatc acactgaaga gggaccagtg tgtaagaata ttgtggcttg ctgcccagag   540
ggtactacta actgtgttgc tgttgataac gctggtgctg aactaaggc tgaaggtagt    600 catcatcatc accatcacta a                                             621
```

<210> SEQ ID NO 40
<211> LENGTH: 206
<212> TYPE: PRT
<213> ORGANISM: Artificial sequence
<220> FEATURE:
<223> OTHER INFORMATION: Hydrophobin_Gm-His-protein

<400> SEQUENCE: 40

```
Met Lys Thr Asn Leu Phe Leu Phe Leu Ile Phe Ser Leu Leu Leu Ser
1               5                   10                  15

Leu Ser Ser Ala Ala Gln Thr Gly Thr Glu Arg Val Lys Arg Gly Met
                20                  25                  30

Ala Glu Met Gln Lys Gly Gly Val Ile Met Asp Val Ile Asn Ala Glu
            35                  40                  45

Gln Ala Lys Ile Ala Glu Glu Ala Gly Ala Val Ile Glu Gly Arg Met
        50                  55                  60

Arg Phe Ile Val Ser Leu Leu Ala Phe Thr Ala Ala Ala Thr Ala Thr
65                  70                  75                  80

Ala Leu Pro Ala Ser Ala Ala Lys Asn Ala Lys Leu Ala Thr Ser Ala
                85                  90                  95

Ala Phe Ala Lys Gln Ala Glu Gly Thr Thr Cys Asn Val Gly Ser Ile
            100                 105                 110

Ala Cys Cys Asn Ser Pro Ala Glu Thr Asn Asn Asp Ser Leu Leu Ser
        115                 120                 125

Gly Leu Leu Gly Ala Gly Leu Leu Asn Gly Leu Ser Gly Asn Thr Gly
    130                 135                 140

Ser Ala Cys Ala Lys Ala Ser Leu Ile Asp Gln Leu Gly Leu Leu Ala
145                 150                 155                 160

Leu Val Asp His Thr Glu Glu Gly Pro Val Cys Lys Asn Ile Val Ala
                165                 170                 175
```

```
Cys Cys Pro Glu Gly Thr Thr Asn Cys Val Ala Val Asp Asn Ala Gly
            180                 185                 190

Ala Gly Thr Lys Ala Glu Gly Ser His His His His His
        195                 200                 205

<210> SEQ ID NO 41
<211> LENGTH: 597
<212> TYPE: DNA
<213> ORGANISM: Artificial sequence
<220> FEATURE:
<223> OTHER INFORMATION: Hydrophobin_Gm

<400> SEQUENCE: 41
atgaagacta acctgttcct cttcctgatc ttctcacttt tgcttagcct tagctcagct    60
gctcaaactg gaactgaaag ggttaagagg ggtatggctg aaatgcaaaa gggtggtgtg   120
attatggacg tgatcaacgc tgagcaggct aagattgctg aagaggctgg tgctgttatt   180
gagggtagaa tgcgttttat cgttagcctt cttgctttca ctgctgctgc tactgctaca   240
gctttgccag ctagtgctgc taagaacgct aagcttgcta ctagtgctgc tttcgctaag   300
caagctgagg gaactacttg taacgtggga tctattgcct gctgtaactc accagctgag   360
actaacaacg atagccttct tagtggactt cttggagctg gacttcttaa cggacttagt   420
ggtaacactg gatcagcttg cgctaaggct agccttattg atcaacttgg acttcttgct   480
ctcgttgatc acactgaaga gggaccagtg tgtaagaata ttgtggcttg ctgcccagag   540
ggtactacta ctgtgttgc tgttgataac gctggtgctg aactaaggc tgaataa       597

<210> SEQ ID NO 42
<211> LENGTH: 198
<212> TYPE: PRT
<213> ORGANISM: Artificial sequence
<220> FEATURE:
<223> OTHER INFORMATION: Hydrophobin_Gm protein

<400> SEQUENCE: 42

Met Lys Thr Asn Leu Phe Leu Phe Leu Ile Phe Ser Leu Leu Leu Ser
1               5                   10                  15

Leu Ser Ser Ala Ala Gln Thr Gly Thr Glu Arg Val Lys Arg Gly Met
            20                  25                  30

Ala Glu Met Gln Lys Gly Gly Val Ile Met Asp Val Ile Asn Ala Glu
        35                  40                  45

Gln Ala Lys Ile Ala Glu Glu Ala Gly Ala Val Ile Glu Gly Arg Met
    50                  55                  60

Arg Phe Ile Val Ser Leu Leu Ala Phe Thr Ala Ala Ala Thr Ala Thr
65                  70                  75                  80

Ala Leu Pro Ala Ser Ala Ala Lys Asn Ala Lys Leu Ala Thr Ser Ala
                85                  90                  95

Ala Phe Ala Lys Gln Ala Glu Gly Thr Thr Cys Asn Val Gly Ser Ile
            100                 105                 110

Ala Cys Cys Asn Ser Pro Ala Glu Thr Asn Asn Asp Ser Leu Leu Ser
        115                 120                 125

Gly Leu Leu Gly Ala Gly Leu Leu Asn Gly Leu Ser Gly Asn Thr Gly
    130                 135                 140

Ser Ala Cys Ala Lys Ala Ser Leu Ile Asp Gln Leu Gly Leu Leu Ala
145                 150                 155                 160

Leu Val Asp His Thr Glu Glu Gly Pro Val Cys Lys Asn Ile Val Ala
                165                 170                 175
```

```
Cys Cys Pro Glu Gly Thr Thr Asn Cys Val Ala Val Asp Asn Ala Gly
            180                 185                 190

Ala Gly Thr Lys Ala Glu
        195
```

<210> SEQ ID NO 43
<211> LENGTH: 112
<212> TYPE: PRT
<213> ORGANISM: Artificial sequence
<220> FEATURE:
<223> OTHER INFORMATION: Hydrophbin_SC3, version 1

<400> SEQUENCE: 43

```
Gly Gly His Pro Gly Thr Thr Pro Pro Val Thr Thr Val Thr
1               5                   10                  15

Val Thr Thr Pro Pro Ser Thr Thr Ile Ala Ala Gly Gly Thr Cys
            20                  25                  30

Thr Thr Gly Ser Leu Ser Cys Cys Asn Gln Val Gln Ser Ala Ser Ser
        35                  40                  45

Ser Pro Val Thr Ala Leu Leu Gly Leu Leu Gly Ile Val Leu Ser Asp
    50                  55                  60

Leu Asn Val Leu Val Gly Ile Ser Cys Ser Pro Leu Thr Val Ile Gly
65                  70                  75                  80

Val Gly Gly Ser Gly Cys Ser Ala Gln Thr Val Cys Cys Glu Asn Thr
                85                  90                  95

Gln Phe Asn Gly Leu Ile Asn Ile Gly Cys Thr Pro Ile Asn Ile Leu
            100                 105                 110
```

<210> SEQ ID NO 44
<211> LENGTH: 136
<212> TYPE: PRT
<213> ORGANISM: Artificial sequence
<220> FEATURE:
<223> OTHER INFORMATION: Hydrophobin Sc3, version 2

<400> SEQUENCE: 44

```
Met Phe Ala Arg Leu Pro Val Val Phe Leu Tyr Ala Phe Val Ala Phe
1               5                   10                  15

Gly Ala Leu Val Ala Ala Leu Pro Gly Gly His Pro Gly Thr Thr Thr
            20                  25                  30

Pro Pro Val Thr Thr Val Thr Val Thr Thr Pro Pro Ser Thr Thr
            35                  40                  45

Thr Ile Ala Ala Gly Gly Thr Cys Thr Thr Gly Ser Leu Ser Cys Cys
    50                  55                  60

Asn Gln Val Gln Ser Ala Ser Ser Ser Pro Val Thr Ala Leu Leu Gly
65                  70                  75                  80

Leu Leu Gly Ile Val Leu Ser Asp Leu Asn Val Leu Val Gly Ile Ser
                85                  90                  95

Cys Ser Pro Leu Thr Val Ile Gly Val Gly Gly Ser Gly Cys Ser Ala
            100                 105                 110

Gln Thr Val Cys Cys Glu Asn Thr Gln Phe Asn Gly Leu Ile Asn Ile
        115                 120                 125

Gly Cys Thr Pro Ile Asn Ile Leu
    130                 135
```

<210> SEQ ID NO 45
<211> LENGTH: 71
<212> TYPE: PRT

<213> ORGANISM: Artificial sequence
<220> FEATURE:
<223> OTHER INFORMATION: Hydrophobin HFBII, version 1

<400> SEQUENCE: 45

```
Ala Val Cys Pro Thr Gly Leu Phe Ser Asn Pro Leu Cys Cys Ala Thr
1               5                   10                  15

Asn Val Leu Asp Leu Ile Gly Val Asp Cys Lys Thr Pro Thr Ile Ala
                20                  25                  30

Val Asp Thr Gly Ala Ile Phe Gln Ala His Cys Ala Ser Lys Gly Ser
            35                  40                  45

Lys Pro Leu Cys Cys Val Ala Pro Val Ala Asp Gln Ala Leu Leu Cys
50                  55                  60

Gln Lys Ala Ile Gly Thr Phe
65                  70
```

<210> SEQ ID NO 46
<211> LENGTH: 86
<212> TYPE: PRT
<213> ORGANISM: Artificial sequence
<220> FEATURE:
<223> OTHER INFORMATION: Hydrophobin HFBII; version 2

<400> SEQUENCE: 46

```
Met Gln Phe Phe Ala Val Ala Leu Phe Ala Thr Ser Ala Leu Ala Ala
1               5                   10                  15

Val Cys Pro Thr Gly Leu Phe Ser Asn Pro Leu Cys Cys Ala Thr Asn
                20                  25                  30

Val Leu Asp Leu Ile Gly Val Asp Cys Lys Thr Pro Thr Ile Ala Val
            35                  40                  45

Asp Thr Gly Ala Ile Phe Gln Ala His Cys Ala Ser Lys Gly Ser Lys
        50                  55                  60

Pro Leu Cys Cys Val Ala Pro Val Ala Asp Gln Ala Leu Leu Cys Gln
65                  70                  75                  80

Lys Ala Ile Gly Thr Phe
                85
```

<210> SEQ ID NO 47
<211> LENGTH: 1146
<212> TYPE: DNA
<213> ORGANISM: Artificial sequence
<220> FEATURE:
<223> OTHER INFORMATION: Coding sequence for fusion protein yaaD_HFBII

<400> SEQUENCE: 47

```
atggctcaaa caggtactga acgtgtaaaa cgcggaatgg cagaaatgca aaaaggcggc      60
gtcatcatgg acgtcatcaa tgcggaacaa gcgaaaatcg ctgaagaagc tggagctgtc     120
gctgtaatgg cgctagaacg tgtgccagca gatattcgcg cggctggagg agttgcccgt     180
atggctgacc ctacaatcgt ggaagaagta atgaatgcag tatctatccc ggtaatggca     240
aaagcgcgta tcggacatat tgttgaagcg cgtgtgcttg aagctatggg tgttgactat     300
attgatgaaa gtgaagttct gacgccggct gacgaagaat tcattaaa taaaaatgaa      360 tacacagttc cttttgtctg tggctgccgt gatcttggtg aagcaacacg ccgtattgcg     420
gaaggtgctt ctatgcttcg cacaaaaggt gagcctggaa caggtaatat tgttgaggct     480
gttcgccata tgcgtaaagt taacgctcaa gtgcgcaaag tagttgcgat gagtgaggat     540
gagctaatga cagaagcgaa aaacctaggt gctccttacg agcttcttct tcaaattaaa     600
```

-continued

```
aaagacggca agcttcctgt cgttaacttt gccgctggcg gcgtagcaac tccagctgat    660
gctgctctca tgatgcagct tggtgctgac ggagtatttg ttggttctgg tatttttaaa    720
tcagacaacc ctgctaaatt tgcgaaagca attgtggaag caacaactca ctttactgat    780
tacaaattaa tcgctgagtt gtcaaaagag cttggtactg caatgaaagg gattgaaatc    840
tcaaacttac ttccagaaca gcgtatgcaa gaacgcggct ggagatctat gcagttcttc    900
gccgtcgccc tcttcgccac cagcgccctg gctgctgtct gccctaccgg cctcttctcc    960
aaccctctgt gctgtgccac caacgtcctc gacctcattg gcgttgactg caagacccct   1020
accatcgccg tcgacactgg cgccatcttc caggctcact gtgccagcaa gggctccaag   1080
cctctttgct gcgttgctcc cgtggccgac caggctctcc tgtgccagaa ggccatcggc   1140
accttc                                                              1146
```

<210> SEQ ID NO 48
<211> LENGTH: 382
<212> TYPE: PRT
<213> ORGANISM: Artificial sequence
<220> FEATURE:
<223> OTHER INFORMATION: Fusion protein yaaD_HFBII

<400> SEQUENCE: 48

```
Met Ala Gln Thr Gly Thr Glu Arg Val Lys Arg Gly Met Ala Glu Met
1               5                   10                  15

Gln Lys Gly Gly Val Ile Met Asp Val Ile Asn Ala Glu Gln Ala Lys
            20                  25                  30

Ile Ala Glu Glu Ala Gly Ala Val Ala Val Met Ala Leu Glu Arg Val
        35                  40                  45

Pro Ala Asp Ile Arg Ala Ala Gly Gly Val Ala Arg Met Ala Asp Pro
    50                  55                  60

Thr Ile Val Glu Glu Val Met Asn Ala Val Ser Ile Pro Val Met Ala
65                  70                  75                  80

Lys Ala Arg Ile Gly His Ile Val Glu Ala Arg Val Leu Glu Ala Met
                85                  90                  95

Gly Val Asp Tyr Ile Asp Glu Ser Glu Val Leu Thr Pro Ala Asp Glu
            100                 105                 110

Glu Phe His Leu Asn Lys Asn Glu Tyr Thr Val Pro Phe Val Cys Gly
        115                 120                 125

Cys Arg Asp Leu Gly Glu Ala Thr Arg Arg Ile Ala Glu Gly Ala Ser
    130                 135                 140

Met Leu Arg Thr Lys Gly Glu Pro Gly Thr Gly Asn Ile Val Glu Ala
145                 150                 155                 160

Val Arg His Met Arg Lys Val Asn Ala Gln Val Arg Lys Val Val Ala
                165                 170                 175

Met Ser Glu Asp Glu Leu Met Thr Glu Ala Lys Asn Leu Gly Ala Pro
            180                 185                 190

Tyr Glu Leu Leu Leu Gln Ile Lys Lys Asp Gly Lys Leu Pro Val Val
        195                 200                 205

Asn Phe Ala Ala Gly Gly Val Ala Thr Pro Ala Asp Ala Ala Leu Met
    210                 215                 220

Met Gln Leu Gly Ala Asp Gly Val Phe Val Gly Ser Gly Ile Phe Lys
225                 230                 235                 240

Ser Asp Asn Pro Ala Lys Phe Ala Lys Ala Ile Val Glu Ala Thr Thr
                245                 250                 255

His Phe Thr Asp Tyr Lys Leu Ile Ala Glu Leu Ser Lys Glu Leu Gly
```

```
                260              265             270
Thr Ala Met Lys Gly Ile Glu Ile Ser Asn Leu Leu Pro Glu Gln Arg
            275                 280             285

Met Gln Glu Arg Gly Trp Arg Ser Met Gln Phe Phe Ala Val Ala Leu
        290                 295             300

Phe Ala Thr Ser Ala Leu Ala Ala Val Cys Pro Thr Gly Leu Phe Ser
305                 310             315                     320

Asn Pro Leu Cys Cys Ala Thr Asn Val Leu Asp Leu Ile Gly Val Asp
                325             330              335

Cys Lys Thr Pro Thr Ile Ala Val Asp Thr Gly Ala Ile Phe Gln Ala
            340             345             350

His Cys Ala Ser Lys Gly Ser Lys Pro Leu Cys Cys Val Ala Pro Val
            355             360             365

Ala Asp Gln Ala Leu Leu Cys Gln Lys Ala Ile Gly Thr Phe
            370             375             380

<210> SEQ ID NO 49
<211> LENGTH: 1179
<212> TYPE: DNA
<213> ORGANISM: Artificial sequence
<220> FEATURE:
<223> OTHER INFORMATION: Coding sequence of fusion protein yaad-HFPI

<400> SEQUENCE: 49
atggctcaaa caggtactga acgtgtaaaa cgcggaatgg cagaaatgca aaaggcggc       60 gtcatcatgg acgtcatcaa tgcggaacaa gcgaaaatcg ctgaagaagc tggagctgtc     120
gctgtaatgg cgctagaacg tgtgccagca gatattcgcg cggctggagg agttgcccgt     180
atggctgacc ctacaatcgt ggaagaagta atgaatgcag tatctatccc ggtaatggca     240
aaagcgcgta tcggacatat tgttgaagcg cgtgtgcttg aagctatggg tgttgactat     300
attgatgaaa gtgaagttct gacgccggct gacgaagaat tcatttaaa taaaaatgaa      360 tacacagttc cttttgtctg tggctgccgt gatcttggtg aagcaacacg ccgtattgcg     420
gaaggtgctt ctatgcttcg cacaaaaggt gagcctggaa caggtaatat tgttgaggct     480
gttcgccata tgcgtaaagt aacgctcaa gtgcgcaaag tagttgcgat gagtgaggat     540
gagctaatga cagaagcgaa aaacctaggt gctccttacg agcttcttct tcaaattaaa     600
aaagacggca gcttcctgt cgttaacttt gccgctggcg gctagcaac tccagctgat      660 gctgctctca tgatgcagct tggtgctgac ggagtatttg ttggttctgg tattttaa     720 tcagacaacc ctgctaaatt tgcgaaagca attgtggaag caacaactca ctttactgat    780
tacaaattaa tcgctgagtt gtcaaaagag cttggtactg caatgaaagg gattgaaatc    840
tcaaacttac ttccagaaca gcgtatgcaa gaacgcggct ggagatctat gaagttcttc    900
gccatcgccg ctctctttgc cgccgctgcc gttgcccagc ctctcgagga ccgcagcaac    960
ggcaacggca atgtttgccc tcccggcctc ttcagcaacc cccagtgctg tgccacccaa   1020
gtccttggcc tcatcggcct tgactgcaaa gtcccctccc agaacgttta cgacggcacc   1080
gacttccgca acgtctgcgc caaaaccggc gcccagcctc tctgctgcgt ggcccccgtt   1140
gccggccagg ctcttctgtg ccagaccgcc gtcggtgct                           1179

<210> SEQ ID NO 50
<211> LENGTH: 393
<212> TYPE: PRT
<213> ORGANISM: Artificial sequence
<220> FEATURE:
```

<223> OTHER INFORMATION: fusion protein yaad-HFPI

<400> SEQUENCE: 50

Met Ala Gln Thr Gly Thr Glu Arg Val Lys Arg Gly Met Ala Glu Met
1               5                   10                  15

Gln Lys Gly Gly Val Ile Met Asp Val Ile Asn Ala Glu Gln Ala Lys
            20                  25                  30

Ile Ala Glu Glu Ala Gly Ala Val Ala Val Met Ala Leu Glu Arg Val
        35                  40                  45

Pro Ala Asp Ile Arg Ala Ala Gly Gly Val Ala Arg Met Ala Asp Pro
    50                  55                  60

Thr Ile Val Glu Glu Val Met Asn Ala Val Ser Ile Pro Val Met Ala
65                  70                  75                  80

Lys Ala Arg Ile Gly His Ile Val Glu Ala Arg Val Leu Glu Ala Met
                85                  90                  95

Gly Val Asp Tyr Ile Asp Glu Ser Glu Val Leu Thr Pro Ala Asp Glu
            100                 105                 110

Glu Phe His Leu Asn Lys Asn Glu Tyr Thr Val Pro Phe Val Cys Gly
        115                 120                 125

Cys Arg Asp Leu Gly Glu Ala Thr Arg Arg Ile Ala Glu Gly Ala Ser
    130                 135                 140

Met Leu Arg Thr Lys Gly Glu Pro Gly Thr Gly Asn Ile Val Glu Ala
145                 150                 155                 160

Val Arg His Met Arg Lys Val Asn Ala Gln Val Arg Lys Val Val Ala
                165                 170                 175

Met Ser Glu Asp Glu Leu Met Thr Glu Ala Lys Asn Leu Gly Ala Pro
            180                 185                 190

Tyr Glu Leu Leu Leu Gln Ile Lys Lys Asp Gly Lys Leu Pro Val Val
        195                 200                 205

Asn Phe Ala Ala Gly Gly Val Ala Thr Pro Ala Asp Ala Ala Leu Met
    210                 215                 220

Met Gln Leu Gly Ala Asp Gly Val Phe Val Gly Ser Gly Ile Phe Lys
225                 230                 235                 240

Ser Asp Asn Pro Ala Lys Phe Ala Lys Ala Ile Val Glu Ala Thr Thr
                245                 250                 255

His Phe Thr Asp Tyr Lys Leu Ile Ala Glu Leu Ser Lys Glu Leu Gly
            260                 265                 270

Thr Ala Met Lys Gly Ile Glu Ile Ser Asn Leu Leu Pro Glu Gln Arg
        275                 280                 285

Met Gln Glu Arg Gly Trp Arg Ser Met Lys Phe Phe Ala Ile Ala Ala
    290                 295                 300

Leu Phe Ala Ala Ala Val Ala Gln Pro Leu Glu Asp Arg Ser Asn
305                 310                 315                 320

Gly Asn Gly Asn Val Cys Pro Pro Gly Leu Phe Ser Asn Pro Gln Cys
                325                 330                 335

Cys Ala Thr Gln Val Leu Gly Leu Ile Gly Leu Asp Cys Lys Val Pro
            340                 345                 350

Ser Gln Asn Val Tyr Asp Gly Thr Asp Phe Arg Asn Val Cys Ala Lys
        355                 360                 365

Thr Gly Ala Gln Pro Leu Cys Cys Val Ala Pro Val Ala Gly Gln Ala
    370                 375                 380

Leu Leu Cys Gln Thr Ala Val Gly Ala
385                 390

<210> SEQ ID NO 51
<211> LENGTH: 1299
<212> TYPE: DNA
<213> ORGANISM: Artificial sequence
<220> FEATURE:
<223> OTHER INFORMATION: Coding sequence fusion protein yaaD_TT1

<400> SEQUENCE: 51

```
atggctcaaa caggtactga acgtgtaaaa cgcggaatgg cagaaatgca aaaaggcggc        60
gtcatcatgg acgtcatcaa tgcggaacaa gcgaaaatcg ctgaagaagc tggagctgtc       120
gctgtaatgg cgctagaacg tgtgccagca gatattcgcg cggctggagg agttgcccgt       180
atggctgacc ctacaatcgt ggaagaagta atgaatgcag tatctatccc ggtaatggca       240
aaagcgcgta tcggacatat tgttgaagcg cgtgtgcttg aagctatggg tgttgactat       300
attgatgaaa gtgaagttct gacgccggct gacgaagaat tcatttaaa taaaaatgaa       360
tacacagttc cttttgtctg tggctgccgt gatcttggtg aagcaacacg ccgtattgcg       420
gaaggtgctt ctatgcttcg cacaaaaggt gagcctggaa caggtaatat tgttgaggct       480
gttcgccata tgcgtaaagt taacgctcaa gtgcgcaaag tagttgcgat gagtgaggat       540
gagctaatga cagaagcgaa aaacctaggt gctccttacg agcttcttct tcaaattaaa       600
aaagacggca agcttcctgt cgttaacttt gccgctggcg gcgtagcaac tccagctgat       660
gctgctctca tgatgcagct tggtgctgac ggagtatttg ttggttctgg tatttttaaa       720
tcagacaacc ctgctaaatt tgcgaaagca attgtggaag caacaactca cttactgat        780
tacaaattaa tcgctgagtt gtcaaaagag cttggtactg caatgaaagg gattgaaatc       840
tcaaacttac ttccagaaca gcgtatgcaa gaacgcggct ggagatctat ggccctgcca       900
aacgtcggtc ccagtgggaa gacggctcac aagccgcacc aggagccttt ctggcctgtg       960
cagcaggacg tgaccgtgga acaggccaag gctatctgtg gtgaaggcaa ccaggtcgct      1020
tgctgcaacg aggtcagcta cgcgggcgac accaccgaaa tcgcgaccgg cccctggct       1080
ggcaccctca aggacctgct cggcggcaag aacggcgcca agggcctggg tctcttcgac      1140
aagtgctcgc gtctcaatgt cgatctcctg cttggcctgt cgagcctcat caaccaagaa      1200
tgcaagcagc acattgcctg ctgccagggc aacgaggccg attcctccaa cgacctcatc      1260
ggtctcaaca ttccttgcat tgcccttggc tcgctgctg                             1299
```

<210> SEQ ID NO 52
<211> LENGTH: 433
<212> TYPE: PRT
<213> ORGANISM: Artificial sequence
<220> FEATURE:
<223> OTHER INFORMATION: Fusion protein yaaD_TT1

<400> SEQUENCE: 52

```
Met Ala Gln Thr Gly Thr Glu Arg Val Lys Arg Gly Met Ala Glu Met
1               5                  10                  15

Gln Lys Gly Gly Val Ile Met Asp Val Ile Asn Ala Glu Gln Ala Lys
            20                  25                  30

Ile Ala Glu Glu Ala Gly Ala Val Ala Val Met Ala Leu Glu Arg Val
        35                  40                  45

Pro Ala Asp Ile Arg Ala Ala Gly Gly Val Ala Arg Met Ala Asp Pro
    50                  55                  60

Thr Ile Val Glu Glu Val Met Asn Ala Val Ser Ile Pro Val Met Ala
65                  70                  75                  80
```

```
Lys Ala Arg Ile Gly His Ile Val Glu Ala Arg Val Leu Glu Ala Met
                85                  90                  95
Gly Val Asp Tyr Ile Asp Glu Ser Glu Val Leu Thr Pro Ala Asp Glu
                100                 105                 110
Glu Phe His Leu Asn Lys Asn Glu Tyr Thr Val Pro Phe Val Cys Gly
                115                 120                 125
Cys Arg Asp Leu Gly Glu Ala Thr Arg Arg Ile Ala Glu Gly Ala Ser
                130                 135                 140
Met Leu Arg Thr Lys Gly Glu Pro Gly Thr Gly Asn Ile Val Glu Ala
145                 150                 155                 160
Val Arg His Met Arg Lys Val Asn Ala Gln Val Arg Lys Val Val Ala
                165                 170                 175
Met Ser Glu Asp Glu Leu Met Thr Glu Ala Lys Asn Leu Gly Ala Pro
                180                 185                 190
Tyr Glu Leu Leu Leu Gln Ile Lys Lys Asp Gly Lys Leu Pro Val Val
                195                 200                 205
Asn Phe Ala Ala Gly Gly Val Ala Thr Pro Ala Asp Ala Ala Leu Met
                210                 215                 220
Met Gln Leu Gly Ala Asp Gly Val Phe Val Gly Ser Gly Ile Phe Lys
225                 230                 235                 240
Ser Asp Asn Pro Ala Lys Phe Ala Lys Ala Ile Val Glu Ala Thr Thr
                245                 250                 255
His Phe Thr Asp Tyr Lys Leu Ile Ala Glu Leu Ser Lys Glu Leu Gly
                260                 265                 270
Thr Ala Met Lys Gly Ile Glu Ile Ser Asn Leu Leu Pro Glu Gln Arg
                275                 280                 285
Met Gln Glu Arg Gly Trp Arg Ser Met Ala Leu Pro Asn Val Gly Pro
                290                 295                 300
Ser Gly Lys Thr Ala His Lys Pro His Gln Glu Pro Phe Trp Pro Val
305                 310                 315                 320
Gln Gln Asp Val Thr Val Glu Gln Ala Lys Ala Ile Cys Gly Glu Gly
                325                 330                 335
Asn Gln Val Ala Cys Asn Glu Val Ser Tyr Ala Gly Asp Thr Thr
                340                 345                 350
Glu Ile Ala Thr Gly Pro Leu Ala Gly Thr Leu Lys Asp Leu Leu Gly
                355                 360                 365
Gly Lys Asn Gly Ala Lys Gly Leu Gly Leu Phe Asp Lys Cys Ser Arg
                370                 375                 380
Leu Asn Val Asp Leu Leu Leu Gly Leu Ser Ser Leu Ile Asn Gln Glu
385                 390                 395                 400
Cys Lys Gln His Ile Ala Cys Cys Gln Gly Asn Glu Ala Asp Ser Ser
                405                 410                 415
Asn Asp Leu Ile Gly Leu Asn Ile Pro Cys Ile Ala Leu Gly Ser Leu
                420                 425                 430
Leu

<210> SEQ ID NO 53
<211> LENGTH: 156
<212> TYPE: PRT
<213> ORGANISM: Homo sapiens

<400> SEQUENCE: 53

Met Gln Ile Phe Val Lys Thr Leu Thr Gly Lys Thr Ile Thr Leu Glu
1               5                   10                  15
```

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
                35                  40                  45

Gln Leu Glu Asp Gly Arg Thr Leu Ser Asp Tyr Asn Ile Gln Lys Glu
 50                  55                  60

Ser Thr Leu His Leu Val Leu Arg Leu Arg Gly Gly Ala Lys Lys Arg
65                  70                  75                  80

Lys Lys Lys Ser Tyr Thr Thr Pro Lys Lys Asn Lys His Lys Arg Lys
                85                  90                  95

Lys Val Lys Leu Ala Val Leu Lys Tyr Tyr Lys Val Asp Glu Asn Gly
            100                 105                 110

Lys Ile Ser Arg Leu Arg Arg Glu Cys Pro Ser Asp Glu Cys Gly Ala
            115                 120                 125

Gly Val Phe Met Ala Ser His Phe Asp Arg His Tyr Cys Gly Lys Cys
        130                 135                 140

Cys Leu Thr Tyr Cys Phe Asn Lys Pro Glu Asp Lys
145                 150                 155

<210> SEQ ID NO 54
<211> LENGTH: 105
<212> TYPE: PRT
<213> ORGANISM: Homo sapiens

<400> SEQUENCE: 54

Met Val Lys Gln Ile Glu Ser Lys Thr Ala Phe Gln Glu Ala Leu Asp
1               5                   10                  15

Ala Ala Gly Asp Lys Leu Val Val Val Asp Phe Ser Ala Thr Trp Cys
            20                  25                  30

Gly Pro Cys Lys Met Ile Lys Pro Phe Phe His Ser Leu Ser Glu Lys
                35                  40                  45

Tyr Ser Asn Val Ile Phe Leu Glu Val Asp Val Asp Asp Cys Gln Asp
 50                  55                  60

Val Ala Ser Glu Cys Glu Val Lys Cys Met Pro Thr Phe Gln Phe Phe
65                  70                  75                  80

Lys Lys Gly Gln Lys Val Gly Glu Phe Ser Gly Ala Asn Lys Glu Lys
                85                  90                  95

Leu Glu Ala Thr Ile Asn Glu Leu Val
            100                 105

<210> SEQ ID NO 55
<211> LENGTH: 408
<212> TYPE: DNA
<213> ORGANISM: Artificial sequence
<220> FEATURE:
<223> OTHER INFORMATION: Nucleotide sequence hydrophobin variant 1

<400> SEQUENCE: 55
atgcgattca ttgttagttt actagccttt actgccgcgg ccaccgcgac tgccatgcct      60
gcttcggcag ccaaaaatgc gaaattagcg acctccgcag catttgcaaa gcaggcagaa     120
ggtaccacgt gcaatgtcgg gtcgatagcg tgttgcaatt ccccgctga aacaaataat      180 gactccctat tatctggatt gttaggcgcg gggcttttaa atgggctttc tgggaataca     240
ggtagcgcat gtgcaaaagc atcactcata gaccagttgg gactactggc gttggtggac     300
catacggagg aaggtccggt atgcaaaaat atagttgctt gttgccccga aggcaccacc     360
aattgcgtag cagtggacaa tgcaggggca ggtacgaaag cagagtag                  408

<210> SEQ ID NO 56
<211> LENGTH: 408
<212> TYPE: DNA
<213> ORGANISM: Artificial sequence
<220> FEATURE:
<223> OTHER INFORMATION: Nucleotide sequence hydrophobin variant 2

<400> SEQUENCE: 56

```
atgcggttca ttgtatcgtt gcttgccttt actgcagcag caacggcaac tgcgatgccg      60
gcgtccgcgg caaagaatgc caaactggcg acatccgctg cttttgcaaa acaagcggaa     120
gggacaacct gcaatgttgg ttctatcgca tgttgcaact caccagcaga acaaataat      180
gatagtttgc tgagtggcct cctcggtgca ggactactta acggcttaag tggaaacacc     240
ggaagtgcct gtgcaaaagc ctccttgata gaccagctag ggttgcttgc cctagtcgat     300
catacggagg agggaccggt ttgtaaaaac atcgtagcct gttgtcccga agggaccact     360
aattgcgtcg ctgttgacaa tgctggtgca ggaactaagg cggaataa                  408
```

<210> SEQ ID NO 57
<211> LENGTH: 408
<212> TYPE: DNA
<213> ORGANISM: Artificial sequence
<220> FEATURE:
<223> OTHER INFORMATION: Nucleotide sequence hydrophobin variant 3

<400> SEQUENCE: 57

```
atgcgtttca tagtttccct cttggctttt acagcagctg cgacggcaac agccttgcca      60
gctagtgctg cgaaaaacgc aaagctagct acttcagctg ctttcgctaa acaagctgaa     120
ggaaccacgt gcaacgtagg aagtatagct tgttgtaatt ccccagctga actaataac      180
gacagtctat tatccgggct tctaggcgct ggccttctca atgggctcag cggcaatacg     240
ggatcagcct gcgcaaaggc gtctctcatc gaccagcttg gactcctcgc tctcgtcgat     300
cacactgagg aaggtcctgt atgtaaaaac atcgtcgcat gctgtcccga gggtaccacc     360
aattgtgtgg ccgtagataa tgctggagct gggactaaag ctgagtaa                  408
```

<210> SEQ ID NO 58
<211> LENGTH: 408
<212> TYPE: DNA
<213> ORGANISM: Artificial sequence
<220> FEATURE:
<223> OTHER INFORMATION: Nucleotide sequence hydrophobin variant 4

<400> SEQUENCE: 58

```
atgaggttca ttgtcagcct tttagccttt actgcggccg caactgctac agcaatgcct      60
gcatcggccg caaaaaacgc taagcttgct actagtgcag ctttcgcaaa gcaagctgag     120
ggaactactt gcaacgtggg aagtattgcc tgctgcaata gtccggctga aactaacaac     180
gacagtcttt tgagtggttt gcttggagct gggttactta acggactttc cggcaacact     240
ggatcagcat gcgcaaaggc tagcctgatt gaccaactcg gacttctcgc tctagttgac     300
catactgaag agggtccagt gtgcaaaaac atagtggcgt gttgtccgga gggtaccact     360
aactgcgtcg ctgttgacaa tgctggcgct ggtactaaag ctgaataa                  408
```

<210> SEQ ID NO 59
<211> LENGTH: 408
<212> TYPE: DNA
<213> ORGANISM: Artificial sequence
<220> FEATURE:

<223> OTHER INFORMATION: Nucleotide sequence hydrophobin variant 5

<400> SEQUENCE: 59

```
atgcgtttca tcgtttcctt gcttgctttc accgctgctg ctactgccac agccatgccc    60
gctagtgctg ccaagaatgc taagcttgct acgagtgcgg ctttcgctaa gcaggctgaa   120
ggaacaactt gcaacgtagg atctattgcc tgttgtaatt cacccgctga gactaacaac   180
gacagccttc ttagtggact acttggagct ggacttctaa acggacttag tggtaacacc   240
ggatcagctt gcgcaaaggc ttctcttatt gatcaacttg acttttggc tctcgttgat    300
catactgagg agggaccagt gtgtaaaaac atcgtggctt gctgccccga gggtaccacg   360
aactgtgtgg ccgttgacaa cgctggagct ggcactaagg cggaataa               408
```

<210> SEQ ID NO 60
<211> LENGTH: 408
<212> TYPE: DNA
<213> ORGANISM: Artificial sequence
<220> FEATURE:
<223> OTHER INFORMATION: Nucleotide sequence hydrophobin variant 6

<400> SEQUENCE: 60

```
atgcgtttta tagttagcct tcttgctttc actgctgctg ctactgctac ggctatgcca    60
gcttcggctg caaagaacgc taagcttgct actagcgctg cttttgctaa gcaagctgaa   120
ggtactactt gcaacgtggg atctattgcc tgctgtaact cacccgctga aaccaataat   180
gatagccttt tatcgggact tcttggtgct ggacttctca acgggttaag tggtaacacc   240
ggaagtgctt gtgctaaggc tagccttatt gaccagcttg acttcttgc tcttgttgat    300
cacactgagg agggaccagt gtgtaagaat attgtggctt gctgccccga gggtactact   360
aactgtgttg cggttgacaa cgctggtgct ggaactaaag ctgagtaa                408
```

<210> SEQ ID NO 61
<211> LENGTH: 408
<212> TYPE: DNA
<213> ORGANISM: Artificial sequence
<220> FEATURE:
<223> OTHER INFORMATION: Nucleotide sequence hydrophobin variant 7

<400> SEQUENCE: 61

```
atgcgtttta tcgttagcct tcttgctttc actgccgctg ctactgctac agcaatgcca    60
gctagtgctg ctaagaacgc taagttagct actagtgctg ctttcgctaa gcaggctgag   120
ggaacgacct gtaacgttgg atctatcgcc tgctgcaact caccagccga gactaataac   180
gatagcctac ttagtggact ctcggagct ggacttctta acggacttag tggtaacaca    240
ggatcagctt gcgctaaggc cagccttatt gatcagcttg acttctcgc tcttgttgat    300
cacactgaag agggaccagt gtgtaagaat attgtggctt gctgtccaga gggtactact   360
aactgtgttg ctgttgataa tgctggtgct ggaactaagg ctgaataa                408
```

<210> SEQ ID NO 62
<211> LENGTH: 408
<212> TYPE: DNA
<213> ORGANISM: Artificial sequence
<220> FEATURE:
<223> OTHER INFORMATION: Nucleotide sequence hydrophobin variant 8

<400> SEQUENCE: 62

```
atgcgtttta tcgttagcct tctcgctttc actgctgctg ctactgctac agctatgcca    60
gctagtgctg ctaagaacgc taaacttgct actagtgctg ctttcgcaaa gcaagctgag   120
```

```
ggaactactt gtaacgtggg atctattgcc tgttgtaact caccagctga gactaacaac      180
gatagccttc ttagtggatt acttggagct ggacttctta acggacttag tggtaacact      240
ggatcagctt gcgctaaggc tagccttatt gatcaattgg gacttcttgc gttagttgat      300
cacactgaag aaggaccagt gtgtaagaat attgtggctt gctgcccaga gggtactact      360
aactgtgttg ctgtagacaa cgctggtgct ggcactaagg ctgaataa                   408
```

<210> SEQ ID NO 63
<211> LENGTH: 597
<212> TYPE: DNA
<213> ORGANISM: Artificial sequence
<220> FEATURE:
<223> OTHER INFORMATION: Nucleotide sequence Hydrophobin fusion protein, variant 1

<400> SEQUENCE: 63

```
atgaaaacaa atatgttttt atttatgatt ttttcgttga tgttaagtct cagttcggca       60
gcacagacag ggacagagcg ggtaaaacgt gggatggcgg agatgcagaa aggcggggtc      120
atcatggatg tcataaaatgc ggaacaggca aaaatagcag aggaagcagg cgcagttata     180
gaaggacgaa tgcgattcat agtatcactg ttggcattta ccgcggcggc aaccgccacg      240
gcaatgccgg cgtccgccgc aaaaaatgcg aaactcgcga catccgctgc atttgcgaaa      300
caggccgaag gtaccacgtg caatgtcggc tccattgctt gttgcaattc acctgcagaa      360
accaataatg actcactcct atctggtttg ttgggcgccg gcctattgaa tgggctcagc      420
ggcaataccg gctcagcctg tgcaaaagcc tccctgatag accaattagg ccttcttgca      480
ttagtagacc atactgaaga agggccggtt tgcaaaaaca tagtcgcgtg ttgtcccgaa      540
gggacgacca actgcgtggc ggtggacaac gcgggcgctg gcaccaaagc ggagtga        597
```

<210> SEQ ID NO 64
<211> LENGTH: 597
<212> TYPE: DNA
<213> ORGANISM: Artificial sequence
<220> FEATURE:
<223> OTHER INFORMATION: Nucleotide sequence Hydrophobin fusion protein, variant 2

<400> SEQUENCE: 64

```
atgaagacaa atatgtttct tttcatgatt ttcagcctta tgctgtcgtt atcttctgca       60
gcacagacag ggacagagcg tgttaagagg gggatggcag aaatgcagaa agggggagtg      120
ataatggacg tgattaatgc ggaacaagcg aaaatagcag aggaggctgg ggctgtcata      180
gaaggaagaa tgcggttcat cgtttcgctg ctcgcgttta ccgcggccgc tactgcaact      240
gcaatgcccg ctagtgcggc gaaaaatgcc aaacttgcaa cctcagctgc gtttgcgaaa      300
caggcagaag ggactacatg caacgttgga tcaattgcat gttgcaacag tcctgccgaa      360
acaaataatg actctttgct cagcggcttg ttggggccg cttacttaa tggattatcc        420 ggaaatacgg gctcagcttg tgcgaaagca tcccttattg accagttagg tctgctagct      480
ctcgtggacc acacggagga aggccctgtg tgcaaaaaca tcgtagcgtg ttgcccggag      540
ggaactacga attgcgttgc agtagacaat gcgggcgcag gtaccaaggc ggagtaa        597
```

<210> SEQ ID NO 65
<211> LENGTH: 597
<212> TYPE: DNA
<213> ORGANISM: Artificial sequence
<220> FEATURE:

<223> OTHER INFORMATION: Nucleotide sequence Hydrophobin fusion protein, variant 3

<400> SEQUENCE: 65

| | |
|---|---|
| atgaaaacca atatgttcct ctttatgatc tttagtttga tgctaagcct gagcagtgcc | 60 |
| gctcaaacgg gaactgagag agttaaaagg gggatggcag agatgcagaa aggggggtgtg | 120 |
| attatggacg tcataaacgc ggaacaggcc aaaattgccg aggaggctgg ggctgttata | 180 |
| gagggccgga tgcgatttat agtcagtctc ttggccttta ctgcagctgc tacagctacc | 240 |
| gcgttgccag cctccgctgc aaaaaatgct aagctggcca catctgctgc atttgctaaa | 300 |
| caggccgaag gtactacctg taatgtgggg tcgatagcct gttgcaattc accagcggag | 360 |
| acaaataatg actcgctcct aagtggatta ctaggggctg gctactcaa cggattatcg | 420 |
| ggtaatacgg gatcagcgtg cgctaaagct tccctgattg atcagcttgg acttcttgcc | 480 |
| ctagttgacc atacagagga gggaccagtt tgcaaaaata ttgtcgcgtg ctgtcctgag | 540 |
| ggtaccacga actgtgtagc agttgacaac gctggtgcgg gcacaaaagc ggagtag | 597 |

<210> SEQ ID NO 66
<211> LENGTH: 597
<212> TYPE: DNA
<213> ORGANISM: Artificial sequence
<220> FEATURE:
<223> OTHER INFORMATION: Nucleotide sequence Hydrophobin fusion protein, variant 4

<400> SEQUENCE: 66

| | |
|---|---|
| atgaagacta acatgttttt gtttctgata ttttcactta tgctatcgct cagctcggcg | 60 |
| gctcaaacgg gaaccgaaag ggttaagcgg ggtatggctg agatgcaaaa gggtggtgtt | 120 |
| attatggacg ttataaacgc tgaacaggca aagattgccg aggaggcagg tgcggttatt | 180 |
| gaaggaagaa tgcgatttat cgttagcctt cttgctttca ctgcagccgc gactgcgaca | 240 |
| gctttgccag cgagcgcagc taagaacgcg aaattggcta cctcggctgc ttttgccaaa | 300 |
| caggcagagg gaaccacgtg taatgtaggc tcgatcgcct gttgtaactc tccagccgag | 360 |
| actaacaatg attctcttct aagtggactg cttggagctg gcttactgaa cggactatca | 420 |
| ggtaatacag gaagtgcttg cgcaaaagct agccttatcg atcagttggg acttcttgct | 480 |
| ctggttgacc atacggagga gggaccagtg tgtaagaaca ttgtggcttg ctgcccagaa | 540 |
| ggtaccacta actgcgttgc tgttgataac gcaggggcgg gtacgaaagc ggagtga | 597 |

<210> SEQ ID NO 67
<211> LENGTH: 597
<212> TYPE: DNA
<213> ORGANISM: Artificial sequence
<220> FEATURE:
<223> OTHER INFORMATION: Nucleotide sequence Hydrophobin fusion protein, variant 5

<400> SEQUENCE: 67

| | |
|---|---|
| atgaaaacta acctgttcct cttcatgata ttttcacttt tgcttagtct tagctcagcc | 60 |
| gctcaaacgg gaactgaaag ggttaagagg ggcatggctg agatgcaaaa gggcggggtg | 120 |
| atcatggacg tgatcaatgc tgagcaggcg aagattgctg aggaagctgg ggctgtaatt | 180 |
| gagggaagaa tgcgcttcat cgtcagccct ttggctttta ctgcggctgc tactgctaca | 240 |
| gcgttgcccg ctagtgctgc taagaacgct aagcttgcta ccagtgccgc tttcgcaaag | 300 |
| caagctgagg gaacaacttg taatgtgggt tcgatcgcct gctgtaactc accagctgag | 360 |

```
accaacaacg acagccttct tagtggactc cttggcgccg gccttcttaa cgggcttagt    420
ggtaatactg gttcagcttg cgcgaaggct tcactcattg atcaacttgg gcttttggct    480
ctcgttgatc atactgaaga gggaccggtg tgtaagaata tcgtggcgtg ctgtccagag    540
ggtactacta actgtgtcgc tgtggataac gcaggtgccg gcactaaggc cgaataa      597
```

<210> SEQ ID NO 68
<211> LENGTH: 597
<212> TYPE: DNA
<213> ORGANISM: Artificial sequence
<220> FEATURE:
<223> OTHER INFORMATION: Nucleotide sequence Hydrophobin fusion protein, variant 6

<400> SEQUENCE: 68

```
atgaagacta acctgttcct cttcctgatc ttcagccttt tgcttagcct ttcctcagct     60
gctcagactg gtacagaaag ggttaagaga ggtatggctg aaatgcaaaa gggtggtgtg    120
attatggacg tcataaacgc ggaacaggct aaaatcgctg aagaagctgg ggctgttata    180
gagggtcgaa tgcgttttat agttagtctt cttgctttta ctgctgccgc tactgctaca    240
gctttgccag ctagcgccgc taaaaatgct aaacttgcca cgtccgctgc tttcgcgaag    300
caagctgagg ggactacatg caacgtcgga tctattgcct gctgtaactc gccagctgag    360
acaaataacg attcccttct ttctggactt cttggagctg gacttcttaa cggccttttcc    420 ggaaacactg gatcagcttg cgctaaggct agccttattg atcaacttgg acttcttgct    480
ctcgttgatc acactgaaga aggaccagtg tgtaagaaca ttgtggcctg ctgcccagag    540
ggtactacta actgtgttgc agttgataac gctggagctg gaactaaggc ggaatga       597
```

<210> SEQ ID NO 69
<211> LENGTH: 597
<212> TYPE: DNA
<213> ORGANISM: Artificial sequence
<220> FEATURE:
<223> OTHER INFORMATION: Nucleotide sequence Hydrophobin fusion protein, variant 7

<400> SEQUENCE: 69

```
atgaagacta acctgttcct cttcctgatc ttctcactgt tgcttagcct tagctcagct     60
gctcaaactg gaactgaaag ggttaagagg ggtatggctg aaatgcagaa gggcggtgta    120
attatggacg tcatcaacgc tgagcaggct aagattgccg aggaggctgg tgctgttatt    180
gaggggagaa tgcgttttat cgtttctta cttgctttca cagctgctgc tactgctaca    240
gctatgccag ctagtgctgc taagaacgct aagcttgcta ctagtgctgc cttcgctaag    300
caggctgagg gaactacgtg taacgtaggg tctattgcat gctgtaactc accggctgag    360
actaataatg atagccttct aagtggactt cttggagctg gtcttcttaa cggtctttcg    420
ggtaacactg gatcagcttg cgctaaggct agccttattg atcaacttgg acttcttgct    480
ctcgttgacc acactgagga gggaccagtt tgcaagaata ttgtggcttg ctgcccagag    540
ggtactacta actgtgttgc tgttgacaac gctggtgctg gaactaaggc tgaataa       597
```

<210> SEQ ID NO 70
<211> LENGTH: 597
<212> TYPE: DNA
<213> ORGANISM: Artificial sequence
<220> FEATURE:
<223> OTHER INFORMATION: Nucleotide sequence Hydrophobin fusion protein, variant 8

-continued

<400> SEQUENCE: 70

```
atgaagacaa acctgttcct cttcctgatc ttctcacttt tgctttcact tagcagcgct    60
gctcaaactg gcacagaacg ggttaaaaga ggtatggctg aaatgcaaaa ggggggtgtg   120
attatggacg tgatcaacgc tgaacaggct aagattgctg aagaggctgg tgctgttatc   180
gaaggtagaa tgcgttttat cgttagcctt cttgccttca ctgctgctgc tactgctaca   240
gctttgccag ctagtgctgc taagaacgct aagcttgcta ctagtgctgc tttcgctaag   300
caagctgagg gaactacttg taacgtggga agtattgcct gctgtaactc accagctgag   360
actaacaacg atagccttct tagtggactt cttggagctg gacttcttaa cggacttagt   420
ggtaacactg gatcagcttg cgctaaggct agccttattg atcaacttgg acttcttgct   480
ctcgttgatc acactgaaga gggaccagtg tgtaagaata ttgtggcttg ctgcccagaa   540
ggtactacta actgtgttgc tgtggataac gctggtgcag ggactaaggc tgaataa      597
```

<210> SEQ ID NO 71
<211> LENGTH: 594
<212> TYPE: DNA
<213> ORGANISM: Artificial sequence
<220> FEATURE:
<223> OTHER INFORMATION: Nucleotide sequence Hydrophobin fusion protein, variant 9

<400> SEQUENCE: 71

```
atgaagacca acctgttcct gttcctgatc ttcagcctgc tgctgagcct gagcagcgcc    60
gcccagaccg gcaccgagag agtgaagaga ggcgccatcg agatgaacag aggcggcatc   120
atcatggacg tgatcaacgc cgacaacgcc aagatcgccg aggaggccgg cgccgtgatc   180
gagggccaca tgagattcat cgtgagcatc ctgctgtgga ccgccgccgc caccgccctg   240
atgggccccg ccaccgccgc cagaaacctg agaggcatca ccaccgccgc cttcctgaga   300
caggccgacg gcaccacctg ccagggcggc agcatcatgt gctgccagag ccccatggag   360
accaaccagg acaccatcct gagcggcggc ctgggcctgg gcatgggcca ggtgatcacc   420
ggcaacagcg gcagcgcctg cgtgaagatc agcctgatcg acaacctggg cctgctggcc   480
ctggtggacc actgcgacga gggccccatg agcaagaacg tggtggcctg cacccccgac   540
atgaccagca acagcgtggc cgtggacaac ggcatgctgg gctgccacgc cgag         594
```

<210> SEQ ID NO 72
<211> LENGTH: 198
<212> TYPE: PRT
<213> ORGANISM: Artificial sequence
<220> FEATURE:
<223> OTHER INFORMATION: Amino acid sequence Hydrophobin fusion protein, variant 9

<400> SEQUENCE: 72

```
Met Lys Thr Asn Leu Phe Leu Phe Leu Ile Phe Ser Leu Leu Leu Ser
1               5                  10                  15

Leu Ser Ser Ala Ala Gln Thr Gly Thr Glu Arg Val His Arg Gly Met
            20                  25                  30

Ala Glu Met Gln Lys Gly Gly Val Ile Met Asp Val Ile Asn Ala Asp
        35                  40                  45

Gln Val His Ile Ala Glu Asp Ala Gly Leu Gly Leu Glu Gly Arg Met
    50                  55                  60

His Trp Met Met Thr Leu Leu Leu Phe Ser Ala Ala Ala Thr Leu Thr
65                  70                  75                  80
```

```
Ala Leu Pro Ala Ser Gly Ala Lys Asn Ala Lys Ile Ala Thr Ser Ala
                85                  90                  95

Met Phe Ala His Asn Val Glu Gly Ser Thr Cys Asn Val Gly Ser Leu
            100                 105                 110

Leu Ser Cys Gln Thr Pro Ala Asp Thr Asn Asn Asp Ser Leu Leu Ser
        115                 120                 125

Ile Met Leu Ile Ala Met Leu Gly Gln Gly Leu Ser Ala Gln Thr Gly
    130                 135                 140

Cys Val Cys Ala His Ala Ser Met Ala Glu Asn Leu Gly Leu Met Val
145                 150                 155                 160

Leu Val Glu Arg Thr Glu Glu Gly Pro Leu Cys Lys Asn Val Val Ala
                165                 170                 175

Cys Cys Pro Asp Gly Thr Cys Gln Cys Ala Val Val Asp Asn Gly Gly
            180                 185                 190

Ile Gly Thr Arg Leu Glu
                195

<210> SEQ ID NO 73
<211> LENGTH: 594
<212> TYPE: DNA
<213> ORGANISM: Artificial sequence
<220> FEATURE:
<223> OTHER INFORMATION: Nucleotide sequence Hydrophobin fusion protein,
      variant 10

<400> SEQUENCE: 73
atgaagacca acctgttcct gttcctgatc ttcagcctgc tgctgagcct gagcagcgcc      60
gcccagaccg gcaccgagag agtgaagaga ggcatgatgg acggccagca cctgctggtg     120
gccatggaca tgatgaacat ggagcaggcc aagatcgccg aggaggccgg cgccgtgatc     180
gagggccacg ccagattcat ggtgagcctg ctggccttca ccgccatcgc caccatcacc     240
gccctgcccg ccagcgccgg caccaggcc agactggcca ccaccgccgc ctacgtgcac      300
aacgccgagc tgacctgcac caacgtgctg tgcatcgcct gctgccagag ccccgccgag     360
acccagcagg acagcctgct gagcggcgtg ctgatgatgg gcctgctgaa cggcctgagc     420
ggcaacaccg gctgcatgtg cgccagagcc agcctgatcg accagctggg cctgctggcc     480
atggtggacc acagcgagga gggcccggc tgcaagaacg tggtggccac ctgccccgag      540
ggcaccagca actgcgtggg cgtggagaac atgggcgcca tcaccaagct ggag            594

<210> SEQ ID NO 74
<211> LENGTH: 198
<212> TYPE: PRT
<213> ORGANISM: Artificial sequence
<220> FEATURE:
<223> OTHER INFORMATION: Amino acid sequence Hydrophobin fusion protein,
      variant 10

<400> SEQUENCE: 74

Met Lys Thr Asn Leu Phe Leu Phe Leu Ile Phe Ser Leu Leu Leu Ser
1               5                   10                  15

Leu Ser Ser Ala Ala Gln Thr Gly Thr Glu Arg Val Lys Arg Gly Met
            20                  25                  30

Met Asp Gly Gln His Leu Leu Val Ala Met Asp Met Met Asn Met Glu
        35                  40                  45

Gln Ala Lys Ile Ala Glu Glu Ala Gly Ala Val Ile Glu Gly His Ala
    50                  55                  60

Arg Phe Met Val Ser Leu Leu Ala Phe Thr Ala Ile Ala Thr Ile Thr
```

```
                65                  70                  75                  80
Ala Leu Pro Ala Ser Ala Gly His Gln Ala Arg Leu Ala Thr Thr Ala
                    85                  90                  95

Ala Tyr Val His Asn Ala Glu Leu Thr Cys Thr Asn Val Leu Cys Ile
                100                 105                 110

Ala Cys Cys Gln Ser Pro Ala Glu Thr Gln Gln Asp Ser Leu Leu Ser
            115                 120                 125

Gly Val Leu Met Met Gly Leu Leu Asn Gly Leu Ser Gly Asn Thr Gly
        130                 135                 140

Cys Met Cys Ala Arg Ala Ser Leu Ile Asp Gln Leu Gly Leu Leu Ala
145                 150                 155                 160

Met Val Asp His Ser Glu Gly Pro Gly Cys Lys Asn Val Val Ala
                165                 170                 175

Thr Cys Pro Glu Gly Thr Ser Asn Cys Val Gly Val Glu Asn Met Gly
            180                 185                 190

Ala Ile Thr Lys Leu Glu
        195

<210> SEQ ID NO 75
<211> LENGTH: 594
<212> TYPE: DNA
<213> ORGANISM: Artificial sequence
<220> FEATURE:
<223> OTHER INFORMATION: Nucleotide sequence Hydrophobin fusion protein,
      variant 11

<400> SEQUENCE: 75
atgaagacca acctgttcct gttcctgatc ttcagcctgc tgctgagcct gagcagcgcc      60
gcccagtgcg gcaccgagag agtgaagaga ggcatggccg agatgcagaa gggcggcgtg     120
atcatggacg tgatcaacgc cgagaacgcc aagatcgccg aggaggccgg cgccatcatg     180
gagggcaaga tgaagttcat cgtgagcctg atggcctgga ccgccgccat gtgcgccacc     240
gccctgcccg cctgcgccgc caagaacgcc aagctggcca ccagcggcct gtacgcccac     300
cagggcgacg gcaccacctg caacatgggc agcatcgcct gctgcaacag ccccgccgac     360
accaaccagg acagcctgct gaccggcctg ctgggcgcca tgctgctgca gggcggctgc     420
gtgaacagcg ccaccgcctg cgccaaggtg agcctgatgg agcagctggg cctgctggcc     480
ctggtggaca gaaccgagga gatccccgtg tgcaagaacc tgctggccac ctgccccgag     540
ggcaccacca actgcgtggc cggcgagaac gccggcgccg caccaaggc cgag            594

<210> SEQ ID NO 76
<211> LENGTH: 198
<212> TYPE: PRT
<213> ORGANISM: Artificial sequence
<220> FEATURE:
<223> OTHER INFORMATION: Amino acid sequence Hydrophobin fusion protein,
      variant 11

<400> SEQUENCE: 76

Met Lys Thr Asn Leu Phe Leu Phe Leu Ile Phe Ser Leu Leu Leu Ser
1               5                   10                  15

Leu Ser Ser Ala Ala Gln Cys Gly Thr Glu Arg Val Lys Arg Gly Met
            20                  25                  30

Ala Glu Met Gln Lys Gly Gly Val Ile Met Asp Val Ile Asn Ala Glu
        35                  40                  45

Asn Ala Lys Ile Ala Glu Glu Ala Gly Ala Ile Met Glu Gly Lys Met
    50                  55                  60
```

```
Lys Phe Ile Val Ser Leu Met Ala Trp Thr Ala Ala Met Cys Ala Thr
 65                  70                  75                  80

Ala Leu Pro Ala Cys Ala Ala Lys Asn Ala Lys Leu Ala Thr Ser Gly
             85                  90                  95

Leu Tyr Ala His Gln Gly Asp Gly Thr Thr Cys Asn Met Gly Ser Ile
        100                 105                 110

Ala Cys Cys Asn Ser Pro Ala Asp Thr Asn Gln Asp Ser Leu Leu Thr
        115                 120                 125

Gly Leu Leu Gly Ala Met Leu Leu Gln Gly Gly Cys Val Asn Ser Ala
        130                 135                 140

Thr Ala Cys Ala Lys Val Ser Leu Met Glu Gln Leu Gly Leu Leu Ala
145                 150                 155                 160

Leu Val Asp Arg Thr Glu Glu Ile Pro Val Cys Lys Asn Leu Leu Ala
                165                 170                 175

Thr Cys Pro Glu Gly Thr Thr Asn Cys Val Ala Gly Glu Asn Ala Gly
            180                 185                 190

Ala Gly Thr Lys Ala Glu
            195
```

```
<210> SEQ ID NO 77
<211> LENGTH: 594
<212> TYPE: DNA
<213> ORGANISM: Artificial sequence
<220> FEATURE:
<223> OTHER INFORMATION: Nucleotide sequence Hydrophobin fusion protein,
      variant 12

<400> SEQUENCE: 77
atgaagacca acctgttcct gttcctgatc ttcagcctgc tgctgagcct gagcagcgcc     60
gcccagacca tgagcgagag agtgagaaga ggcatggccg agatgcagaa gggcggcgtg    120
atcatggacg tgatcaacgc cgagcaggcc aagatcgccg acgaggccgg cggcgtgatc    180
gagggcagaa tgagattcat cgccagcctg atggccttca ccgccgccgc caccgccacc    240
gccctgcccg ccagcgccgc caagaacgcc aagggcgcca gcagcatcgc cttcgccaag    300
caggccgaga tgaccacctg caacgccggc agcatcggct gctgcaacag ccccgccgag    360
accaacaacg acagcctggg caccctggcc ctgctgatgg gcctgggcaa cggcctgagc    420
ggcaacaccg gcgcgcctg cctgaaggcc agcctgatcg accagctgat ggtgctggcc    480
ctggtggacc actgcgagga cggccccgtg tgccacaaca tcatggcctg ctgccccgac    540
ggcaccacca ctgcgtggc cgtggacaac gccggcgcca tcaccaaggg cgag           594
```

```
<210> SEQ ID NO 78
<211> LENGTH: 198
<212> TYPE: PRT
<213> ORGANISM: Artificial sequence
<220> FEATURE:
<223> OTHER INFORMATION: Amino acid sequence Hydrophobin fusion protein,
      variant 12

<400> SEQUENCE: 78

Met Lys Thr Asn Leu Phe Leu Phe Leu Ile Phe Ser Leu Leu Leu Ser
1               5                   10                  15

Leu Ser Ser Ala Ala Gln Thr Met Ser Glu Arg Val Arg Arg Gly Met
            20                  25                  30

Ala Glu Met Gln Lys Gly Gly Val Ile Met Asp Val Ile Asn Ala Glu
        35                  40                  45
```

```
Gln Ala Lys Ile Ala Asp Glu Ala Gly Gly Val Ile Glu Gly Arg Met
 50                  55                  60
Arg Phe Ile Ala Ser Leu Met Ala Phe Thr Ala Ala Thr Ala Thr
 65                  70                  75                  80
Ala Leu Pro Ala Ser Ala Ala Lys Asn Ala Lys Gly Ala Ser Ser Ile
                 85                  90                  95
Ala Phe Ala Lys Gln Ala Glu Met Thr Thr Cys Asn Ala Gly Ser Ile
                100                 105                 110
Gly Cys Cys Asn Ser Pro Ala Glu Thr Asn Asn Asp Ser Leu Gly Thr
                115                 120                 125
Leu Ala Leu Leu Met Gly Leu Gly Asn Gly Leu Ser Gly Asn Thr Gly
            130                 135                 140
Ser Ala Cys Leu Lys Ala Ser Leu Ile Asp Gln Leu Met Val Leu Ala
145                 150                 155                 160
Leu Val Asp His Cys Glu Asp Gly Pro Val Cys His Asn Ile Met Ala
                165                 170                 175
Cys Cys Pro Asp Gly Thr Thr Asn Cys Val Ala Val Asp Asn Ala Gly
                180                 185                 190
Ala Ile Thr Lys Gly Glu
            195
```

<210> SEQ ID NO 79
<211> LENGTH: 594
<212> TYPE: DNA
<213> ORGANISM: Artificial sequence
<220> FEATURE:
<223> OTHER INFORMATION: Nucleotide sequence Hydrophobin fusion protein,
      variant 13

<400> SEQUENCE: 79

```
atgaagacca acctgttcct gttcctgatc ttcagcctgc tgctgagcct gagcagcgcc      60
gcccagaccg gcaccgagag agtgaagaga ggcatggccg aggtgcagaa gggcggcgtg     120
atcggcgacg tgggcaacgc cgagcaggcc aagatcgccg aggaggccgg cggcgtgatc     180
gagggcagaa tgagattcat cgtgagcctg ctggccttca ccgccgccgc caccgccagc     240
gccctgcccg ccagcgccgc cacaacgcc aagctgctgt gcagcgccat gttcgccaag     300
caggccgagg gcaccacctg caacgtggcc agcatcgcct gctgccagag ccccgccgag     360
accaaccagg acaccctgct gagcggcctg ctgggcgccg ccctgctgaa cggcctgagc     420
ggcaacaccg gcagcgccac cgccaaggcc agcctgatcg accagctggg cctgctggcc     480
atcgtggacc acaccgagga cggccccgtg tgcaagaacg tggtggcctg ctgccccgag     540
ggcaccacca actgcgtggc cgtggacaac gccgccctgg caccaaggc cgac           594
```

<210> SEQ ID NO 80
<211> LENGTH: 198
<212> TYPE: PRT
<213> ORGANISM: Artificial sequence
<220> FEATURE:
<223> OTHER INFORMATION: Amino acid sequence Hydrophobin fusion protein,
      variant 13

<400> SEQUENCE: 80

```
Met Lys Thr Asn Leu Phe Leu Phe Leu Ile Phe Ser Leu Leu Leu Ser
 1               5                  10                  15
Leu Ser Ser Ala Ala Gln Thr Gly Thr Glu Arg Val Lys Arg Gly Met
                20                  25                  30
Ala Glu Val Gln Lys Gly Gly Val Ile Gly Asp Val Gly Asn Ala Glu
```

```
            35                  40                  45
Gln Ala Lys Ile Ala Glu Glu Ala Gly Ala Val Ile Glu Gly Arg Met
         50                  55                  60

Arg Phe Ile Val Ser Leu Leu Ala Phe Thr Ala Ala Thr Ala Ser
65                  70                  75                  80

Ala Leu Pro Ala Ser Ala Ala His Asn Ala Lys Leu Leu Cys Ser Ala
                 85                  90                  95

Met Phe Ala Lys Gln Ala Glu Gly Thr Thr Cys Asn Val Ala Ser Ile
            100                 105                 110

Ala Cys Cys Gln Ser Pro Ala Glu Thr Asn Gln Asp Thr Leu Leu Ser
        115                 120                 125

Gly Leu Leu Gly Ala Ala Leu Leu Asn Gly Leu Ser Gly Asn Thr Gly
    130                 135                 140

Ser Ala Thr Ala Lys Ala Ser Leu Ile Asp Gln Leu Gly Leu Leu Ala
145                 150                 155                 160

Ile Val Asp His Thr Glu Asp Gly Pro Val Cys Lys Asn Val Val Ala
                165                 170                 175

Cys Cys Pro Glu Gly Thr Thr Asn Cys Val Ala Val Asp Asn Ala Ala
            180                 185                 190

Leu Gly Thr Lys Ala Asp
        195
```

<210> SEQ ID NO 81
<211> LENGTH: 594
<212> TYPE: DNA
<213> ORGANISM: Artificial sequence
<220> FEATURE:
<223> OTHER INFORMATION: Nucleotide sequence Hydrophobin fusion protein, variant 14

<400> SEQUENCE: 81

```
atgaagacca acctgttcct gttcctgatc ttcagcctgc tgctgagcct gagcagcgcc      60
gcccagaccg gcaccgagag agtgaagaga ggcatggccg acatgcagaa gggcggcgtg     120
atcatggacg tgatcaacgc cgaccaggcc aagatcgccg aggaggccgg cgccgtgatc     180
gagggcagaa tgagattcat cgtgagcctg gccgccttca ccgccgccgc caccgccacc     240
gccctgcccg ccagcgccgc caagaacgcc aagctggcca ccagcgccgc ctgggccaag     300
caggccgagg gcaccacctg caacgtgggc agcatcgcct gctgccagag ccccgccgag     360
accaacaacg acaccgtgct gagcggcctg ctggtggccg cctgctgaa cggcctgagc      420
ggcaacaccg gcagcgccac cgccagagtg agcctgatgg accagctggg cctgctggcc     480
ctggtggacc acaccgagga gggccccgcc tgcaagaaca tcgtggcctg ctgccccgag     540
ggcaccacca actgcgtggc cgtggaccag gccggcatgg caccaaggc cgac            594
```

<210> SEQ ID NO 82
<211> LENGTH: 198
<212> TYPE: PRT
<213> ORGANISM: Artificial sequence
<220> FEATURE:
<223> OTHER INFORMATION: Amino acid sequence Hydrophobin fusion protein, variant 14

<400> SEQUENCE: 82

```
Met Lys Thr Asn Leu Phe Leu Phe Leu Ile Phe Ser Leu Leu Leu Ser
1                5                  10                  15

Leu Ser Ser Ala Ala Gln Thr Gly Thr Glu Arg Val Lys Arg Gly Met
            20                  25                  30
```

Ala Asp Met Gln Lys Gly Gly Val Ile Met Asp Val Ile Asn Ala Asp
         35                  40                  45

Gln Ala Lys Ile Ala Glu Glu Ala Gly Ala Val Ile Glu Gly Arg Met
     50                  55                  60

Arg Phe Ile Val Ser Leu Ala Phe Thr Ala Ala Thr Ala Thr
65                  70                  75                  80

Ala Leu Pro Ala Ser Ala Ala Lys Asn Ala Lys Leu Ala Thr Ser Ala
                 85                  90                  95

Ala Trp Ala Lys Gln Ala Glu Gly Thr Thr Cys Asn Val Gly Ser Ile
                100                 105                 110

Ala Cys Cys Gln Ser Pro Ala Glu Thr Asn Asn Asp Thr Val Leu Ser
                115                 120                 125

Gly Leu Leu Val Ala Gly Leu Leu Asn Gly Leu Ser Gly Asn Thr Gly
        130                 135                 140

Ser Ala Thr Ala Arg Val Ser Leu Met Asp Gln Leu Gly Leu Leu Ala
145                 150                 155                 160

Leu Val Asp His Thr Glu Glu Gly Pro Ala Cys Lys Asn Ile Val Ala
                165                 170                 175

Cys Cys Pro Glu Gly Thr Thr Asn Cys Val Ala Val Asp Gln Ala Gly
                180                 185                 190

Met Gly Thr Lys Ala Asp
        195

<210> SEQ ID NO 83
<211> LENGTH: 594
<212> TYPE: DNA
<213> ORGANISM: Artificial sequence
<220> FEATURE:
<223> OTHER INFORMATION: Nucleotide sequence Hydrophobin fusion protein,
      variant 15

<400> SEQUENCE: 83
atgaagacca acctgttcct gttcctgatc ttcagcctgc tgctgagcct gagcagcgcc      60
gcccagaccg gcaccgagag agtgaagaga ggcatggccg agatgcagaa gggcggcgtg     120
atcatggacg tgatcaacgc cgagcaggcc aagatcgccg aggaggccgg cgccgtgatc     180
gagggcagaa tgagattcat cgtgagcctg ctggccttca ccctggccgc caccgcctgc     240
gccctgcccg ccagcatggc caagaacgcc aagctgggca ccagcatcgc cttcgccaag     300
caggccgagg gcaccacctg caacgtgggc agcatcgcct gctgcaacag ccccgccgag     360
accaacaacg acagcctgct gagcggcctg ctgggcgccg gctgctgaa cggcctgagc     420 ggcaacaccg gcagcgccct cgccaaggcc agcctgatcg acaacctggg cctgctggcc     480
ctggtggaca gaccgagga gggccccgtg tgcaagaaca tcgtggcctg ctgccccgac     540
ggcaccacca actgcgtggc cgtggacaac atgggcgccg gcaccaaggc cgac          594

<210> SEQ ID NO 84
<211> LENGTH: 198
<212> TYPE: PRT
<213> ORGANISM: Artificial sequence
<220> FEATURE:
<223> OTHER INFORMATION: Amino acid sequence Hydrophobin fusion protein,
      variant 15

<400> SEQUENCE: 84

Met Lys Thr Asn Leu Phe Leu Phe Leu Ile Phe Ser Leu Leu Leu Ser
1               5                  10                  15

Leu Ser Ser Ala Ala Gln Thr Gly Thr Glu Arg Val Lys Arg Gly Met
            20                  25                  30

Ala Glu Met Gln Lys Gly Gly Val Ile Met Asp Val Ile Asn Ala Glu
        35                  40                  45

Gln Ala Lys Ile Ala Glu Glu Ala Gly Ala Val Ile Glu Gly Arg Met
    50                  55                  60

Arg Phe Ile Val Ser Leu Leu Ala Phe Thr Leu Ala Ala Thr Ala Cys
65                  70                  75                  80

Ala Leu Pro Ala Ser Met Ala Lys Asn Ala Lys Leu Gly Thr Ser Ile
                85                  90                  95

Ala Phe Ala Lys Gln Ala Glu Gly Thr Thr Cys Asn Val Gly Ser Ile
            100                 105                 110

Ala Cys Cys Asn Ser Pro Ala Glu Thr Asn Asn Asp Ser Leu Leu Ser
        115                 120                 125

Gly Leu Leu Gly Ala Gly Leu Leu Asn Gly Leu Ser Gly Asn Thr Gly
    130                 135                 140

Ser Ala Cys Ala Lys Ala Ser Leu Ile Asp Asn Leu Gly Leu Leu Ala
145                 150                 155                 160

Leu Val Asp Lys Thr Glu Glu Gly Pro Val Cys Lys Asn Ile Val Ala
                165                 170                 175

Cys Cys Pro Asp Gly Thr Thr Asn Cys Val Ala Val Asp Asn Met Gly
            180                 185                 190

Ala Gly Thr Lys Ala Asp
        195

<210> SEQ ID NO 85
<211> LENGTH: 594
<212> TYPE: DNA
<213> ORGANISM: Artificial sequence
<220> FEATURE:
<223> OTHER INFORMATION: Nucleotide sequence Hydrophobin fusion protein,
      variant 16

<400> SEQUENCE: 85
atgaagacca acctgttcct gttcctgatc ttcagcctgc tgctgagcct gagcagcgcc      60
gcccagaccg gctgcgagag agtgaagaga ggcatggccg agatgcagaa gggcggcgtg     120
atcatggacg tgatcaacgc cgagcaggcc cacatcgccg aggaggccgg cgccgtgatc     180
gagggcagaa tgagattcat cgtgagcctg ctggccttca ccgccgtggc caccgccacc     240
gccctgcccg ccagcgccgc caagaacgcc aagctggcca ccagcgccgc cttcgccaag     300
caggccgagg gcaccaccctg aacgtgggc agcatcgcct gctgcaacag ccccgccgag     360
accaacaacg acagcctgct gagcggcctg ctgggcgccg gcctgctgaa cggcctgagc     420
ggcaacaccg gcagcgcctg cgccaaggcc agcctgatcg accagctggg cctgctggcc     480
ctggtggacc acaccgagga cggccccgtg tgcaagaaca tcgtggcctg ctgccccgag     540
ggcagcacca actgcgtggc cgtggacaac gtgggcgccg gcaccaaggc cgag           594

<210> SEQ ID NO 86
<211> LENGTH: 198
<212> TYPE: PRT
<213> ORGANISM: Artificial sequence
<220> FEATURE:
<223> OTHER INFORMATION: Amino acid sequence Hydrophobin fusion protein,
      variant 16

<400> SEQUENCE: 86

Met Lys Thr Asn Leu Phe Leu Phe Leu Ile Phe Ser Leu Leu Leu Ser

```
                1               5                  10                  15
            Leu Ser Ser Ala Ala Gln Thr Gly Cys Glu Arg Val Lys Arg Gly Met
                        20                  25                  30

Ala Glu Met Gln Lys Gly Gly Val Ile Met Asp Val Ile Asn Ala Glu
                        35                  40                  45

Gln Ala His Ile Ala Glu Glu Ala Gly Ala Val Ile Glu Gly Arg Met
                        50                  55                  60

Arg Phe Ile Val Ser Leu Leu Ala Phe Thr Ala Val Ala Thr Ala Thr
            65                  70                  75                  80

Ala Leu Pro Ala Ser Ala Ala Lys Asn Ala Lys Leu Ala Thr Ser Ala
                        85                  90                  95

Ala Phe Ala Lys Gln Ala Glu Gly Thr Thr Cys Asn Val Gly Ser Ile
                        100                 105                 110

Ala Cys Cys Asn Ser Pro Ala Glu Thr Asn Asn Asp Ser Leu Leu Ser
                        115                 120                 125

Gly Leu Leu Gly Ala Gly Leu Leu Asn Gly Leu Ser Gly Asn Thr Gly
                        130                 135                 140

Ser Ala Cys Ala Lys Ala Ser Leu Ile Asp Gln Leu Gly Leu Leu Ala
            145                 150                 155                 160

Leu Val Asp His Thr Glu Asp Gly Pro Val Cys Lys Asn Ile Val Ala
                        165                 170                 175

Cys Cys Pro Glu Gly Ser Thr Asn Cys Val Ala Val Asp Asn Val Gly
                        180                 185                 190

Ala Gly Thr Lys Ala Glu
                        195

<210> SEQ ID NO 87
<211> LENGTH: 137
<212> TYPE: PRT
<213> ORGANISM: Artificial sequence
<220> FEATURE:
<223> OTHER INFORMATION: Amino acid sequence hydrophobin TT1

<400> SEQUENCE: 87

Met Ala Leu Pro Asn Val Gly Pro Ser Gly Lys Thr Ala His Lys Pro
            1               5                   10                  15

His Gln Glu Pro Phe Trp Pro Val Gln Gln Asp Val Thr Val Glu Gln
                        20                  25                  30

Ala Lys Ala Ile Cys Gly Glu Gly Asn Gln Val Ala Cys Cys Asn Glu
                        35                  40                  45

Val Ser Tyr Ala Gly Asp Thr Thr Glu Ile Ala Thr Gly Pro Leu Ala
                        50                  55                  60

Gly Thr Leu Lys Asp Leu Leu Gly Gly Lys Asn Gly Ala Lys Gly Leu
            65                  70                  75                  80

Gly Leu Phe Asp Lys Cys Ser Arg Leu Asn Val Asp Leu Leu Leu Gly
                        85                  90                  95

Leu Ser Ser Leu Ile Asn Gln Glu Cys Lys Gln His Ile Ala Cys Cys
                        100                 105                 110

Gln Gly Asn Glu Ala Asp Ser Ser Asn Asp Leu Ile Gly Leu Asn Ile
                        115                 120                 125

Pro Cys Ile Ala Leu Gly Ser Leu Leu
                        130                 135

<210> SEQ ID NO 88
<211> LENGTH: 97
<212> TYPE: PRT
```

-continued

<213> ORGANISM: Artificial sequence
<220> FEATURE:
<223> OTHER INFORMATION: Amino acid sequence hydrophobin HFPI

<400> SEQUENCE: 88

Met Lys Phe Phe Ala Ile Ala Ala Leu Phe Ala Ala Ala Val Ala
1               5                   10                  15

Gln Pro Leu Glu Asp Arg Ser Asn Gly Asn Gly Asn Val Cys Pro Pro
            20                  25                  30

Gly Leu Phe Ser Asn Pro Gln Cys Cys Ala Thr Gln Val Leu Gly Leu
        35                  40                  45

Ile Gly Leu Asp Cys Lys Val Pro Ser Gln Asn Val Tyr Asp Gly Thr
    50                  55                  60

Asp Phe Arg Asn Val Cys Ala Lys Thr Gly Ala Gln Pro Leu Cys Cys
65                  70                  75                  80

Val Ala Pro Val Ala Gly Gln Ala Leu Leu Cys Gln Thr Ala Val Gly
                85                  90                  95

Ala

<210> SEQ ID NO 89
<211> LENGTH: 411
<212> TYPE: DNA
<213> ORGANISM: Artificial
<220> FEATURE:
<223> OTHER INFORMATION: Nucleotide sequence hydrophobin TT1

<400> SEQUENCE: 89
atggccctgc caaacgtcgg tcccagtggg aagacggctc acaagccgca ccaggagcct      60
ttctggcctg tgcagcagga cgtgaccgtg aacaggcca aggctatctg tggtgaaggc      120
aaccaggtcg cttgctgcaa cgaggtcagc tacgcgggcg acaccaccga atcgcgacc      180 ggccccctgg ctggcaccct caaggacctg ctcggcggca agaacggcgc caagggcctg      240
ggtctcttcg acaagtgctc gcgtctcaat gtcgatctcc tgcttggcct gtcgagcctc      300
atcaaccaag aatgcaagca gcacattgcc tgctgccagg caacgaggc cgattcctcc      360 aacgacctca tcggtctcaa cattccttgc attgcccttg gctcgctgct g               411

<210> SEQ ID NO 90
<211> LENGTH: 291
<212> TYPE: DNA
<213> ORGANISM: Artificial sequence
<220> FEATURE:
<223> OTHER INFORMATION: Nucleotide sequence hydrophobin HFPI

<400> SEQUENCE: 90
atgaagttct tcgccatcgc cgctctcttt gccgccgctg ccgttgccca gcctctcgag      60
gaccgcagca acggcaacgg caatgtttgc cctcccggcc tcttcagcaa ccccagtgc      120 tgtgccaccc aagtccttgg cctcatcggc cttgactgca agtcccctc ccagaacgtt      180 tacgacggca ccgacttccg caacgtctgc gccaaaaccg gcgcccagcc tctctgctgc      240
gtggcccccg ttgccggcca ggctcttctg tgccagaccg ccgtcggtgc t               291